(12) United States Patent
Payne

(10) Patent No.: US 12,180,253 B2
(45) Date of Patent: *Dec. 31, 2024

(54) MATERIALS AND METHODS FOR TREATING Friedreich's Ataxia

(71) Applicant: THE TRUSTEES OF INDIANA UNIVERSITY, Bloomington, IN (US)

(72) Inventor: Ronald Mark Payne, Zionsville, IN (US)

(73) Assignee: The Trustees of Indiana University, Bloomington, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/900,450

(22) Filed: Aug. 31, 2022

(65) Prior Publication Data

US 2023/0242600 A1 Aug. 3, 2023

Related U.S. Application Data

(63) Continuation of application No. 16/942,276, filed on Jul. 29, 2020, now Pat. No. 11,459,363.

(60) Provisional application No. 62/891,029, filed on Aug. 23, 2019, provisional application No. 62/880,073, filed on Jul. 29, 2019.

(51) Int. Cl.
*A61K 38/17* (2006.01)
*A61K 9/00* (2006.01)
*A61P 9/02* (2006.01)
*A61P 25/28* (2006.01)
(Continued)

(52) U.S. Cl.
CPC ............ *C07K 14/47* (2013.01); *A61K 9/0019* (2013.01); *A61K 38/1709* (2013.01); *A61P 9/02* (2018.01); *A61P 25/28* (2018.01); *A61K 38/00* (2013.01); *C07K 2319/07* (2013.01); *C07K 2319/10* (2013.01); *C07K 2319/21* (2013.01)

(58) Field of Classification Search
CPC ............... A61K 38/1709; C07K 14/47; C07K 2319/07; C07K 2319/10
See application file for complete search history.

(56) References Cited

U.S. PATENT DOCUMENTS 11,459,363 B2 10/2022 Payne
2014/0135275 A1* 5/2014 Keefe .................... C07K 14/47
435/375
(Continued)

FOREIGN PATENT DOCUMENTS

WO 2012/174452 A1 12/2012
WO 2013/071440 A1 5/2013
(Continued)

OTHER PUBLICATIONS

International Search Report and Written Opinion issued by the EPO acting as the International Searching Authority, dated Oct. 28, 2020, for International Patent Application No. PCT/US2020/044069; 17 pages.
(Continued)

*Primary Examiner* — Jeffrey E. Russel
(74) *Attorney, Agent, or Firm* — Faegre Drinker Biddle & Reath LLP

(57) ABSTRACT

A TAT-FXN fusion polypeptide useful in treating subjects diagnosed with Friedrich's Ataxia, hypertrophic cardiomyopathy, or both are disclosed, as are related methods of treatment and pharmaceutical compositions.

18 Claims, 20 Drawing Sheets

Specification includes a Sequence Listing.

TAT-FXN Amino Acid Sequence:

```
MYGRKKRRQR RRGGMWTLGR RAVAGLLASP SPAQAQTLTR VPRPAELAPL   50
CGRRGLRTDI DATCTPRRAS SNQRGLNQIW NVKKQSVYLM NLRKSGTLGH  100
PGSLDETTYE RLAEETLDSL AEFFEDLADK PYTFEDYDVS FGSGVLTVKL  150
GGDLGTYVIN KQTPNKQIWL SSPSSGPKRY DWTGKNWVYS HDGVSLHELL  200
AAELTKALKT KLDLSSLAYS GKDA                             224
```

*Note: Gly-Gly linker is underlined; TAT-cpp is upstream of the Gly-Gly linker; mature hFXN is located downstream of the Gly-Gly linker.*

(51) Int. Cl.
*C07K 14/47* (2006.01)
*A61K 38/00* (2006.01)

(56) References Cited

U.S. PATENT DOCUMENTS

| | | |
|---|---|---|
| 2014/0308262 A1 | 10/2014 | Lorberboum-Galski |
| 2017/0327847 A1 | 11/2017 | Ghadessy et al. |
| 2020/0377951 A1 | 12/2020 | Bettoun |
| 2021/0047378 A1 | 2/2021 | Payne |
| 2021/0355177 A1 | 11/2021 | Bettoun et al. |
| 2021/0363205 A1 | 11/2021 | Bettoun |

FOREIGN PATENT DOCUMENTS

| | | |
|---|---|---|
| WO | 2016/172659 A1 | 10/2016 |
| WO | 2021/011929 A1 | 1/2021 |

OTHER PUBLICATIONS

PM. Vyas et al. "A TAT-Frataxin fusion protein increases lifespan and cardiac function in a conditional Friedreich's ataxia mouse model", Human Molecular Genetics, vol. 21, No. 6, Nov. 23, 2011; 18 pages.

International Preliminary Report on Patentability received for PCT Patent Application No. PCT/US2020/044069, mailed on Feb. 10, 2022, 9 pages.

\* cited by examiner

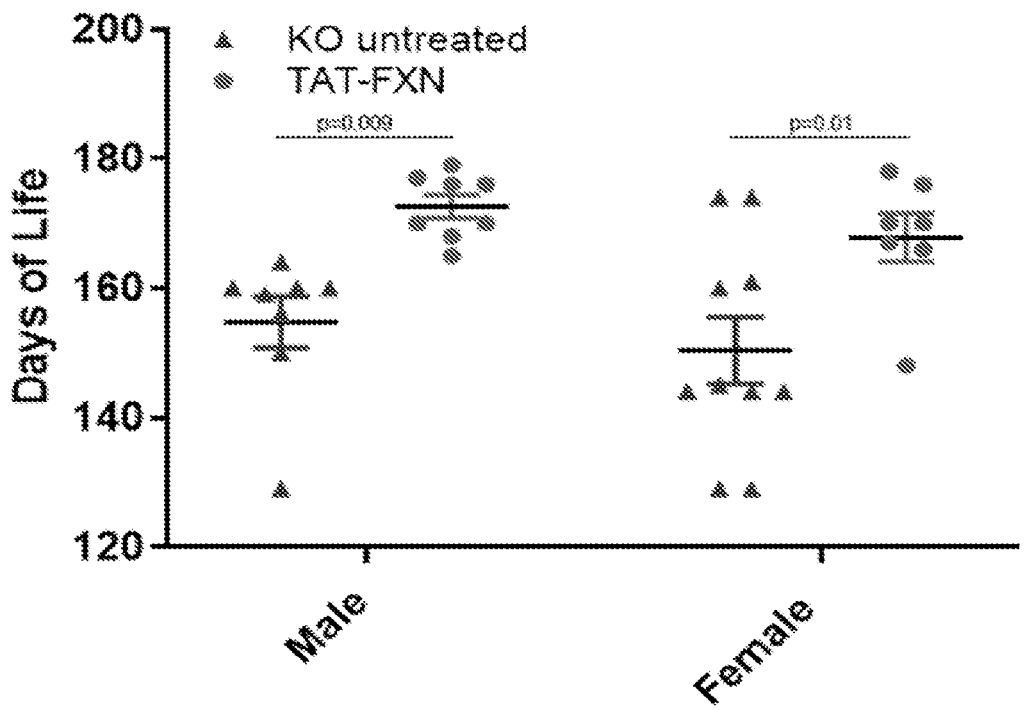

FIG. 4

TAT-FXN Amino Acid Sequence:

```
MYGRKKRRQR  RRGGMWTLGR  RAVAGLLASP  SPAQAQTLTR  VPRPAELAPL   50
CGRRGLRTDI  DATCTPRRAS  SNQRGLNQIW  NVKKQSVYLM  NLRKSGTLGH  100
PGSLDETTYE  RLAEETLDSL  AEFFEDLADK  PYTFEDYDVS  FGSGVLTVKL  150
GGDLGTYVIN  KQTPNKQIWL  SSPSSGPKRY  DWTGKNWVYS  HDGVSLHELL  200
AAELTKALKT  KLDLSSLAYS  GKDA                                224
```

*Note: Gly-Gly linker is underlined; TAT-cpp is upstream of the Gly-Gly linker; mature hFXN is located downstream of the Gly-Gly linker.*

FIG. 5

| Brain Vehicle Dose FXN Concentration (pg/mL) | |
|---|---|
| 2398 LH | 0 |
| 2491 RF | 0 |
| 2490 RF | 0 |
| 2734 RR | 0 |

| Spinal Cord Vehicle Dose FXN Concentration (pg/mL) | |
|---|---|
| 2389 RR | 0 |
| 2389 LF | 0 |
| 2420 LL | 0 |
| 2432 HH | 0 |

| DRG Vehicle Dose FXN Concentration (pg/mL) | |
|---|---|
| 2420 LL | 0 |
| 2432 HH | 0 |
| 2389 LF | 0 |
| 2839 RR | 0 |

FIG. 7C

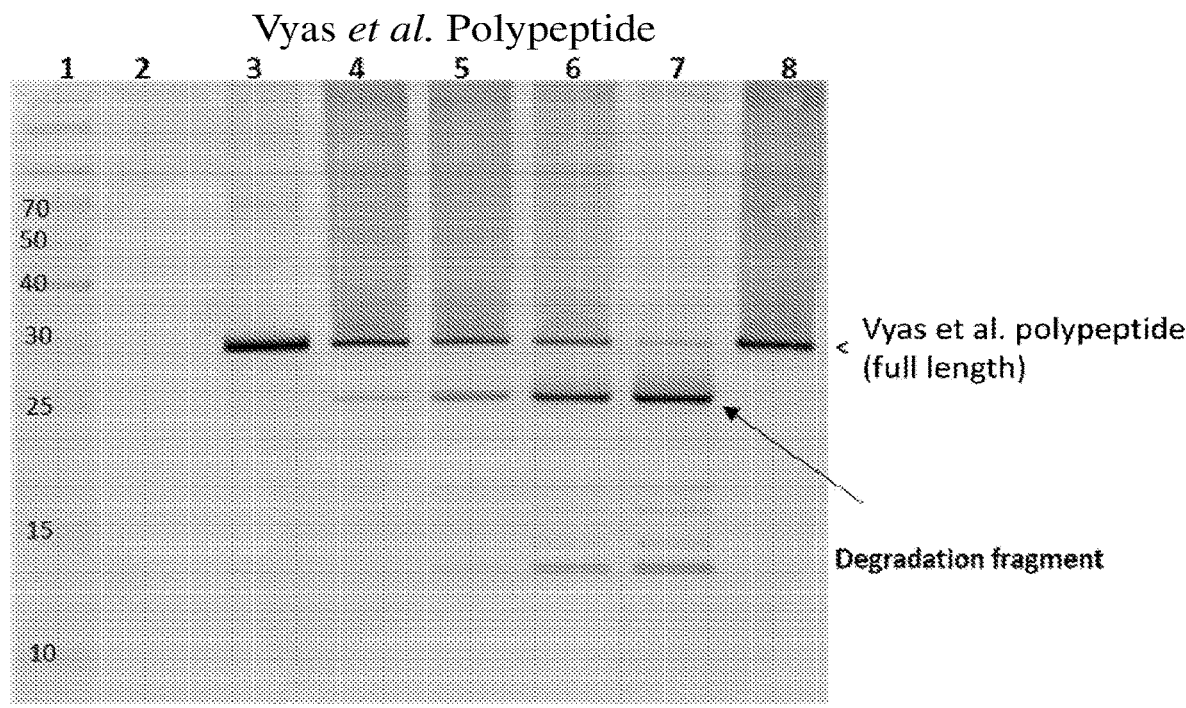

| Lane No. | Sample Description |
|---|---|
| 1 | Molecular Weight Markers (kDA) |
| 2 | 15% Human Plasma (hP) diluted in PBS |
| 3 | Vyas *et al.* polypeptide in 15% hP, incubated for 0.5 hours |
| 4 | Vyas *et al.* fusion polypeptide in 15% hP, incubated for 1 hours |
| 5 | Vyas *et al.* fusion polypeptide in 15% hP, incubated for 2 hours |
| 6 | Vyas *et al.* fusion polypeptide in 15% hP, incubated for 3 hours |
| 7 | Vyas *et al.* fusion polypeptide in 15% hP, incubated for 4 hours |
| 8 | Vyas *et al.* fusion polypeptide in 15% hP, incubated for 4 hours with a protease inhibitor |

FIG. 12B

TAT-FXN fusion polypeptide  Vyas *et al.* polypeptide
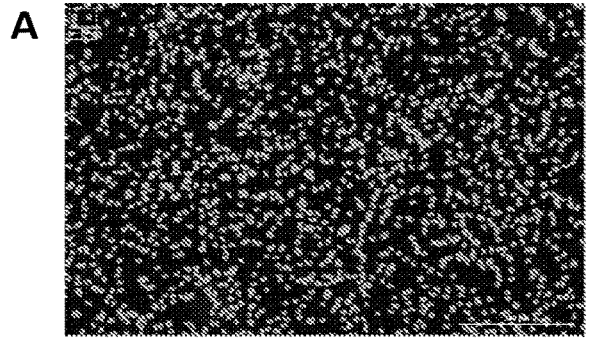
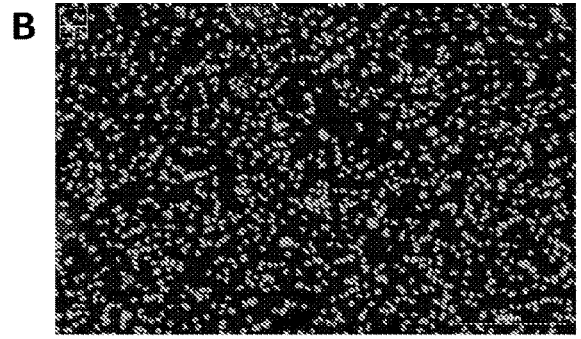
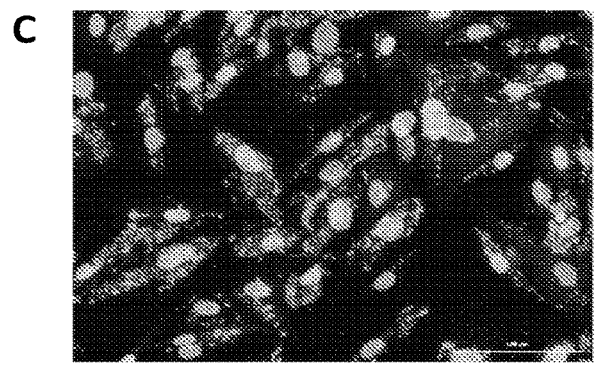
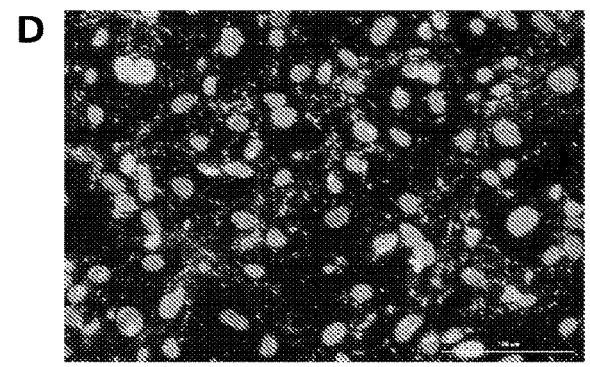
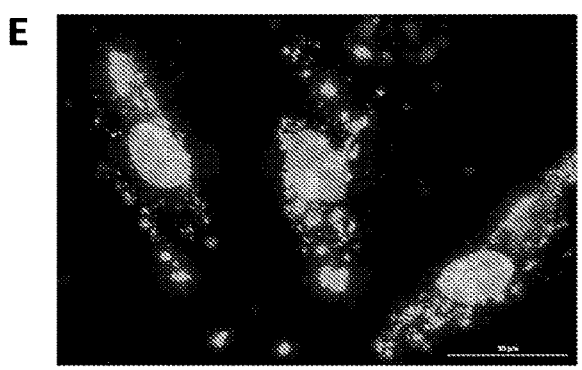
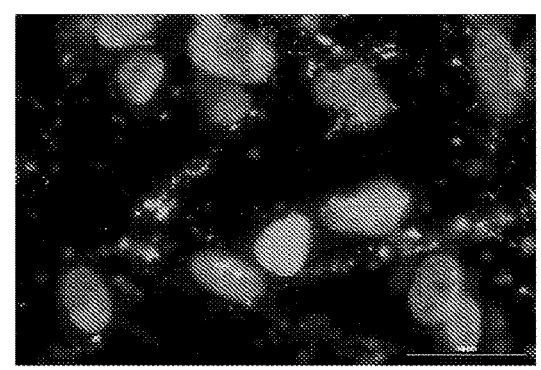
FIG. 13A

MATERIALS AND METHODS FOR TREATING Friedreich's Ataxia

This application is a continuation of U.S. patent application Ser. No. 16/942,276, filed on Jul. 29, 2020, now U.S. Pat. No. 11,459,363, issued on Oct. 4, 2022; which claims priority under 35 U.S.C. § 119 (e) to U.S. Provisional Application Ser. No. 62/880,073, filed on Jul. 29, 2019 and U.S. Provisional Application Ser. No. 62/891,029, filed on Aug. 23, 2019. The entire contents of each of the foregoing applications are hereby incorporated herein by reference.

SEQUENCE LISTING

The instant application contains a Sequence Listing which has been submitted electronically in XML format and is hereby incorporated by reference in its entirety. Said XML copy, created on Apr. 21, 2023, is named IU-2019-109-13-US_346233_1399 SL.xml and is 14,779 bytes in size.

FIELD

The present disclosure relates generally to treating Friedreich's Ataxia with a TAT-FXN fusion polypeptide and/or formulations of that polypeptide.

BACKGROUND

Friedreich's Ataxia (FRDA) is a progressive neurodegenerative movement disorder, with a typical age of onset between 10 and 15 years. It is a genetic disorder, representing one of the most commonly inherited ataxias in humans. FRDA is also incredibly rare; in the US alone there are only about 4,000-5,000 confirmed cases. Patients suffering from FRDA exhibit multiple symptoms. Initial symptoms include unsteady posture and frequent falling, both associated with a progressive difficulty in walking. A hallmark presentation of the disease includes progressive limb ataxia and dysarthria. As the disease progresses, patients experience progressive neurological and cardiac dysfunction. It is common for patients with FRDA to develop cardiomyopathy, which can lead to heart failure and/or cardiac arrhythmias Hypertrophic cardiomyopathy is associated with early mortality in the $3^{rd}$ to $5^{th}$ decades of life for FRDA patients. Other clinical presentations include scoliosis, fatigue, diabetes, visual impairment, and hearing loss.

There is currently no cure for FRDA. Existing treatments are symptomatic in nature, focusing on treating the heart problems or diabetes caused by the gene defect. A Transactivator of Transcription-frataxin (TAT-FXN) fusion polypeptide has previously been described [see Vyas, et al., *Hum. Mol. Genet.*, v21 n6, 1230-1247 (2012)] as capable of delivering a functional mitochondrial protein in vivo to rescue the FRDA disease phenotype and thus serve as a possible protein replacement therapy. However, the therapeutic efficacy of the fusion polypeptide disclosed by Vyas et al. is limited by its poor solubility a physiological pH.

There is thus a strong need for the development of new therapies to treat FRDA.

SUMMARY

The present disclosure provides TAT-FXN fusion polypeptides, compositions comprising the TAT-FXN fusion polypeptides, and methods of use of the TAT-FXN fusion polypeptides to treat FRDA. In particular, the present disclosure provides a new TAT-FXN fusion polypeptide, never-before described, that overcomes the deficiencies present in the TAT-FXN fusion polypeptide previously described by Vyas et al. (supra), as well as advantageous compositions comprising the new TAT-FXN fusion polypeptide.

A disclosed TAT-FXN fusion polypeptide is characterized as unexpectedly having a significantly higher solubility (e.g., solubility in an aqueous solution) than the Vyas et al. polypeptide. For example, it is possible to prepare compositions (e.g., aqueous compositions) comprising the disclosed TAT-FXN fusion polypeptide at concentrations greater than 50 mg/mL. In contrast, the Vyas et al. polypeptide cannot exceed about 2 mg/mL before it begins to precipitate out of solution. Accordingly, the TAT-FXN fusion polypeptide provided by the present disclosure allows preparation of a pharmaceutical composition comprising the polypeptide at a concentration at or greater than 2 mg/mL. Such a pharmaceutical composition provides the significant advantage of allowing administration of far higher doses of the disclosed TAT-FXN fusion polypeptide than was previously possible (e.g., by subcutaneous injection).

Accordingly, the present disclosure provides a fusion polypeptide, comprising: a first peptide having an amino acid sequence with at least about 90% sequence identity to the amino acid sequence of SEQ ID NO: 2 or SEQ ID NO: 7; a second peptide having an amino acid sequence with at least about 90% sequence identity to the amino acid sequence of SEQ ID NO: 4; and a linker of 1, 2 or 3 amino acids disposed between the first and second peptides.

In some embodiments, the first peptide has an amino acid sequence with at least about 95% sequence identity to the amino acid sequence of SEQ ID NO: 2 or SEQ ID NO: 7. In some embodiments, the first peptide has the amino acid sequence of SEQ ID NO: 2 or SEQ ID NO: 7.

In some embodiments, the second peptide has an amino acid sequence with at least about 95% sequence identity to the amino acid sequence of SEQ ID NO: 4. In some embodiments, the second peptide has the amino acid sequence of SEQ ID NO: 4.

In some embodiments, the linker is a 2-amino acid linker. In some embodiments, the 2-amino acid linker is Gly-Gly.

In some embodiments, the sequence of the fusion polypeptide, beginning at the N-terminus is: the first peptide, followed by the linker, followed by the second peptide. In some embodiments, the sequence of the fusion polypeptide, beginning at the N-terminus, is: the second peptide, followed by the linker, followed by the first peptide.

In some embodiments, the fusion polypeptide comprises an amino acid sequence with at least about 90% sequence identity to the amino acid sequence of SEQ ID NO: 1.

In some embodiments, the fusion polypeptide comprises an amino acid sequence with at least about 95% sequence identity to the amino acid sequence of SEQ ID NO: 1. In some embodiments, the fusion polypeptide comprises the amino acid sequence of SEQ ID NO: 1.

In some embodiments, the fusion polypeptide consists of: a first peptide having an amino acid sequence with at least about 90% sequence identity to the amino acid sequence of SEQ ID NO: 2 or SEQ ID NO: 7; a second peptide having an amino acid sequence with at least about 90% sequence identity to the amino acid sequence of SEQ ID NO: 4; and a linker of 1, 2 or 3 amino acids disposed between the first and second peptides.

In some embodiments, the first peptide has an amino acid sequence with at least about 95% sequence identity to the amino acid sequence of SEQ ID NO: 2 or SEQ ID NO: 7. In some embodiments, the first peptide has the amino acid sequence of SEQ ID NO: 2 or SEQ ID NO: 7.

In some embodiments, the second peptide has an amino acid sequence with at least about 95% sequence identity to the amino acid sequence of SEQ ID NO: 4. In some embodiments, the second peptide has the amino acid sequence of SEQ ID NO: 4.

In some embodiments, the linker is a 2-amino acid linker. In some embodiments, the 2-amino acid linker is Gly-Gly.

In some embodiments, the sequence of the fusion polypeptide, beginning at the N-terminus is: the first peptide, followed by the linker, followed by the second peptide. In some embodiments, the sequence of the fusion polypeptide, beginning at the N-terminus, is: the second peptide, followed by the linker, followed by the first peptide.

The present disclosure also provides a fusion polypeptide consisting of: a first peptide having an amino acid sequence with at least about 90% sequence identity to the amino acid sequence of SEQ ID NO: 2 or SEQ ID NO: 7; a second peptide having an amino acid sequence with at least about 90% sequence identity to the amino acid sequence of SEQ ID NO: 4; and a linker of 1, 2 or 3 amino acids disposed between the first and second peptides.

In some embodiments, the first peptide has an amino acid sequence with at least about 95% sequence identity to the amino acid sequence of SEQ ID NO: 2 or SEQ ID NO: 7. In some embodiments, the first peptide has the amino acid sequence of SEQ ID NO: 2 or SEQ ID NO: 7.

In some embodiments, the second peptide has an amino acid sequence with at least about 95% sequence identity to the amino acid sequence of SEQ ID NO: 4. In some embodiments, the second peptide has the amino acid sequence of SEQ ID NO: 4.

In some embodiments, the linker is a 2-amino acid linker. In some embodiments, the 2-amino acid linker is Gly-Gly.

In some embodiments, the sequence of the fusion polypeptide, beginning at the N-terminus is: the first peptide, followed by the linker, followed by the second peptide. In some embodiments, the sequence of the fusion polypeptide, beginning at the N-terminus, is: the second peptide, followed by the linker, followed by the first peptide.

The present disclosure also provides a fusion polypeptide, comprising: a first peptide having an amino acid sequence with at least about 90% sequence identity to the amino acid sequence of SEQ ID NO: 2 or SEQ ID NO: 7; a second peptide having an amino acid sequence with at least about 90% sequence identity to the amino acid sequence of SEQ ID NO: 3; a third peptide having an amino acid sequence with at least about 90% sequence identity to the amino acid sequence of SEQ ID NO: 5; and a linker of 1, 2 or 3 amino acids disposed between the first and second peptides.

In some embodiments, the first peptide has an amino acid sequence with at least about 95% sequence identity to the amino acid sequence of SEQ ID NO: 2 or SEQ ID NO: 7. In some embodiments, the first peptide has the amino acid sequence of SEQ ID NO: 2 or SEQ ID NO: 7.

In some embodiments, the second peptide has an amino acid sequence with at least about 95% sequence identity to the amino acid sequence of SEQ ID NO: 3. In some embodiments, the second peptide has the amino acid sequence of SEQ ID NO: 3.

In some embodiments, the third peptide has an amino acid sequence with at least about 95% sequence identity to the amino acid sequence of SEQ ID NO: 5. In some embodiments, the third peptide has the amino acid sequence of SEQ ID NO: 5.

In some embodiments, the linker is a 2-amino acid linker. In some embodiments, the 2-amino acid linker is Gly-Gly.

In some embodiments, the sequence of the fusion polypeptide, beginning at the N-terminus is: the first peptide, followed by the linker, followed by the second peptide, followed by the third peptide. In some embodiments, the sequence of the fusion polypeptide, beginning at the N-terminus, is: the second peptide, followed by the third peptide, followed by the linker, followed by the first peptide.

In some embodiments, the fusion polypeptide consists of: a first peptide having an amino acid sequence with at least about 90% sequence identity to the amino acid sequence of SEQ ID NO: 2 or SEQ ID NO: 7; a second peptide having an amino acid sequence with at least about 90% sequence identity to the amino acid sequence of SEQ ID NO: 3; a third peptide having an amino acid sequence with at least about 90% sequence identity to the amino acid sequence of SEQ ID NO: 5; and a linker of 1, 2 or 3 amino acids disposed between the first and second peptides.

In some embodiments, the first peptide has an amino acid sequence with at least about 95% sequence identity to the amino acid sequence of SEQ ID NO: 2 or SEQ ID NO: 7. In some embodiments, the first peptide has the amino acid sequence of SEQ ID NO: 2 or SEQ ID NO: 7.

In some embodiments, the second peptide has an amino acid sequence with at least about 95% sequence identity to the amino acid sequence of SEQ ID NO: 3. In some embodiments, the second peptide has the amino acid sequence of SEQ ID NO: 3.

In some embodiments, the third peptide has an amino acid sequence with at least about 95% sequence identity to the amino acid sequence of SEQ ID NO: 5. In some embodiments, the third peptide has the amino acid sequence of SEQ ID NO: 5.

In some embodiments, the linker is a 2-amino acid linker. In some embodiments, the 2-amino acid linker is Gly-Gly.

In some embodiments, the sequence of the fusion polypeptide, beginning at the N-terminus is: the first peptide, followed by the linker, followed by the second peptide, followed by the third peptide. In some embodiments, the sequence of the fusion polypeptide, beginning at the N-terminus is: the second peptide, followed by the third peptide, followed by the linker, followed by the first peptide.

The present disclosure also provides a fusion polypeptide consisting of: a first peptide having an amino acid sequence with at least about 90% sequence identity to the amino acid sequence of SEQ ID NO: 2 or SEQ ID NO: 7; a second peptide having an amino acid sequence with at least about 90% sequence identity to the amino acid sequence of SEQ ID NO: 3; a third peptide having an amino acid sequence with at least about 90% sequence identity to the amino acid sequence of SEQ ID NO: 5; and a linker of 1, 2 or 3 amino acids disposed between the first and second peptides.

In some embodiments, the first peptide has an amino acid sequence with at least about 95% sequence identity to the amino acid sequence of SEQ ID NO: 2 or SEQ ID NO: 7. In some embodiments, the first peptide has the amino acid sequence of SEQ ID NO: 2 or SEQ ID NO: 7.

In some embodiments, the second peptide has an amino acid sequence with at least about 95% sequence identity to the amino acid sequence of SEQ ID NO: 3. In some embodiments, the second peptide has the amino acid sequence of SEQ ID NO: 3.

In some embodiments, the third peptide has an amino acid sequence with at least about 95% sequence identity to the amino acid sequence of SEQ ID NO: 5. In some embodiments, the third peptide has the amino acid sequence of SEQ ID NO: 5.

In some embodiments, the linker is a 2-amino acid linker. In some embodiments, the 2-amino acid linker is Gly-Gly.

In some embodiments, the sequence of the fusion polypeptide, beginning at the N-terminus is: the first peptide, followed by the linker, followed by the second peptide, followed by the third peptide. In some embodiments, the sequence of the fusion polypeptide, beginning at the N-terminus is: the second peptide, followed by the third peptide, followed by the linker, followed by the third peptide.

The present disclosure provides a fusion polypeptide comprising the amino acid sequence of SEQ ID NO: 1. In some embodiments, the fusion polypeptide consists of the amino acid sequence of SEQ ID NO: 1.

The present disclosure provides a fusion polypeptide, consisting of: a first peptide having an amino acid sequence with at least about 90% sequence identity to the amino acid sequence of SEQ ID NO: 2 or SEQ ID NO: 7; and a second peptide having an amino acid sequence with at least about 90% sequence identity to the amino acid sequence of SEQ ID NO: 4.

In some embodiments, the first peptide has an amino acid sequence with at least about 95% sequence identity to the amino acid sequence of SEQ ID NO: 2 or SEQ ID NO: 7. In some embodiments, the first peptide has the amino acid sequence of SEQ ID NO: 2 or SEQ ID NO: 7.

In some embodiments, the second peptide has an amino acid sequence with at least about 95% sequence identity to the amino acid sequence of SEQ ID NO: 4. In some embodiments, the second peptide has the amino acid sequence of SEQ ID NO: 4.

In some embodiments, the sequence of the fusion polypeptide, beginning at the N-terminus is: the first peptide, followed by the second peptide. In some embodiments, the sequence of the fusion polypeptide, beginning at the N-terminus, is: the second peptide, followed by the first peptide.

The present disclosure also provides a fusion polypeptide, consisting of: a first peptide having an amino acid sequence with at least about 90% sequence identity to the amino acid sequence of SEQ ID NO: 2 or SEQ ID NO: 7; a second peptide having an amino acid sequence with at least about 90% sequence identity to the amino acid sequence of SEQ ID NO: 3; and a third peptide having an amino acid sequence with at least about 90% sequence identity to the amino acid sequence of SEQ ID NO: 5.

In some embodiments, the first peptide has an amino acid sequence with at least about 95% sequence identity to the amino acid sequence of SEQ ID NO: 2 or SEQ ID NO: 7. In some embodiments, the first peptide has the amino acid sequence of SEQ ID NO: 2 or SEQ ID NO: 7.

In some embodiments, the second peptide has an amino acid sequence with at least about 95% sequence identity to the amino acid sequence of SEQ ID NO: 3. In some embodiments, the second peptide has the amino acid sequence of SEQ ID NO: 3.

In some embodiments, the third peptide has an amino acid sequence with at least about 95% sequence identity to the amino acid sequence of SEQ ID NO: 5. In some embodiments, the third peptide has the amino acid sequence of SEQ ID NO: 5.

In some embodiments, the sequence of the fusion polypeptide, beginning at the N-terminus is: the first peptide, followed by the second peptide, followed by the third peptide. In some embodiments, the sequence of the fusion polypeptide, beginning at the N-terminus, is: the second peptide, followed by the third peptide, followed by the first peptide.

The present disclosure also provides a nucleic acid sequence encoding the fusion polypeptide. In some embodiments, the nucleic acid sequence is codon optimized. In some embodiments, the nucleic acid sequence of SEQ ID NO: 6.

The present disclosure provides an expression cassette comprising the nucleic acid sequence of the disclosure and a promoter operably linked to said nucleic acid sequence.

The present disclosure provides an expression vector comprising the disclosed expression cassette.

The present disclosure provides a host cell comprising the expression vector of the disclosure. In some embodiments, the host cell is a bacterial cell. In some embodiments, the bacterial cell is an *E. coli* cell.

The present disclosure provides a pharmaceutical composition comprising the fusion polypeptide of the disclosure and a pharmaceutically acceptable carrier.

The present disclosure provides a pharmaceutical composition comprising a fusion polypeptide and a pharmaceutically acceptable carrier, wherein the fusion polypeptide is present in the pharmaceutical composition at a concentration of greater than about 4 mg/mL; and wherein the fusion polypeptide comprises: a first peptide having an amino acid sequence with at least about 90% sequence identity to the amino acid sequence of SEQ ID NO: 2 or SEQ ID NO: 7; and a second peptide having an amino acid sequence with at least about 90% sequence identity to the amino acid sequence of SEQ ID NO: 4.

In some embodiments, the first peptide has an amino acid sequence with at least about 95% sequence identity to the amino acid sequence of SEQ ID NO: 2 or SEQ ID NO: 7. In some embodiments, the first peptide has the amino acid sequence of SEQ ID NO: 2 or SEQ ID NO: 7.

In some embodiments, the second peptide has an amino acid sequence with at least about 95% sequence identity to the amino acid sequence of SEQ ID NO: 4. In some embodiments, the second peptide has the amino acid sequence of SEQ ID NO: 4.

The present disclosure provides a pharmaceutical composition comprising a fusion polypeptide and a pharmaceutically acceptable carrier, wherein the fusion polypeptide is present in the pharmaceutical composition at a concentration of greater than about 4 mg/mL and wherein the fusion polypeptide comprises: a first peptide having an amino acid sequence with at least about 90% sequence identity to the amino acid sequence of SEQ ID NO: 2 or SEQ ID NO: 7; a second peptide having an amino acid sequence with at least about 90% sequence identity to the amino acid sequence of SEQ ID NO: 3; and a third peptide having an amino acid sequence with at least about 90% sequence identity to the amino acid sequence of SEQ ID NO: 5.

In some embodiments, the first peptide has an amino acid sequence with at least about 95% sequence identity to the amino acid sequence of SEQ ID NO: 2 or SEQ ID NO: 7. In some embodiments, the first peptide has the amino acid sequence of SEQ ID NO: 2 or SEQ ID NO: 7.

In some embodiments, the second peptide has an amino acid sequence with at least about 95% sequence identity to the amino acid sequence of SEQ ID NO: 3. In some embodiments, the second peptide has the amino acid sequence of SEQ ID NO: 3.

In some embodiments, the third peptide has an amino acid sequence with at least about 95% sequence identity to the amino acid sequence of SEQ ID NO: 5. In some embodiments, the third peptide has the amino acid sequence of SEQ ID NO: 5.

In some embodiments, the fusion polypeptide further comprises a linker of 1, 2 or 3 amino acids disposed between the first and second peptides. In some embodiments, the linker is a 2-amino acid linker. In some embodiments, the 2-amino acid linker is Gly-Gly.

In some embodiments, the fusion polypeptide is present in the pharmaceutical composition of the disclosure at a concentration of about 5 mg/mL to about 50 mg/mL, about 20 mg/mL to about 75 mg/mL or about 25 mg/mL to about 100 mg/mL. In some embodiments, the fusion polypeptide is present in said pharmaceutical composition at a concentration of greater than about 5 mg/mL, greater than about 10 mg/mL, greater than about 15 mg/mL, greater than about 20 mg/mL, greater than about 25 mg/mL, greater than about 30 mg/mL, greater than about 35 mg/mL, greater than about 40 mg/mL or greater than about 45 mg/mL. In some embodiments, the fusion polypeptide is present in said pharmaceutical composition at a concentration of about 50 mg/mL.

In some embodiments, the pharmaceutical composition of the disclosure is injectable. In some embodiments, the pharmaceutical composition is suitable for subcutaneous injection.

The present disclosure provides a method of treating Friedreich's Ataxia (FRDA), the method comprising administering to a subject in need thereof the fusion polypeptide of the disclosure or the pharmaceutical composition of the disclosure.

The present disclosure provides a method of treating an FRDA-associated disease, said method comprising administering to a subject in need thereof the fusion polypeptide of the disclosure or the pharmaceutical composition of the disclosure. In some embodiments, the FRDA-associated disease is selected from the group consisting of FRDA-associated pneumonia, FRDA-associated hypertrophic cardiomyopathy, and FRDA-associated diabetes.

The present disclosure also provides a method of treating an FRDA-associated disease, the method comprising administering to a subject in need thereof the fusion polypeptide of the disclosure or the pharmaceutical composition of the disclosure. In some embodiments, the FRDA-associated disease is selected from the group consisting of loss of proprioception, loss of reflexes, loss of ability to walk, loss of ability to hold gaze with eyes, impaired swallowing, progressive loss of hearing, progressive loss of vision, progressive loss of speech, elevated triglycerides, low HDL cholesterol, elevated LDL cholesterol, scoliosis and combinations thereof.

In some embodiments, the fusion polypeptide or said pharmaceutical composition is administered subcutaneously.

In some embodiments, the fusion polypeptide is administered in an amount of greater than 2 mg/injection.

In some embodiments, the fusion polypeptide is administered in an amount of about 2.5 mg/injection to about 10 mg/injection, about 5 mg/injection to about 50 mg/injection, about 20 mg/injection to about 75 mg/injection, about 25 mg/injection to about 100 mg/injection and about 100 mg/injection to about 150 mg/injection. In some embodiments, the fusion polypeptide is administered at a dose of about 10-mg to about 150 mg. In some embodiments, the fusion polypeptide is administered at a dose of about 10 mg to about 30 mg, about 20 mg to about 75 mg or about 50 mg to about 100 mg. In some embodiments, the fusion polypeptide is administered at a dose of about 25 mg, about 50 mg, about 75 mg or about 100 mg.

In some embodiments, the fusion polypeptide is administered at a dose of about 5 mg kg$^{-1}$ to 60 mg kg$^{-1}$ per day.

The present disclosure also provides the fusion polypeptide of the disclosure or the pharmaceutical composition of the disclosure for use in a method of treating Friedreich's Ataxia (FRDA), FRDA-associated hypertrophic cardiomyopathy, an FRDA-associated disease, or a combination thereof in a subject in need thereof, wherein the method comprises administering a therapeutically effective amount of the fusion polypeptide or pharmaceutical composition to a subject in need thereof, wherein the FRDA-associated disease is selected from the group of conditions consisting of: loss of proprioception, loss of reflexes, loss of ability to walk, loss of ability to hold gaze with eyes, impaired swallowing, progressive loss of hearing, progressive loss of vision, progressive loss of speech, elevated triglycerides, low HDL cholesterol, elevated LDL cholesterol, scoliosis, and combinations thereof.

In some embodiments, the method comprises administering the fusion polypeptide in an amount:
(i) of about 5 mg kg$^{-1}$-60 mg kg$^{-1}$ per day;
(ii) selected from: about 10 mg kg$^{-1}$-50 mg kg$^{-1}$ per day, about 20 mg kg$^{-1}$-40 mg kg$^{-1}$ per day, about 30 mg kg$^{-1}$-40 mg kg$^{-1}$ per day, about 40 mg kg$^{-1}$-50 mg kg$^{-1}$ per day, about 50 mg kg$_{-1}$-60 mg kg$^{-1}$ per day, about 5 mg kg$^{-1}$-10 mg kg$^{-1}$ per day, about 10 mg kg$^{-1}$-15 mg kg$^{-1}$ per day, about 15 mg kg$^{-1}$-20 mg kg$^{-1}$ per day, about 20 mg kg$^{-1}$-25 mg kg$^{-1}$ per day, about 25 mg kg$^{-1}$-30 mg kg$^{-1}$ per day, about 30 mg kg$^{-1}$-35 mg kg$^{-1}$ per day, about 35 mg kg$^{-1}$-40 mg kg$^{-1}$ per day, about 40 mg kg$^{-1}$-45 mg kg$^{-1}$ per day, about 45 mg kg$^{-1}$-50 mg kg$^{-1}$ per day, about 50 mg kg$^{-1}$-55 mg kg$^{-1}$ per day, and about 55 mg kg$^{-1}$-60 mg kg$^{-1}$ per day;
(iii) greater than or equal to 2 mg/injection;
(iv) selected from about 2.5 mg/injection-about 10 mg/injection, about 5 mg/injection-about 50 mg/injection, about 20 mg/injection-about 75 mg/injection, about 25 mg/injection-about 100 mg/injection, and about 100 mg/injection-about 150 mg/injection; or (v) selected from about 2.5 mg/injection-about 5 mg/injection, about 4 mg/injection-about 10 mg/injection, about 5 mg/injection-about 25 mg/injection, about 15 mg/injection-about 30 mg/injection, about 20 mg/injection-about 50 mg/injection, about 25 mg/injection-about 60 mg/injection, about 35 mg/injection-about 75 mg/injection, about 50 mg/injection-about 80 mg/injection, about 90 mg/injection-about 120 mg/injection, and about 100 mg/injection-about 150 mg/injection.

In some embodiments, the fusion polypeptide or the pharmaceutical composition is administered by subcutaneous injection.

The present disclosure also provides the fusion polypeptide of the disclosure for use in the manufacture of a medicament for the treatment of Friedreich's Ataxia (FRDA), FRDA-associated hypertrophic cardiomyopathy, an FRDA-associated disease, or a combination thereof of a subject in need thereof, wherein the medicament further comprises a pharmaceutically acceptable vehicle and a pharmaceutically acceptable excipient, wherein the FRDA-associated disease is selected from the group of conditions consisting of: loss of proprioception, loss of reflexes, loss of ability to walk, loss of ability to hold gaze with eyes, impaired swallowing, progressive loss of hearing, progressive loss of vision, progressive loss of speech, elevated triglycerides, low HDL cholesterol, elevated LDL cholesterol, scoliosis, and combinations thereof.

In some embodiments, the fusion polypeptide is included in the pharmaceutical composition in an amount of:
(i) about 10-100 mg/ml, about 10-50 mg/ml, about 10 mg/ml, or about 50 mg/ml;
(ii) greater than or equal to 2 mg/ml;
(iii) about 2.5 mg/mL-about 10 mg/mL, about 5 mg/mL-about 50 mg/mL, about 20 mg/mL-about 75 mg/mL, or about 25 mg/mL-about 100 mg/mL; or
(iv) about 2.5 mg/mL-about 5 mg/mL, about 4 mg/mL-about 10 mg/mL, about 5 mg/mL-about 25 mg/mL, about 15 mg/mL-about 30 mg/mL, about 20 mg/mL-about 50 mg/mL, about 25 mg/mL-about 60 mg/mL, about 35 mg/mL-about 75 mg/mL, about 50 mg/mL-about 80 mg/mL, or about 90 mg/mL-about 100 mg/mL In some embodiments, the pharmaceutically acceptable vehicle is selected from the group consisting of: from water, saline solution, sodium acetate, acetic acid-sodium acetate buffer, phosphate-buffered saline, an oil emulsion, and combinations of the foregoing. In some embodiments, the pharmaceutically acceptable vehicle is sodium acetate.

In some embodiments, the pharmaceutically acceptable vehicle is included in the pharmaceutical composition at a concentration of about 50 mM.

In some embodiments, the pharmaceutically acceptable excipient is propylene glycol.

In some embodiments, the pharmaceutically acceptable excipient is included in the pharmaceutical composition in an amount of about 1% of the total volume of the composition.

In some embodiments, the pH of the composition is about 5 to about 7. In some embodiments, the pH of the composition is about 5.

In some embodiments, the medicament is injectable. In some embodiments, the medicament is suitable for subcutaneous injection.

A TAT-FXN fusion polypeptide having the amino acid sequence of SEQ ID NO: 1 is provided. The TAT portion of the disclosed fusion polypeptide can have the amino acid sequence of SEQ ID NO: 2, the FXN portion of the fusion polypeptide has the amino acid sequence of SEQ ID NO: 4, and a linker situated between the TAT portion and the FXN portion of the fusion polypeptide is Gly-Gly.

A pharmaceutical composition is provided, comprising a TAT-FXN fusion polypeptide that can have the amino acid sequence of SEQ ID NO: 1, a pharmaceutically acceptable vehicle, and a pharmaceutically acceptable excipient, wherein, in some embodiments, the TAT portion of the fusion polypeptide has the amino acid sequence of SEQ ID NO: 2, the FXN portion of the fusion polypeptide has the amino acid sequence of SEQ ID NO: 4, and a linker situated between the TAT portion and the FXN portion of the fusion polypeptide can be Gly-Gly.

The TAT-FXN fusion polypeptide can be present in the pharmaceutical composition in an amount selected from about 10-100 mg/ml, about 10-50 mg/ml, about 10 mg/ml and about 50 mg/ml. The TAT-FXN fusion polypeptide can be present in the pharmaceutical composition in an amount of about 50 mg/ml.

The pharmaceutically acceptable in the pharmaceutical composition vehicle can vary. A pharmaceutically acceptable vehicle can be water, saline solution, sodium acetate, acetic acid-sodium acetate buffer, phosphate-buffered saline, an oil emulsion, and combinations thereof. In one embodiment, the pharmaceutically acceptable vehicle is sodium acetate. In any and/or all of the foregoing embodiments, the pharmaceutically acceptable vehicle is at a concentration of 50 mM.

A pharmaceutically acceptable excipient can be, for example, propylene glycol and which can be present in the pharmaceutical composition in an amount of 1% of the total volume of the composition.

The pH of the pharmaceutical composition can vary. In some embodiments, the pH of the composition is about 5-7. In particular embodiments, the pH of the composition can be about 5. In another formulation, the pH is around 7, or physiological pH.

A polypeptide is provided, comprising a first peptide having least 90 percent sequence identity to SEQ ID NO: 2, a second peptide having at least 90 percent sequence identity to SEQ ID NO: 4, and a 2-amino acid linker between the first and second polypeptides.

The sequence identity of the first peptide can vary. In some embodiments, the first peptide has at least 95 percent identity to SEQ ID NO: 2. In other embodiments, the first peptide has the amino acid sequence of SEQ ID NO: 2.

The sequence identity of the second peptide can also vary. In some embodiments, the second peptide has at least 95 percent identity to SEQ ID NO: 4. In other embodiments, the second peptide has the amino acid sequence of SEQ ID NO: 4.

In various embodiments, the 2-amino acid linker is Gly-Gly.

In any of the foregoing embodiments, the polypeptide has at least 90 percent sequence identity to SEQ ID NO: 1. In some of the foregoing embodiments, the polypeptide has at least 95 percent sequence identity to SEQ ID NO: 1. In some of the foregoing embodiments, the polypeptide has the amino acid sequence of SEQ ID NO: 1.

A polypeptide, comprising a first peptide having the amino acid sequence of SEQ ID NO: 2, a second peptide having the amino acid sequence of SEQ ID NO: 3, a third peptide having the amino acid sequence of SEQ ID NO: 5; and a 2-amino acid linker between the first and second polypeptides is provided.

In some embodiments, the sequence of the polypeptide, beginning at the N-terminus, is as follows: the first peptide (SEQ ID NO: 2), followed by the 2-amino acid linker, followed by the second peptide (SEQ ID NO: 3), followed by the third peptide (SEQ ID NO: 5).

In some of the above embodiments, the 2-amino acid linker is Gly-Gly.

In some of the above embodiments, the polypeptide has the amino acid sequence of SEQ ID NO: 1.

A method of treating Friedreich's Ataxia is provided, comprising administering a therapeutically effective amount of a pharmaceutical composition to a subject in need thereof, the pharmaceutical composition comprising a TAT-FXN fusion polypeptide having the amino acid sequence of SEQ ID NO: 1, a pharmaceutically acceptable vehicle, and a pharmaceutically acceptable excipient, wherein, in some embodiments, the TAT portion of the fusion polypeptide has the amino acid sequence of SEQ ID NO: 2, the FXN portion of the fusion polypeptide has the amino acid sequence of SEQ ID NO: 4, and a linker situated between the TAT portion and the FXN portion of the fusion polypeptide is Gly-Gly.

The TAT-FXN fusion polypeptide can be administered in an amount of about 5 mg $kg^{-1}$-60 mg $kg^{-1}$ per day. The TAT-FXN fusion polypeptide can be administered in an amount selected from: about 10 mg $kg^{-1}$-50 mg $kg^{-1}$ per day, about 20 mg $kg^{-1}$-40 mg $kg^{-1}$ per day, about 30 mg kg$^{-1}$-40 mg kg$^{-1}$ per day, about 40 mg kg$^{-1}$-50 mg kg$^{-1}$ per day, about 50 mg kg$_{-1}$-60 mg kg$^{-1}$ per day, about 5 mg kg$^{-1}$-10 mg kg$^{-1}$ per day, about 10 mg kg$^{-1}$-15 mg kg$^{-1}$ per day, about 15 mg kg$^{-1}$-20 mg kg$^{-1}$ per day, about 20 mg kg$^{-1}$-25 mg kg$^{-1}$ per day, about 25 mg kg$^{-1}$-30 mg kg$^{-1}$ per day, about 30 mg kg$^{-1}$-35 mg kg$^{-1}$ per day, about 35 mg kg$^{-1}$-40 mg kg$^{-1}$ per day, about 40 mg kg$^{-1}$-45 mg kg$^{-1}$ per day, about 45 mg kg$^{-1}$-50 mg kg$^{-1}$ per day, about 50 mg kg$^{-1}$-55 mg kg$^{-1}$ per day, and about 55 mg kg$^{-1}$-60 mg kg$^{-1}$ per day.

In any of the foregoing embodiments, the pharmaceutical composition can be administered by subcutaneous injection.

A method of treating FRDA-associated hypertrophic cardiomyopathy is provided, comprising administering a therapeutically effective amount of a pharmaceutical composition to a subject in need thereof, the pharmaceutical composition comprising a TAT-FXN fusion polypeptide having the amino acid sequence of SEQ ID NO: 1, a pharmaceutically acceptable vehicle, and a pharmaceutically acceptable excipient, wherein, in some embodiments, the TAT portion of the fusion polypeptide has the amino acid sequence of SEQ ID NO: 2, the FXN portion of the fusion polypeptide has the amino acid sequence of SEQ ID NO: 4, and a linker situated between the TAT portion and the FXN portion of the fusion polypeptide is Gly-Gly.

In some embodiments, the TAT-FXN fusion polypeptide is administered in an amount of about 5 mg kg$^{-1}$-60 mg kg$^{-1}$ per day. In other embodiments, the TAT-FXN fusion polypeptide is administered in an amount selected from: about 10 mg kg$^{-1}$-50 mg kg$^{-1}$ per day, about 20 mg kg$^{-1}$-40 mg kg$^{-1}$ per day, about 30 mg kg$^{-1}$-40 mg kg$^{-1}$ per day, about 40 mg kg$^{-1}$-50 mg kg$^{-1}$ per day, about 50 mg kg$^{-1}$-60 mg kg$^{-1}$ per day, about 5 mg kg$^{-1}$-10 mg kg$^{-1}$ per day, about 10 mg kg$^{-1}$-15 mg kg$^{-1}$ per day, about 15 mg kg$^{-1}$-20 mg kg$^{-1}$ per day, about 20 mg kg$^{-1}$-25 mg kg$^{-1}$ per day, about 25 mg kg$^{-1}$-30 mg kg$^{-1}$ per day, about 30 mg kg$^{-1}$-35 mg kg$^{-1}$ per day, about 35 mg kg$^{-1}$-40 mg kg$^{-1}$ per day, about 40 mg kg$^{-1}$-45 mg kg$^{-1}$ per day, about 45 mg kg$^{-1}$-50 mg kg$^{-1}$ per day, about 50 mg kg$^{-1}$-55 mg kg$^{-1}$ per day, and about 55 mg kg$^{-1}$-60 mg kg$^{-1}$ per day.

In any of the foregoing embodiments, the pharmaceutical composition is administered by subcutaneous injection.

A method of treating an FRDA-associated disease is provided, wherein the FRDA-associated disease is selected from a neurologic disorder, impaired swallowing, diabetes, vision loss, hearing loss, speech loss, metabolic syndrome, scoliosis, and combinations thereof. In this sixth aspect, the method comprises administering a therapeutically effective amount of a pharmaceutical composition to a subject in need thereof, the pharmaceutical composition comprising a TAT-FXN fusion polypeptide having the amino acid sequence of SEQ ID NO: 1, a pharmaceutically acceptable vehicle, and a pharmaceutically acceptable excipient, wherein, in some embodiments, the TAT portion of the fusion polypeptide has the amino acid sequence of SEQ ID NO: 2, the FXN portion of the fusion polypeptide has the amino acid sequence of SEQ ID NO: 4, and a linker situated between the TAT portion and the FXN portion of the fusion polypeptide is Gly-Gly.

In some embodiments, the TAT-FXN fusion polypeptide is administered in an amount of about 5 mg kg-1-60 mg kg-1 per day. In other embodiments, the TAT-FXN fusion polypeptide is administered in an amount selected from: about 10 mg kg-1-50 mg kg-1 per day, about 20 mg kg-1-40 mg kg-1 per day, about 30 mg kg-1-40 mg kg-1 per day, about 40 mg kg-1-50 mg kg-1 per day, about 50 mg kg-1-60 mg kg-1 per day, about 5 mg kg-1-10 mg kg-1 per day, about 10 mg kg-1-15 mg kg-1 per day, about 15 mg kg-1-20 mg kg-1 per day, about 20 mg kg-1-25 mg kg-1 per day, about 25 mg kg-1-30 mg kg-1 per day, about 30 mg kg-1-35 mg kg-1 per day, about 35 mg kg-1-40 mg kg-1 per day, about 40 mg kg-1-45 mg kg-1 per day, about 45 mg kg-1-50 mg kg-1 per day, about 50 mg kg-1-55 mg kg-1 per day, and about 55 mg kg-1-60 mg kg-1 per day.

In any of the foregoing embodiments, the pharmaceutical composition is administered by subcutaneous injection.

```
                        SEQUENCE LISTING

SEQ ID NO: 1, Amino acid sequence of a TAT-FXN fusion polypeptide (224 AA):
MYGRKKRRQR RRGGMWTLGR RAVAGLLASP SPAQAQTLTR VPRPAELAPL
CGRRGLRTDI DATCTPRRAS SNQRGLNQIW NVKKQSVYLM NLRKSGTLGH
PGSLDETTYE RLAEETLDSL AEFFEDLADK PYTFEDYDVS FGSGVLTVKL
GGDLGTYVIN KQTPNKQIWL SSPSSGPKRY DWTGKNWVYS HDGVSLHELL
AAELTKALKT KLDLSSLAYS GKDA.

SEQ ID NO: 2, Complete amino acid sequence of the HIV-1 transactivator of
transcription cell penetrating peptide (TAT-epp), with a methionine added at the
amino terminus for initiation (12 AA):
MYGRKKRRQRRR SEQ ID NO: 3, Amino acid sequence of the mitochondrial targeting sequence of
human frataxin (hFXN-mts) (80 AA):
MWTLGR RAVAGLLASP SPAQAQTLTR
VPRPAELAPL CGRRGLRTDI DATCTPRRAS SNQRGLNQIW NVKKQSVYLM NLRK SEQ ID NO: 4, Amino acid sequence of complete human Frataxin protein
(hFXN) (210 AA):
MWTLGR RAVAGLLASP SPAQAQTLTR VPRPAELAPL
CGRRGLRTDI DATCTPRRAS SNQRGLNQIW NVKKQSVYLM NLRKSGTLGH
PGSLDETTYE RLAEETLDSL AEFFEDLADK PYTFEDYDVS FGSGVLTVKL
GGDLGTYVIN KQTPNKQIWL SSPSSGPKRY DWTGKNWVYS HDGVSLHELL
AAELTKALKT KLDLSSLAYS GKDA SEQ ID NO: 5, Amino acid sequence of mature human Frataxin protein (130 AA):
SGTLGH PGSLDETTYE RLAEETLDSL AEFFEDLADK PYTFEDYDVS
FGSGVLTVKL GGDLGTYVIN KQTPNKQIWL SSPSSGPKRY DWTGKNWVYS
HDGVSLHELL AAELTKALKT KLDLSSLAYS GKDA
```

SEQUENCE LISTING

SEQ ID NO: 6, Nucleic acid sequence (cDNA) encoding the TAT-FXN fusion
polypeptide of SEQ ID NO: 1; optimized for expression in E. coli (684 bases):
CATATGTATGGTAGAAAGAAACGTCGTCAACGTCGTCGTGGTGGTATGTGGACCT
TGGGCCGTCGCGCGGTTGCGGGCCTGCTGGCGAGCCCAAGCCCGGCACAGGCGC
AGACCCTGACGCGCGTTCCGCGTCCGGCGGAATTGGCCCCGTTGTGCGGTCGCCG
TGGTCTGCGCACGGATATCGACGCTACCTGTACGCCGCGTCGCGCGAGCAGCAA
TCAGCGTGGCCTGAATCAAATTTGGAACGTCAAGAAACAATCTGTTTACCTGATG
AATCTGCGCAAGAGCGGTACGTTGGGTCACCCGGGCAGCCTGGACGAGACTACC
TATGAGCGCCTGGCTGAGGAAACGCTGGACAGCCTGGCCGAATTTTTCGAAGAT
CTCGCAGATAAGCCGTACACGTTTGAGGATTATGACGTGAGCTTCGGCAGCGGC
GTCTTAACCGTGAAACTGGGTGGTGACCTGGGCACCTACGTGATCAATAAGCAA
ACCCCGAACAAACAGATTTGGCTGAGCTCGCCGAGCTCTGGCCCTAAGCGTTAC
GATTGGACCGGTAAGAACTGGGTGTATTCCCACGACGGTGTCAGCCTGCATGAA
CTGCTGGCGGCAGAGCTGACCAAAGCGCTGAAAACTAAACTGGATCTGAGCTCC
CTGGCCTACAGCGGTAAAGACGCATAACTCGAG SEQ ID NO: 7: complete amino acid sequence of the HIV-1 transactivator of
transcription cell penetrating peptide (TAT-cpp) (11 AA):
YGRKKRRQRRR.

BRIEF DESCRIPTION OF THE FIGURES

FIG. 4 illustrates the lifespan of mice treated with the TAT-FXN fusion polypeptide provided by the present disclosure vs. untreated PVKO mice of FIG. 3 up to 180 days. Data is presented +/−SEM. PVKO male and female mice treated with the TAT-FXN fusion polypeptide (SEQ ID NO: 1) live significantly longer than vehicle treated PVKO mice.

FIG. 5 depicts the amino acid sequence of a TAT-FXN fusion polypeptide (SEQ ID NO: 1) provided by the present disclosure. The Gly-Gly linker peptide is underlined.

FIG. 7C depicts tissue levels of human FXN in control PVKO mice, dosed only with vehicle (not the TAT-FXN fusion polypeptide). These mice were the negative controls for the test mice shown in FIG. 7B.

FIG. 12B is an image of the Western Blot of the Vyas et al. polypeptide incubated for different times in 15% human plasma.

FIG. 13A, panel A is an image of Schwann cells in one well of a 96-well plate treated for two days with 0 µM TAT-FXN fusion polypeptide (SEQ ID NO: 1) and stained with the nuclear stain Hoechst 33342 and the anti-frataxin stain Texas Red. Panel B is an image of Schwann cells in one well of a 96-well plate treated for two days with 0 µM Vyas et al. polypeptide and stained with the nuclear stain Hoechst 33342 and the anti-frataxin stain Texas Red. Panel C is an image of Schwann cells in one well of a 96-well plate treated for two days with 12.5 µM TAT-FXN fusion polypeptide and stained with the nuclear stain Hoechst 33342 and the anti-frataxin stain Texas Red. Panel D is an image of Schwann cells in one well of a 96-well plate treated for two days with 12.5 µM Vyas et al. polypeptide and stained with the nuclear stain Hoechst 33342 and the anti-frataxin stain Texas Red. Panel E is an image of Schwann cells in one well of a 96-well plate treated for two days with 12.5 µM TAT-FXN fusion polypeptide, stained with the nuclear stain Hoechst 33342 and the anti-frataxin stain Texas Red and imaged using 60×oil objective. Panel F is an image of Schwann cells in one well of a 96-well plate treated for two days with 12.5 µM Vyas et al. polypeptide, stained with the nuclear stain Hoechst 33342 and the anti-frataxin stain Texas Red and imaged using 60× oil objective.

DETAILED DESCRIPTION

Figure 1:
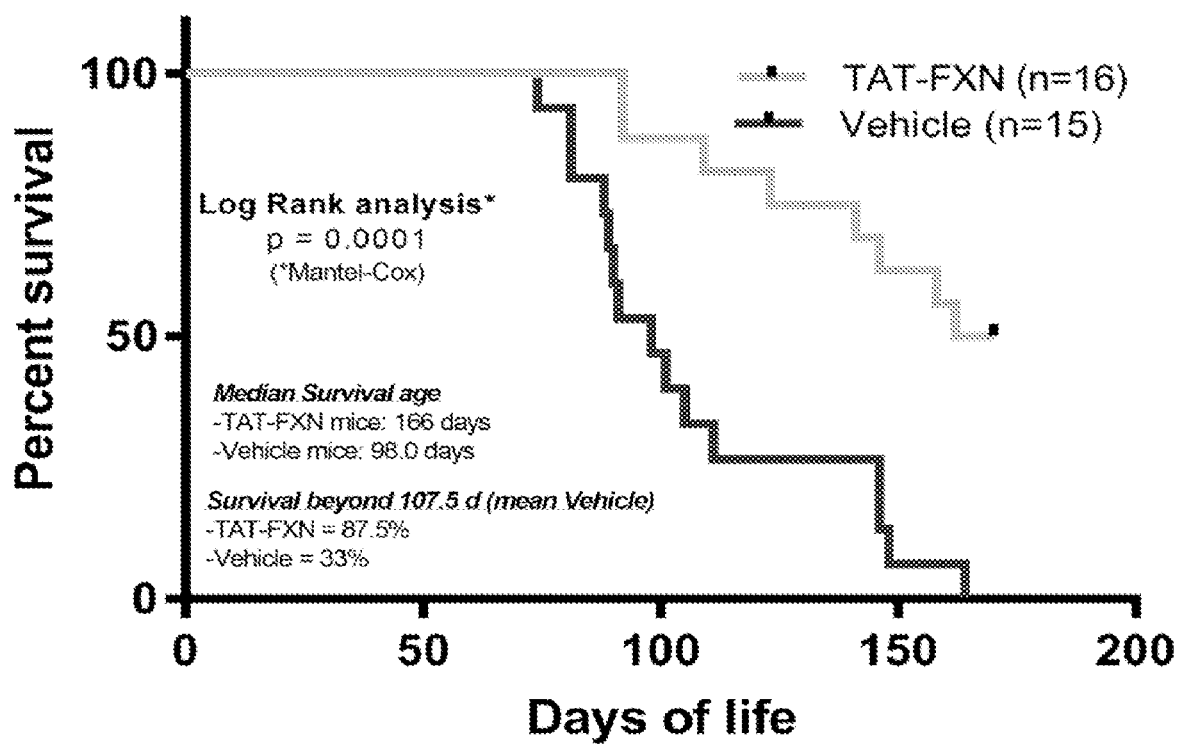
FIG. 1 presents a Kaplan-Meier Survival Curve for MCK-Cre FXN KO mice treated with the TAT-FXN fusion polypeptide provided by the present disclosure (SEQ ID NO: 1) (10 mg/kg, SC, 3×per week) or Vehicle (1 µl/g, SC 3×per week) from day 15 to day 170 of life. These mice are a model of the fatal hypertrophic cardiomyopathy of FRDA.

For the purposes of promoting an understanding of the principles of the novel technology, reference will now be made to the preferred compositions, methods of making, and methods of use thereof, and specific language will be used to describe the same. It will nevertheless be understood that no limitation of the scope of the novel technology is hereby intended, such alterations, modifications, and further applications of the principles of the novel technology being contemplated as would normally occur to one skilled in the art to which the novel technology relates are within the scope of this disclosure and the claims.

Definitions

Unless otherwise indicated in the context a term is used, the terms will have the following meanings as utilized herein.

The term 'about' refers to a range of values plus or minus 10 percent, e.g., about 1.0 encompasses values from 0.9 to 1.1.

"Pharmaceutically acceptable" refers to approved or approvable by a regulatory agency of a government, such as the U.S. Food and Drug Administration (U.S. FDA) or the European EMA, or listed in the U.S. Pharmacopoeia or other generally recognized pharmacopoeia for use in mammals and/or animals, and more particularly in humans.

A "subject" as used herein refers to a mammal, e.g., a monkey, a rat, a mouse, or a human. In one specific embodiment, a subject is a human.

"Treat," "treating" or "treatment" of any disease refers to reversing, alleviating, arresting, or ameliorating a disease or at least one of the clinical symptoms of a disease or inhibiting the progress of a disease or at least one of the clinical symptoms of the disease, in this case Friedreich's Ataxia. "Treat," "treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the subject.

"Therapeutically effective amount" refers to the amount of an active pharmaceutical ingredient that, when administered to a subject for treating a disease, or at least one of the clinical symptoms of a disease, is sufficient to affect such treatment of the disease or symptom thereof. The "therapeutically effective amount" may vary depending, for example, on the active pharmaceutical ingredient, the disease and/or symptoms of the disease, severity of the disease and/or symptoms of the disease or disorder, the age, weight, and/or health of the subject to be treated, and the judgment of the prescribing physician.

For example, a "therapeutically effective amount" of the disclosed TAT-FXN fusion polypeptide is that amount which is necessary or sufficient to treat FRDA, including, e.g., an FRDA-associated disease, disorder or condition. For example, a "therapeutically effective amount" of the disclosed TAT-FXN fusion polypeptide is that amount which is necessary or sufficient to ameliorate, improve or achieve a reduction in the severity of at least one symptom or indicator associated with FRDA, or to delay progression of FRDA, including, e.g., an FRDA-associated disease, disorder or condition. In some embodiments, the term "therapeutically effective amount" of the disclosed TAT-FXN fusion polypeptide may also be that amount which is necessary or sufficient to cause an increase the amount of hFXN in at least one tissue of a subject who is being administered the TAT-FXN fusion polypeptide.

"Therapeutically effective dose" refers to a dose that provides effective treatment of a disease or disorder in a subject. A therapeutically effective dose may vary from active pharmaceutical ingredient to active pharmaceutical ingredient, and from subject to subject, and may depend upon factors such as the condition of the subject, genetic character of the subject, and the route of delivery.

Friedreich's Ataxia and FXN

In spite of its rarity, Friedreich's Ataxia (FRDA) is the most common inherited ataxia in humans, with an estimated 4,000-5,000 cases in the United States. FRDA is thought to result from a deficiency of the mitochondrial protein frataxin (FXN), and specifically human frataxin (hFXN). The FXN protein is an essential and phylogenetically conserved protein that is found in cells throughout the body. The highest levels of FXN are found in the heart, spinal cord, liver, pancreas, and skeletal muscle. FXN is encoded in the nucleus, expressed in the cytoplasm and imported into the mitochondria where it is processed to its mature form. In humans, the 210-amino acid full-length hFXN (23.1 kDa) contains a typical mitochondrial targeting sequence (MTS) at the amino terminus that is processed in a 2-step cleavage by the mitochondrial processing peptidase (MPP) as it is imported into the mitochondrial matrix. The resulting protein is a 130-amino acid, 14.2 kDa mature hFXN protein. There have been no other intra-mitochondrial post-translational modifications identified.

The exact function of FXN has not been defined. Published literature and research indicate FXN could play several roles in mitochondrial iron homeostasis, notably in the de novo biosynthesis of iron-sulfur (Fe—S) cluster proteins, by presenting iron to Fe—S cluster assembly enzyme scaffold proteins, and heme synthesis. In the absence of FXN, free iron can accumulate in mitochondria with loss of activity of Fe—S cluster containing proteins. Important and key Fe—S cluster dependent enzyme systems include Complexes I, II, and III of the electron transport chain, and aconitase of the Krebs Cycle.

FRDA generally manifests as a progressive multisystem disease, typically beginning in mid-childhood. Patients suffer from multiple symptoms, including progressive neurologic and cardiac dysfunction. Key among these is a primary neurodegeneration of the dorsal root ganglia and the dentate nucleus of the cerebellum leading to the hallmark clinical findings of progressive limb ataxia and dysarthria. Hypertrophic cardiomyopathy is also common and is associated with early mortality in the 3rd to 5th decade of life in FRDA subjects. Other clinical findings can include scoliosis, fatigue, diabetes, visual impairment, and hearing loss.

Inheritance associated with FRDA is autosomal recessive and is predominantly caused by an inherited GAA triplet expansion in the first intron of both alleles of the hFXN gene. This triplet expansion causes transcriptional repression of the FRDA gene, which causes patients to produce only small quantities of hFXN. Heterozygotes (carriers) typically have hFXN levels at ~50% of normal but are phenotypically normal.

Currently, there are no FDA-approved treatments which directly address or ameliorate the FXN deficiency that occurs with FRDA.

TAT-FXN Fusion Polypeptides

In some embodiments, the present disclosure provides a TAT-FXN fusion polypeptide, i.e., a polypeptide that comprises an amino acid sequence with at least about 90% sequence identity to human frataxin (FXN, SEQ ID NO: 4 or SEQ ID NO: 5), fused to an amino acid sequence with at least about 90% sequence identity to TAT-cpp (cell penetrant peptide, SEQ ID NO: 2 or SEQ ID NO: 7) as disclosed herein.

Frataxin (e.g., complete human frataxin protein, SEQ ID NO: 4) is an essential and highly conserved protein expressed in most eukaryotic organisms and targeted to the mitochondrial matrix. It appears to function in mitochondrial iron homeostasis, notably in the de novo biosynthesis of iron-sulfur (Fe—S) cluster proteins, by presenting iron to IscU scaffold proteins, and heme. Iron-sulfur clusters are integral and essential components of multiple protein complexes in mitochondria, including Complexes I, II, and III of the electron transport chain, as well as Aconitase and Succinate Dehydrogenase of the Krebs Cycle. Iron-Sulfur clusters are also used extensively throughout the cytosol and nucleus of the cell. In its absence, free iron accumulates in mitochondria with loss of activity of Fe—S containing proteins, and loss of energy production due to electron transport chain damage and extensive mitochondrial protein acetylation.

In some embodiments, the TAT-FXN fusion polypeptide disclosed herein may comprise an amino acid sequence with at least about 90% sequence identity, e.g., about 95%, about 99% or about 100% sequence identity, to the amino acid sequence of the complete human frataxin protein (SEQ ID NO: 4). In some embodiments, the TAT-FXN fusion polypeptide disclosed herein may comprise an amino acid sequence with at least about 90% sequence identity, e.g., about 95%, about 99% or about 100% sequence identity, to the amino acid sequence of the mature human frataxin protein (SEQ ID NO: 5).

In some embodiments, the TAT-FXN fusion polypeptide disclosed herein may comprise at least one point mutation in the amino acid sequence of the complete human frataxin protein (SEQ ID NO: 4) or the amino acid sequence of the mature human frataxin protein (SEQ ID NO: 5). Examples of point mutations that may be comprised in frataxin are described, e.g., in U.S. Pat. No. 9,217,019, the entire contents of which are hereby incorporated herein by reference. In one specific embodiment, a TAT-FXN fusion polypeptide may comprise a mutation at the amino acid position 147 of SEQ ID NO: 4 or position 67 of SEQ ID NO: 5. For example, the lysine (K) residue at amino acid position 147 of SEQ ID NO: 4 or at amino acid position 67 of SEQ ID NO: 5 may be substituted with a different amino acid residue, such as a histidine, serine, threonine, asparagine, glutamine, glycine, alanine, valine, isoleucine, leucine, methionine, phenylalanine, tyrosine, tryptophan, cysteine, proline, aspartic acid, or glutamic acid residue. In one embodiment, the lysine (K) residue at amino acid position 147 of SEQ ID NO: 4 or at amino acid position 67 of SEQ ID NO: 5 may be substituted with an arginine (R) residue.

TAT-cpp (cell penetrant peptide, SEQ ID NO: 2 or SEQ ID NO: 7) is a short, cationic peptide derived from the larger TAT protein of HIV that has cell penetrant properties. TAT has been used to transduce multiple cargos, such as proteins, into cells and tissues in animals. Cell penetrant peptides can transport a variety of molecules, such as proteins, peptides, or oligonucleotides into cells which otherwise cannot absorb large molecular weight compounds. Delivery of a cargo by a cell penetrant peptide has been accomplished for multiple organelles, such as mitochondria, lysosomes, and the nucleus, and they are capable of delivering a cargo across the placenta. TAT has already been used to replace missing cytosolic enzymes in animal models of disease, such as purine nucleoside phosphorylase and in animal models of human mitochondrial diseases, such as lipoamide dehydrogenase deficiency and Friedreich's Ataxia.

Without wishing to be bound by any theory, it is presently believed that the TAT-cpp peptide of SEQ ID NO: 2 or SEQ ID NO: 7 serves to deliver a TAT-FXN fusion polypeptide across cell membranes into mitochondria. The mitochondria can then properly process the TAT-FXN fusion polypeptide via proteolytic processing to remove the transit peptide sequences TAT-cpp (SEQ ID NO: 2 or SEQ ID NO: 7) and MTS (SEQ ID NO: 3), releasing mature FXN (the C-terminal 130 amino acids of the hFXN protein; SEQ ID NO: 5) and other possible active degradant(s) into the mitochondria.

In some embodiments, the TAT-FXN fusion polypeptide disclosed herein can be a peptide having the amino acid sequence of SEQ ID NO: 1. The TAT-FXN fusion polypeptide can therefore be a 224-amino acid recombinant fusion polypeptide comprising a short, cationic cell penetrating peptide, TAT-cpp (SEQ ID NO: 2), fused through a di-peptide (Gly-Gly) linker to the amino-terminus of the complete human frataxin protein (hFXN) (SEQ ID NO: 4), which includes the native mitochondrial targeting sequence (MTS) (SEQ ID NO: 3) of hFXN. Put another way, the disclosed TAT-FXN fusion polypeptide can be a 224-amino acid recombinant fusion polypeptide comprising a short, cationic cell penetrating peptide, TAT-cpp (SEQ ID NO: 2), fused through a di-peptide (Gly-Gly) linker to the amino-terminus of the native mitochondrial targeting sequence (MTS) (SEQ ID NO: 3) of hFXN, which is fused to the amino-terminus of the mature human frataxin protein (hFXN) (SEQ ID NO: 5).

The TAT-FXN fusion polypeptide provided by the present disclosure, e.g., the fusion polypeptide comprising, or consisting of, SEQ ID NO: 1, demonstrates several technical improvements over the TAT-FXN peptide previously disclosed by Vyas et al. First, the TAT-FXN fusion polypeptide provided by the present disclosure is smaller in size than that disclosed by Vyas et al. For example, the molecular weight of the TAT-FXN fusion polypeptide of SEQ ID NO: 1 is about 24.92 kDa, whereas the molecular weight of the Vyas et al. polypeptide is about 29.28 kDa. This reduction in molecular weight makes the TAT-FXN fusion polypeptide easier to synthesize and easier to solubilize.

Second, the TAT-FXN fusion polypeptide provided by the present disclosure has no unnecessary sequences. For example, the TAT-FXN fusion polypeptide of SEQ ID NO: 1 is approximately 40 aa shorter than the Vyas et al. polypeptide. The shorter length of the TAT-FXN fusion polypeptide is due, in part, to the short, 2-amino acid Gly-Gly linker present in the TAT-FXN fusion polypeptide. The shorter length of the TAT-FXN fusion polypeptide as compared to the length of the Vyas et al. polypeptide significantly reduces antigenic potential of the TAT-FXN fusion polypeptide to help ensure subjects will not develop a humoral immune response to the TAT-FXN fusion polypeptide with repeated injections. Development of a humoral immune response would decrease the therapeutic efficacy of the TAT-FXN fusion polypeptide. The prior art polypeptide disclosed by Vyas et al. is associated with an increased risk of developing such an immune response due to its larger size; this fact is acknowledged by the authors of Vyas et al. themselves (see Vyas et al., supra, at p. 1242). The increased risk of antigenicity is due, at least in part, to the length of the Vyas et al. linker.

In contrast, the TAT-FXN fusion polypeptide provided by the present disclosure contains, in some embodiments, only a 1, 2 or 3-amino acid linker, e.g, a 2-amino acid Gly-Gly linker. This linker was specifically selected to minimize, if not eliminate, the risk of the TAT-FXN fusion polypeptide triggering a humoral immune response after prolonged introduction into a subject.

Although the selected Gly-Gly linker is expected to minimize antigenicity (i.e., reduce the risk of humoral immune response), it will be recognized that, in some embodiments, other short, non-antigenic linkers may be used in place of Gly-Gly to link TAT and FXN peptides. Such alternative linkers are known in the art and are generally rich in small or polar amino acids such as glycine and serine to provide good flexibility and solubility. Examples of alternative linkers include glycine repeat linkers ((Gly)$_n$; e.g., (Gly)$_8$ (SEQ ID NO: 8)) and "GS" linkers primarily made up of stretches of glycine and serine (e.g., (Gly-Gly-Gly-Gly-Ser)$_n$ (SEQ ID NO: 9)), although others are also known (e.g., Gly-Ser-Ala-Gly-Ser-Ala-Ala-Gly-Ser-Gly-Glu-Phe (SEQ ID NO: 10)). An alternative linker to Gly-Gly should remain short (e.g., 20 or fewer amino acids, such as 1, 2 or 3 amino acids). Alternative linkers that minimize antigenicity, result in good fusion polypeptide solubility, and are expressible from a desired expression system are also contemplated by the present disclosure.

In some embodiments, the TAT-FXN fusion polypeptide provided by the present disclosure can also omit a linker. For example, a TAT-FXN fusion polypeptide may consist of a first peptide having an amino acid sequence with at least about 90% sequence identity, e.g., at least about 95% or about 100% sequence identity, to SEQ ID NO: 2 or SEQ ID NO: 7 and a second peptide having an amino acid sequence with at least about 90% sequence identity, e.g., at least about 95% or about 100% sequence identity, to SEQ ID NO: 4. In another example, the TAT-FXN fusion polypeptide may consist of a first peptide having an amino acid sequence with at least about 90% sequence identity, e.g., at least about 95% or about 100% sequence identity, to SEQ ID NO: 2 or SEQ ID NO: 7; a second peptide having an amino acid sequence with at least about 90% sequence identity, e.g., at least about 95% or about 100% sequence identity, to SEQ ID NO: 3; and a third peptide having an amino acid sequence with at least about 90% sequence identity, e.g., at least about 95% or about 100% sequence identity, to SEQ ID NO: 5.

Third, in some embodiments, a TAT-FXN fusion polypeptide provided by the present disclosure, e.g., TAT-FXN fusion polypeptide of SEQ ID NO: 1, comprises an FXN polypeptide that has 100% sequence identity with the human FXN protein, whereas the Vyas et al. polypeptide does not. For example, the Vyas et al. polypeptide contains a point mutation in its amino acid sequence as compared to the human FXN. A TAT-FXN fusion polypeptide of the present disclosure with an amino acid sequence that is 100% identical to the amino acid sequence of human frataxin is expected to be associated with optimal sequence recognition and processing by the mitochondrial processing peptidase, as well as decreased antigenicity of the TAT-FXN fusion polypeptide.

Fourth, the Vyas et al. polypeptide comprises a histidine (HIS) tag (6×His (SEQ ID NO: 11)), whereas the TAT-FXN fusion polypeptides described herein omit a HIS tag. The HIS tag present in the Vyas et al. polypeptide is a purification tag, which is convenient for academic purposes. However, a HIS tag is antigenic, which increases the chance that the Vyas et al. polypeptide would elicit an undesired humoral immune response upon repeated injection into a subject.

Fifth, as set forth above, the TAT-FXN fusion polypeptides possess markedly improved solubility as compared to the Vyas et al. polypeptide. Table 1 sets forth a direct comparison of several physical parameters between a TAT-FXN fusion polypeptide of the present disclosure (SEQ ID NO: 1) and the Vyas et al. polypeptide.

TABLE 1

| Parameter | Vyas et al.TAT-FXN | TAT-FXN |
| --- | --- | --- |
| Number of amino acids | 264 | 224 |
| Molecular Weight | 29,277.90 Da | 24,922.26 |

TABLE 1-continued

| Parameter | Vyas et al.TAT-FXN | TAT-FXN |
|---|---|---|
| Theoretical pI | 9.57 | 9.72 |
| Total number (−) charged aa | 29 | 23 |
| Total number (+) charged aa | 39 | 34 |
| Estimated half-life | 30 hours | 30 hours |
| Instability Index | 47.93 | 53.51 |
| Aliphatic Index | 68.03 | 76.25 |
| Hydropathicity (GRAVY index) | −0.754 | −0.610 |

The GRAVY (Grand Average of Hydropathy) value for a peptide is calculated as the sum of hydropathy values of all the amino acids, divided by the number of residues in the sequence. The larger the number, the more hydrophobic the peptide.

The aliphatic index is the relative volume occupied by aliphatic side chains (alanine, valine, isoleucine, and leucine). It may be regarded as a positive factor for the increase of thermostability of globular proteins.

The improved solubility of the TAT-FXN fusion polypeptide of the present disclosure is evidenced by the larger aliphatic index of the TAT-FXN fusion polypeptide and its smaller hydropathicity index. As a result of these indices, the present inventors can now achieve concentrations of >50 mg/ml of the TAT-FXN fusion polypeptide in a solution, e.g., in a pharmaceutical composition. In contrast, the concentration of the Vyas et al. polypeptide in a solution cannot exceed about 2 mg/ml before it begins to precipitate out of solution. As can be appreciated, improved and maintained solubility allows for greater accuracy in dosing and can dramatically reduce the volume of a therapeutic dose needed to achieve a desired effect.

Sixth, in contrast to the Vyas et al. polypeptide, the TAT-FXN fusion polypeptide of the present disclosure is soluble in higher pH buffers, particularly at physiologic pH, making it compatible with human subcutaneous injection.

Seventh, the TAT-FXN fusion polypeptides may be purified using an improved purification strategy as compared to the purification strategy employed for the purification of the Vyas et al. polypeptide. The purification strategy employed for the Vyas et al. polypeptide relies upon a 6× His tag (SEQ ID NO: 11) at the amino-terminus of the Vyas et al. polypeptide, which markedly complicates purification due to additional proteins which will be pulled down with the Vyas et al. polypeptide, introducing impurities. The presence of these undesirable impurities requires multiple additional purification steps and/or chromatography steps to produce a purified peptide. In contrast, the TAT-FXN fusion polypeptide of the present disclosure does not contain, or depend on, a HIS tag; initial purification efforts will therefore yield a far cleaner product, requiring less downstream purification in order to yield a purified product. As shown in Example 2, single-step purification is more than adequate for initial purification of the TAT-FXN fusion polypeptide, with purification levels at about 90% or greater from a single purification step.

Nucleic Acids

Also provided are nucleic acid molecules that encode the TAT-FXN fusion polypeptides disclosed herein. A nucleic acid sequence that has been optimized for expression in a chosen expression system is also disclosed. The expression system can be $E.\ coli$, and the optimized nucleic acid sequence (i.e., cDNA) may comprise, for example, the nucleic acid sequence of SEQ ID NO: 6. The nucleic acid sequence of SEQ ID NO: 6 was codon optimized for expression in $E.\ coli$.

The nucleic acid sequence encoding the TAT-FXN fusion polypeptide can be included in an expression cassette for use in the chosen expression system. Expression cassettes generally include a promoter at the 5' end of the cassette, upstream of the TAT-FXN fusion polypeptide-encoding nucleic acid sequence. Untranslated DNA at the 5' end of the coding sequence can include a promoter region with multiple promoter and/or enhancer elements operably linked to the nucleic acid sequence to provide for initiation of transcription.

The nucleic acid sequence encoding the TAT-FXN fusion polypeptide, e.g., an expression cassette disclosed herein, can be included in an expression vector expressible in the chosen expression system. In this regard, recombinant expression vectors are provided comprising a nucleic acid sequence that encodes the TAT-FXN fusion polypeptide of the disclosure. The term "recombinant expression vector" refers to a genetically-modified oligonucleotide or polynucleotide construct that permits the expression of the TAT-FXN fusion polypeptide by a host cell. Recombinant expression vectors comprise a suitable vector backbone for use in transforming or transfecting host cells of a chosen expression system. Suitable vector backbones for various expression systems are known and include plasmids and viruses. Recombinant expression vectors can be prepared using recombinant DNA techniques described in the art.

The recombinant expression vector can include a native or non-native promoter operably linked to the nucleic acid sequence encoding the TAT-FXN fusion polypeptide.

The recombinant expression vector can include regulatory sequences, such as transcription and translation initiation and termination codons, which are specific to the type of host cell (e.g., $E.\ coli$) into which the vector is to be introduced, as appropriate. The recombinant expression vector can also include restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like.

Also provided are host cells including an expression cassette or expression vector described herein. The term "host cell" refers to any type of cell that can contain and express an expression cassette or expression vector described herein. The host cell can be a eukaryotic cell, e.g., yeast, plant, animal, fungi, or algae, or can be a prokaryotic cell, e.g., bacteria or protozoa. The host cell can be an adherent cell or a suspended cell, i.e., a cell that grows in suspension. Suitable host cells include, for example, $E.\ coli$ cells.

Also provided is a population of host cells. The population of host cells can be a clonal population of cells, in which all cells of the population are clones of a single host cell including a recombinant expression vector.

The TAT-FXN fusion polypeptide can be isolated and/or purified from a host cell or a population of host cells.

Therapeutic Uses

The TAT-FXN fusion polypeptide can be administered to a subject to treat any condition associated with a deficiency in FXN. The TAT-FXN fusion polypeptide is a chimeric protein comprising a functional version of the FXN protein linked to the HIV-1 TAT-cpp (cell penetrant peptide). Without wishing to be bound by any theory, one possible mechanism of action of the TAT-FXN fusion polypeptide is to deliver mature FXN, and other possible active degradant(s), to the mitochondria of a subject. Delivery to the mitochondria can occur via the TAT peptide. Once inside the mitochondria, proteolytic processing of the fusion polypeptide will result in the release of mature FXN. In an FXN-deficient subject, provision of mature FXN directly to the mitochondria can supplement, if not completely replace, the deficiency in FXN.

Friedreich's Ataxia

Administration of at least one therapeutically effective dose of the TAT-FXN fusion polypeptide provided by the present disclosure can be clinically effective to treat Friedreich's ataxia (FRDA).

It is presently anticipated that protein replacement therapy with the TAT-FXN fusion polypeptide will correct the metabolic defect in FRDA and restore adequate cellar function in patients. It is also anticipated that treatment with the TAT-FXN fusion polypeptide will change FRDA from a progressive and deadly disease to a chronic condition that is managed by frequent injections of the fusion polypeptide, much as insulin has changed diabetes into a chronic disease with normal life activities. In older FRDA patients with established disease, it is anticipated that administration of the TAT-FXN fusion polypeptide will halt disease progression. In children diagnosed before onset of FRDA symptoms, it is anticipated that administration of the TAT-FXN fusion polypeptide will result in near complete preservation of tissue function and health.

The gene defect for FRDA was identified in 1996 and there is consensus in the field that lack of FXN protein in mitochondria is the biochemical defect. Multiple investigators have shown that replacement of FXN in deficient patient fibroblasts, and even in yeast with loss of FXN, will rescue the phenotype. Thus, the consensus in the field is that therapies for FRDA must include increasing levels of FXN protein in mitochondria of affected tissues. Although the precise function of FXN has yet to be defined, it is clear that FXN participates in iron-sulfur cluster assembly. In its absence, mitochondrial proteins containing an iron-sulfur cluster (Complexes I, II, and III of the electron transport chain, and aconitase of the Krebs cycle) are severely defective in activity. As a result, those tissues with high dependence on energy production by mitochondria, such as heart and brain, are severely affected and greater than about 60% of patients die from heart failure. As with other mitochondrial diseases, multiple organ systems are also impacted, such as eye, hearing, and pancreas. Thus, clinically relevant target tissues include the heart and brain and can be followed by common clinical testing, such as echocardiography, and neurologic assays such as the Friedreich Ataxia Rating Scale (FARS).

Administration of the disclosed TAT-FXN fusion polypeptide, and/or a pharmaceutical composition comprising the disclosed TAT-FXN fusion polypeptide, can, therefore, be effective as a protein replacement therapy in FXN-deficient subjects diagnosed with FRDA, including, e.g., an FRDA-associated disease, disorder or condition, to treat the FRDA, including, e.g., the FRDA-associated disease, disorder or condition.

The term "FRDA", as used herein, encompasses any disease, disorder or condition associated with a frataxin deficiency. The term "FRDA-associated disease, disorder or condition", as used herein, encompasses a disease, disorder or condition secondary to and/or caused by FRDA, i.e., when present in a subject, it accompanies FRDA and is not present in a subject in the absence of FRDA. Non-limiting examples of an FRDA-associated disease, disorder, or condition, include FRDA-associated pneumonia, FRDA-associated hypertrophic cardiomyopathy and FRDA-associated diabetes. Other non-limiting examples of an FRDA-associated disease, disorder or condition include an FRDA-associated disease, disorder or condition characterized by, without limitation:

(1) a neurological deficiency including, without limitation, one or more of the following: loss of proprioception, loss of reflexes, loss of ability to walk, loss of ability to hold gaze with eyes;
(2) impaired swallowing and/or a progressive loss of the ability to swallow; progressive loss of hearing;
(3) progressive loss of vision due to retinal degeneration from lack of FXN;
(4) progressive loss of speech;
(5) metabolic syndrome including, without limitation, elevated triglycerides, low high-density lipoprotein (HDL) cholesterol, and elevated low-density lipoprotein (LDL) cholesterol;
(6) scoliosis that requires surgery to correct; and/or combinations thereof.

In some embodiments, administration of the disclosed TAT-FXN fusion polypeptide and/or a pharmaceutical composition comprising the disclosed TAT-FXN fusion polypeptide to a subject, may treat FRDA, including, e.g., an FRDA-associated disease, disorder or condition. "Treating FRDA", as used herein, encompasses ameliorating, improving or achieving a reduction in the severity of FRDA, including, e.g., an FRDA-associated disease, disorder or condition. For example, "treating FRDA" encompasses ameliorating, improving or achieving a reduction in at least one symptom or indicator associated with FRDA. "Treating FRDA", as used herein, also encompasses delaying progression of FRDA, including, e.g., an FRDA-associated disease disorder or condition, e.g., delaying appearance of at least one symptom or indicator associated with FRDA or preventing an increase in the severity of at least one symptom or indicator associated with FRDA, in a subject.

In some embodiments, the term "treating FRDA" also encompasses achieving increased survival (e.g., survival time) of a subject, e.g., a human, with FRDA, including, e.g., an FRDA-associated disease, disorder or condition. For example, treatment of FRDA may result in an increased life expectancy of a subject, e.g., a human, with FRDA, including, e.g., an FRDA-associated disease disorder or condition. In some embodiments, treatment of FRDA in the context of the present disclosure may result in an increased life expectancy of a subject of greater than about 10%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, or greater than about 200% or more, as compared to the average life expectancy of one or more control individuals with similar disease without treatment.

In some embodiments, treatment of FRDA, including, e.g., an FRDA-associated disease, disorder or condition, in the context of the present disclosure may result in an increased life expectancy of a subject by greater than about 6 months, greater than about 8 months, greater than about 10 months, greater than about 12 months, greater than about 2 years, greater than about 4 years, greater than about 6 years, greater than about 8 years, or greater than about 10 years or more, as compared to the average life expectancy of one or more control individuals with similar disease without treatment. In some embodiments, treatment of FRDA, including, e.g., an FRDA-associated disease, disorder or condition in the context of the present disclosure may result in a long-term survival of a subject, e.g., a human, with FRDA, including, e.g., an FRDA-associated disease, disorder or condition. The term "long-term survival", as used herein, refers to a survival time or life expectancy longer than about 40 years, 45 years, 50 years, 55 years, 60 years, or longer.

Clinical assessments known to one of ordinary skill in the art may be used to assess FRDA, including, e.g., an FRDA-associated disease, disorder or condition, to determine the severity of the FRDA and/or to determine the effect of administration to a subject of the disclosed TAT-FXN fusion polypeptide and/or a pharmaceutical composition comprising the disclosed TAT-FXN fusion polypeptide. Examples of methods of clinical assessment of FRDA, including assessments of the severity of FRDA, are described, e.g., in Paap et al., "Standardized Assessment of Hereditary Ataxia Patients in Clinical Studies", *Mov Disord Clin Pract.* 2016, 3(3):230-240 and Patel et al., "Progression of Friedreich ataxia: quantitative characterization over 5 years", *Ann Clin Transl Neurol* 2016, 3(9):684-694, the entire contents of each of which are hereby incorporated herein by reference.

Timed 25-Foot Walk (T25-FW) is a quantitative mobility and leg function performance test that measures the time needed to complete a 25-foot walk. In some embodiments, administration to a subject of the disclosed TAT-FXN fusion polypeptide and/or a pharmaceutical composition comprising the disclosed TAT-FXN fusion polypeptide may result in a decrease in the severity of FRDA as measured, e.g., by the time needed to complete a 25-foot walk. For example, administration to a subject of the disclosed TAT-FXN fusion polypeptide and/or a pharmaceutical composition comprising the disclosed TAT-FXN fusion polypeptide may result in a decrease in the time needed to complete a 25-foot walk, e.g., a decrease of at least about 5%, at least about 10%, at least about 25%, or at least about 50% in the time needed to complete a 25-foot walk, as compared to the time needed to complete a 25-foot walk measured in the subject prior to administration of the disclosed TAT-FXN fusion polypeptide and/or a pharmaceutical composition comprising the disclosed TAT-FXN fusion polypeptide, or as compared to a baseline value. A baseline value may be the time needed to complete a 25-food walk measured prior to administration of the disclosed TAT-FXN fusion polypeptide of the disclosure.

In other embodiments, administration to a subject of the disclosed TAT-FXN fusion polypeptide and/or a pharmaceutical composition comprising the disclosed TAT-FXN fusion polypeptide may delay progression of FRDA in the subject as measured, e.g., by the time needed to complete a 25-foot walk. For example, administration to a subject of the disclosed TAT-FXN fusion polypeptide and/or a pharmaceutical composition comprising the disclosed TAT-FXN fusion polypeptide may result in a substantially similar time needed to complete a 25-foot walk, or a lack of a substantial increase in the time needed to complete a 25-foot walk (e.g., less than a 20%, less than a 10%, or less than a 5% increase in the time needed to complete a 25-foot walk), as compared to the baseline value, i.e., time needed to complete a 25-foot walk measured in the subject prior to administration of the disclosed TAT-FXN fusion polypeptide and/or a pharmaceutical composition comprising the disclosed TAT-FXN fusion polypeptide.

The Modified Friedreich's Ataxia Rating Scale (mFARS) is an examination-based rating scale for assessing the severity of FRDA as described, e.g., in Burk et al., "Monitoring progression in Friedreich ataxia (FRDA): the use of clinical scales", *J of Neurochemistry* 2013, 126(suppl. 1):118-124 and Rummey et al., "Psychometric properties of the Friedreich's Ataxia Rating Scale", *Neurol Genet* 2019, 5:e371, the entire contents of each of which are hereby incorporated herein by reference.

In some embodiments, the mFARS score may comprise at least one of the following subscores: a) a score based on the Functional Disability Rating Scale (FARS-FDS; 0-6 scale; assessment usually made by a neurologist; b) a score based on the Activities of Daily Living Scale (FARS-ADL, 0-36 scale; assessment made by a patient or caregiver); and c) a score based on the Neurological Rating Scale (FARS-neuro) 0-125 scale; assessment made by a neurologist). In some examples, the FARS_ADL score is a FARS rating scale assessing subject ability to complete ADLs (e.g., speech, cutting food, dressing, and personal hygiene), with scores ranging from 0 to 36 points. The respondent may be the subject; a combination of the subject and family; or a family member, spouse or caregiver for those subjects unable to complete the test.

In some embodiments, the score based on the Neurological Rating Scale may include modified scoring of the neurological rating scale involving direct subject participation and targeting specific areas impacted by FRDA, such as bulbar, upper limb, lower limb, and upright stability (mFARS-neuro, 0-99 scale). The mFARS-neuro excludes subscale D (peripheral nervous system) and the first 2 questions of subscale A (bulbar) from the neurological rating scale of the FARS questionnaire.

In some embodiments, the mFARS score may be based on two subscores derived from the full FARS questionnaire: mFARS-neuro as described above and the FARS_ADL as described above.

In some embodiments, administration to a subject of the disclosed TAT-FXN fusion polypeptide and/or a pharmaceutical composition comprising the disclosed TAT-FXN fusion polypeptide may result in a decrease in the severity of FRDA as measured, e.g., by an mFARS score, or at least one mFARS subscore as described herein. For example, administration to a subject of the disclosed TAT-FXN fusion polypeptide and/or a pharmaceutical composition comprising the disclosed TAT-FXN fusion polypeptide may result in a decrease in an mFARS score or at least one mFARS subscore, as compared to a baseline value, i.e., the mFARS score or the at least one mFARS subscore measured in the subject prior to administration of the disclosed TAT-FXN fusion polypeptide and/or a pharmaceutical composition comprising the disclosed TAT-FXN fusion polypeptide.

In other embodiments, administration to a subject of the disclosed TAT-FXN fusion polypeptide and/or a pharmaceutical composition comprising the disclosed TAT-FXN fusion polypeptide may delay progression of FRDA in the subject as measured, e.g., by an mFARS score or at least one mFARS subscore as disclosed herein. For example, administration to a subject of the disclosed TAT-FXN fusion polypeptide and/or a pharmaceutical composition comprising the disclosed TAT-FXN fusion polypeptide may result in a substantially similar mFARS score or at least one mFARS subscore, or a substantial lack of an increase in an mFARS score or at least one mFARS subscore, as compared to a baseline value, i.e., the mFARS score or the at least one mFARS subscore measured in the subject prior to administration of the disclosed TAT-FXN fusion polypeptide and/or a pharmaceutical composition comprising the disclosed TAT-FXN fusion polypeptide, or as compared to a baseline value.

The Nine-Hole Peg Test (9HPT) may be used to measure finger dexterity in subjects with FRDA. In this test, a subject is asked to take pegs from a container, one by one, and place them into the nine holes on the board as quickly as possible. The subject must then remove the pegs from the holes, one by one, and replace them back into the container. Scores are based on the time taken to complete the test activity, recorded in seconds.

In some embodiments, administration to a subject of the disclosed TAT-FXN fusion polypeptide and/or a pharmaceutical composition comprising the disclosed TAT-FXN fusion polypeptide may result in a decrease in the severity of FRDA as measured, e.g., by a 9HPT score. For example, administration to a subject of the disclosed TAT-FXN fusion polypeptide and/or a pharmaceutical composition comprising the disclosed TAT-FXN fusion polypeptide may result in an decrease in a 9HPT score expressed as time to complete the test activity (e.g., at least an about 5%, 10%, 25%, or 50% decrease in a 9HPT score expressed as time to complete the test activity), as compared to a baseline value, i.e., the 9HPT score measured in the subject prior to administration of the disclosed TAT-FXN fusion polypeptide and/or a pharmaceutical composition comprising the disclosed TAT-FXN fusion polypeptide.

In other embodiments, administration to a subject of the disclosed TAT-FXN fusion polypeptide and/or a pharmaceutical composition comprising the disclosed TAT-FXN fusion polypeptide may delay progression of FRDA in the subject as measured, e.g., by a 9HPT score. For example, administration to a subject of the disclosed TAT-FXN fusion polypeptide and/or a pharmaceutical composition comprising the disclosed TAT-FXN fusion polypeptide may result in a substantially similar 9HPT score, or a lack of a substantial increase in a 9HPT score expressed as time to complete the test activity, as compared to a baseline value, i.e., the 9HPT score measured in the subject prior to administration of the disclosed TAT-FXN fusion polypeptide and/or a pharmaceutical composition comprising the disclosed TAT-FXN fusion polypeptide.

In some embodiments, administration to a subject of the disclosed TAT-FXN fusion polypeptide and/or a pharmaceutical composition comprising the disclosed TAT-FXN fusion polypeptide results in an increase in the level of hFXN in at least one tissue or biological fluid of the subject, as compared to a baseline level, i.e., the hFXN level in the at least one tissue or biological fluid of the subject prior to administration of the disclosed TAT-FXN fusion polypeptide and/or a pharmaceutical composition comprising the disclosed TAT-FXN fusion polypeptide. In some embodiments, the increase in the level of hFXN in the at least one tissue or biological fluid of a subject resulting from administration of the disclosed TAT-FXN fusion polypeptide and/or a pharmaceutical composition comprising the disclosed TAT-FXN fusion polypeptide to the subject is sufficient to have a therapeutic effect, i.e., sufficient to treat FRDA in the subject.

In some embodiments, administration of the disclosed TAT-FXN fusion polypeptide and/or a pharmaceutical composition comprising the disclosed TAT-FXN fusion polypeptide to a subject with FRDA may result in a level of hFXN in at least one tissue or biological fluid of the subject that is lower than the level of hFXN in the at least one tissue or biological fluid of a subject who does not have FRDA (e.g., a normal, healthy subject), but is still sufficient to have a therapeutic effect, i.e., sufficient to treat FRDA in the subject. For example, after administration of the disclosed TAT-FXN fusion polypeptide and/or a pharmaceutical composition comprising the disclosed TAT-FXN fusion polypeptide to a subject with FRDA, the level of hFXN in at least one tissue or a biological fluid of the subject may be about 10% to about 50%, about 20% to about 60%, or about 30% to about 80% of the level of hFXN in the at least one tissue or a biological fluid of a subject who does not have FRDA (e.g., a normal, healthy subject), but the level of hFXN is still sufficient to have a therapeutic effect, i.e., sufficient to treat FRDA in the subject.

In some embodiments, administration to a subject with FRDA of the disclosed TAT-FXN fusion polypeptide and/or a pharmaceutical composition comprising the disclosed TAT-FXN fusion polypeptide may result in an increase of at least about 5%, about 10%, about 25%, about 50%, about 100%, about 150%, about 200%, about 300%, about 400%, about 500%, or about 600% in the level of hFXN in at least one tissue or biological fluid of the subject, as compared to the hFXN level in the at least one tissue or biological fluid of the subject prior to administration of the disclosed TAT-FXN fusion polypeptide and/or a pharmaceutical composition comprising the disclosed TAT-FXN fusion polypeptide, or as compared to a baseline level.

In some embodiments, administration to a subject with FRDA of the disclosed TAT-FXN fusion polypeptide and/or a pharmaceutical composition comprising the disclosed TAT-FXN fusion polypeptide may result in an increase of about 5% to about 30%, about 10% to about 50%, about 25% to about 100%, about 50% to about 150%, about 100% to about 300%, about 50% to about 250%, about 150% to about 500% or about 200% to about 700% in the level of hFXN in at least one tissue or biological fluid of the subject, as compared to the hFXN level in the at least one tissue or biological fluid of the subject prior to administration of the disclosed TAT-FXN fusion polypeptide and/or a pharmaceutical composition comprising the disclosed TAT-FXN fusion polypeptide, or as compared to a baseline level. In some embodiments, administration to a subject of the disclosed TAT-FXN fusion polypeptide and/or a pharmaceutical composition comprising the disclosed TAT-FXN fusion polypeptide may result in an increase of at least about 2-fold, about 3-fold, about 4-fold, about 5-fold in the level of hFXN in at least one tissue or biological fluid of the subject, as compared to the hFXN level in the at least one tissue or biological fluid of the subject prior to administration of the disclosed TAT-FXN fusion polypeptide and/or a pharmaceutical composition comprising the disclosed TAT-FXN fusion polypeptide, or as compared to a baseline level. In some embodiments, administration to a subject of the disclosed TAT-FXN fusion polypeptide and/or a pharmaceutical composition comprising the disclosed TAT-FXN fusion polypeptide may result in an increase of between about 2-fold and about 5-fold, or between about 2-fold and about 10-fold, in the level of hFXN in at least one tissue or biological fluid of the subject, as compared to the hFXN level in the at least one tissue or biological fluid of the subject prior to administration of the disclosed TAT-FXN fusion polypeptide and/or a pharmaceutical composition comprising the disclosed TAT-FXN fusion polypeptide, or as compared to a baseline level.

In some embodiments, the tissue of a subject in which the level of hFXN may be measured and/or increased may be any tissue that is capable of being biopsied. In some embodiments, the tissue may comprise bronchoalveolar tissue (which may be sampled by, e.g., bronchoalveolar brushing), a mucous membrane (e.g., nasal mucous membrane, which may be sampled by, e.g., nose brushing), a hair follicle, skin tissue, or buccal tissue. In some embodiments, the tissue comprises skin tissue or buccal tissue.

In some embodiments, the biological fluid of a subject in which the level of hFXN may be measured and/or increased may be blood or a component thereof (e.g., serum, plasma, platelets, or any other blood component), urine, or saliva.

FRDA-Associated Pneumonia

Subjects diagnosed with FRDA suffer neurodegeneration of the dorsal root ganglia causing progressive ataxia. This typically leads to the progressive loss of an ability to walk, feed oneself, talk, swallow, and pulmonary aspiration. The event of pulmonary aspiration can lead to pneumonia, frequent hospitalizations, and, eventually, death over a period of 10-15 years from the date of diagnosis.

For many of the reasons set forth above, administration of a disclosed TAT-FXN fusion polypeptide, and/or a pharmaceutical composition comprising a disclosed TAT-FXN fusion polypeptide, can be effective as a protein replacement therapy in FXN-deficient subjects diagnosed with FRDA to prevent pulmonary aspiration, thereby preventing the pneumonia that follows pulmonary aspiration. Accordingly, the present disclosure provides methods of treating an FRDA-associated pneumonia in a subject, comprising administering to a subject in need thereof a TAT-FXN fusion polypeptide of the disclosure, thereby treating the FRDA-associated pneumonia in the subject.

FRDA-Associated Hypertrophic Cardiomyopathy

Hypertrophic cardiomyopathy is a condition in which the muscles of the heart thicken, making it difficult for the heart to pump blood through the circulatory system. It can be caused by a deficiency in FXN in the mitochondria of the heart cells. In subjects diagnosed with FRDA, progressive hypertrophic cardiomyopathy about 50% of the time progresses to heart failure and death. Protein replacement therapy with a disclosed TAT-FXN fusion polypeptide can replace the FXN deficiency underlying hypertrophic cardiomyopathy.

Administration of a disclosed TAT-FXN fusion polypeptide, and/or a pharmaceutical composition comprising a disclosed TAT-FXN fusion polypeptide, can therefore be effective as a protein replacement therapy in FXN-deficient subjects diagnosed with both FRDA and hypertrophic cardiomyopathy. Accordingly, the present disclosure provides methods of treating an FRDA-associated hypertrophic cardiomyopathy in a subject, comprising administering to a subject in need thereof a TAT-FXN fusion polypeptide of the disclosure, thereby treating the FRDA-associated hypertrophic cardiomyopathy in the subject.

Diabetes

The hallmark of diabetes is an inability to properly regulate blood levels of glucose, resulting in elevated blood glucose levels. In subjects diagnosed with FRDA, diabetes often shows up as a consequence of FXN-deficient mitochondria in the pancreas. Protein replacement therapy with a disclosed TAT-FXN fusion polypeptide can replace the FXN deficiency underlying diabetes.

Administration of a disclosed TAT-FXN fusion polypeptide, and/or a pharmaceutical composition comprising a disclosed TAT-FXN fusion polypeptide, can therefore be effective as a protein replacement therapy in FXN-deficient subjects diagnosed with diabetes. Accordingly, the present disclosure provides methods of treating an FRDA-associated diabetes in a subject, comprising administering to a subject in need thereof a TAT-FXN fusion polypeptide of the disclosure, thereby treating the FRDA-associated diabetes in the subject.

Other FRDA-Associated Diseases/Disorders

Subjects diagnosed with FRDA often experience other disorders associated with FXN deficiency. Such FRDA-associated disorders can include, without limitation: neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low high-density lipoprotein (HDL) cholesterol, and elevated low-density lipoprotein (LDL) cholesterol; scoliosis that requires surgery to correct; and/or combinations thereof. Protein replacement therapy with a disclosed TAT-FXN fusion polypeptide can replace the FXN deficiency underlying these diseases/disorders.

Administration of a disclosed TAT-FXN fusion polypeptide, and/or a pharmaceutical composition comprising a disclosed TAT-FXN fusion polypeptide, can therefore be effective as a protein replacement therapy in FXN-deficient subjects diagnosed with FRDA and experiencing neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low HDL cholesterol, and elevated LDL cholesterol; scoliosis that requires surgery to correct; and/or combinations thereof.

Accordingly, the present disclosure provides methods of treating an FRDA-associated disease, disorder or condition, comprising administering to a subject in need thereof a TAT-FXN fusion polypeptide of the disclosure, wherein the FRDA-associated disease, disorder or condition is selected from: neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low HDL cholesterol, and elevated LDL cholesterol; and scoliosis that requires surgery to correct.

In some embodiments, the present disclosure also provides methods of treating FRDA, including, e.g., an FRDA-associated disease, disorder or condition, that comprise administering to a subject in need thereof a pharmaceutical composition comprising a pharmaceutically acceptable vehicle, carrier and/or excipient and the disclosed TAT-FXN fusion polypeptide, e.g., TAT-FXN fusion polypeptide comprising, or consisting of, SEQ ID NO: 1, at a concentration of greater than or equal to 2 mg/mL and a pharmaceutically acceptable vehicle, carrier and/or excipient. For example, the method may comprise administering to a subject in need thereof the pharmaceutical composition as described herein, wherein the disclosed TAT-FXN fusion polypeptide is present in the pharmaceutical composition at a concentration of greater than or equal to: about 2 mg/mL, about 5 mg/mL, about 10 mg/mL, about 15 mg/mL, about 20 mg/mL, about 25 mg/mL, about 30 mg/mL, about 35 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL or about 100 mg/mL. In some embodiments, a disclosed TAT-FXN fusion polypeptide may be present in the pharmaceutical composition at a concentration of about 2.5 mg/mL-about 5 mg/mL, about 4 mg/mL-about 10 mg/mL, about 5 mg/mL-about 25 mg/mL, about 15 mg/mL-about 30 mg/mL, about 20 mg/mL-about 50 mg/mL, about 25 mg/mL-about 60 mg/mL, about 35 mg/mL-about 75 mg/mL, about 50 mg/mL-about 80 mg/mL or about 90 mg/mL-about 100 mg/mL. Alternatively, the disclosed TAT-FXN fusion polypeptide may be present in the pharmaceutical composition at a concentration of about 2.5 mg/mL-about 10 mg/mL, about 5 mg/mL-about 50 mg/mL, about 20 mg/mL-about 75 mg/mL or about 25 mg/mL-about 100 mg/mL. In some embodiments, the methods comprise administering the pharmaceutical composition as described herein, wherein the pharmaceutical composition is an injectable pharmaceutical composition, e.g., suitable for subcutaneous administration.

Administration and Dosing

A disclosed TAT-FXN fusion polypeptide can be administered to a subject by injection. Injection may be intravenous, subcutaneous, intraperitoneal, intramuscular or intradermal. Injectable preparations, for example sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

In various aspects, a disclosed TAT-FXN fusion polypeptide is administered by subcutaneous injection. Subcutaneous injections are typically administered as a bolus into the layer of skin directly below the dermis. As there are few blood vessels in this location, a pharmaceutical ingredient administered to this location will typically release slowly, over time, providing a sustained rate of absorption of a disclosed TAT-FXN fusion polypeptide into the subject.

An injection given intravenously is typically in the range of 5-20 mL in volume. In contrast, an injection given subcutaneously is typically only between 0.05 to 1 mL in volume, typically with a maximum volume of about 1.5 mL, and therefore the concentration of the pharmaceutical ingredient in such an injection must be sufficiently high to achieve a desired therapeutic effect. In that regard, the improved solubility demonstrated by a disclosed TAT-FXN fusion polypeptide is advantageous as it will allow for greater concentration when in solution, thereby accommodating administration via subcutaneous injection.

Administration by injection typically requires a peptide to be formulated in a manner that is pharmaceutically acceptable for injection into a subject, which in some embodiments is a human. In some embodiments, a disclosed TAT-FXN fusion polypeptide is formulated for subcutaneous injection by dissolution in a pharmaceutically acceptable vehicle. In various aspects, the pharmaceutically acceptable vehicle may also include one or more excipients.

There are a number of suitable pharmaceutically acceptable vehicles that may be of use in a pharmaceutical formulation of a disclosed TAT-FXN fusion polypeptide. Suitable vehicles include, for example, water, saline solution, sodium acetate, acetic acid-sodium acetate buffer, phosphate-buffered saline, oil emulsions and the like. The emulsions include oil-in-water emulsions with oil as the dispersed phase and water-in-oil emulsions with oil as the continuous phase. The oil can be of vegetable or origin or synthetically produced. Suitably, the vegetable oil of the emulsions is soybean oil or safflower oil, or any combination thereof. In some embodiments, the vehicle is sodium acetate.

There are a number of suitable pharmaceutically acceptable excipients that may be of use in a pharmaceutical formulation of a disclosed TAT-FXN fusion polypeptide. In some embodiments, the pharmaceutically acceptable excipient is propylene glycol.

Thus, in one aspect the present disclosure provides a pharmaceutical composition for administration to a subject via subcutaneous injection, comprising: (a) a therapeutically effective amount of a disclosed TAT-FXN fusion polypeptide; (b) one or more pharmaceutically acceptable vehicles; and (c) a pharmaceutically acceptable excipient.

The pH of the pharmaceutical composition can vary. In various aspects, it is desirable to maintain the pH of the pharmaceutical composition at physiologic levels, for example at a pH between about 5-7, between about 5-6, between about 5.5-6.5, or between about 6-7. In one embodiment, the pH of the pharmaceutical composition is about 5, about 5.5, about 6, about 6.5 or about 7. In one embodiment, the pH of the pharmaceutical composition is about 5.

A pharmaceutical composition for administration to a subject via subcutaneous injection, can comprise:
(a) a disclosed TAT-FXN fusion polypeptide in an amount selected from 10-100 mg/mL, 10-50 mg/mL, 10 mg/mL and 50 mg/mL;
(b) sodium acetate at a concentration of 50 mM; and
(c) propylene glycol in an amount of 1% of the total volume of the composition;
wherein the pH of the composition is 5.0.

Another pharmaceutical composition can comprise a disclosed TAT-FXN fusion polypeptide at a concentration of greater than or equal to 2 mg/mL and a pharmaceutically acceptable vehicle, carrier and/or excipient. For example, a disclosed TAT-FXN fusion polypeptide may be present in the pharmaceutical composition at a concentration of greater than or equal to: about 2 mg/mL, about 5 mg/mL, about 10 mg/mL, about 15 mg/mL, about 20 mg/mL, about 25 mg/mL, about 30 mg/mL, about 35 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL or about 100 mg/mL. In some embodiments, a disclosed TAT-FXN fusion polypeptide may be present in the pharmaceutical composition at a concentration of about 2.5 mg/mL-about 5 mg/mL, about 4 mg/mL-about 10 mg/mL, about 5 mg/mL-about 25 mg/mL, about 15 mg/mL-about 30 mg/mL, about 20 mg/mL-about 50 mg/mL, about 25 mg/mL-about 60 mg/mL, about 35 mg/mL-about 75 mg/mL, about 50 mg/mL-about 80 mg/mL or about 90 mg/mL-about 100 mg/mL. Alternatively, a disclosed TAT-FXN fusion polypeptide may be present in the pharmaceutical composition at a concentration of about 2.5 mg/mL-about 10 mg/mL, about 5 mg/mL-about 50 mg/mL, about 20 mg/mL-about 75 mg/mL or about 25 mg/mL-about 100 mg/mL. A pharmaceutical composition can be an injectable pharmaceutical composition, which in further embodiments is suitable for subcutaneous administration.

A pharmaceutically acceptable vehicle may be an aqueous vehicle, such as, for example, water, a saline solution or an aqueous buffer, such as an acetate buffer or a phosphate buffer. A disclosed TAT-FXN fusion polypeptide present in the pharmaceutical composition is fully dissolved in the pharmaceutically acceptable vehicle. The term "fully dissolved in the pharmaceutical composition", as used herein, refers to a pharmaceutical composition that comprises a disclosed TAT-FXN fusion polypeptide and that is a clear solution and/or does not comprise a visible precipitate.

Preparation of a pharmaceutical composition comprising a disclosed TAT-FXN fusion polypeptide comprises a concentration of greater than or equal to 2 mg/mL is based on the surprising discovery that a disclosed TAT-FXN fusion polypeptide demonstrates significantly higher solubility (e.g., solubility in an aqueous solution) than the Vyas et al. polypeptide. For example, as mentioned above, it is possible to prepare compositions (e.g., aqueous compositions) comprising a disclosed TAT-FXN fusion polypeptide at concentrations of at or greater than about 50 mg/mL. In contrast, the Vyas et al. polypeptide cannot exceed about 2 mg/mL before the Vyas polypeptide precipitates out of solution.

The pharmaceutical compositions provided herein comprise a disclosed TAT-FXN fusion polypeptide at a concentration of greater than or equal to 2 mg/mL, allow for administration of a disclosed TAT-FXN fusion polypeptide to a subject by subcutaneous injection in an amount of greater than or equal to 2 mg/injection. For example, a disclosed TAT-FXN fusion polypeptide may be administered by subcutaneous injection to a subject in an amount greater than or equal to: 2 mg/injection, 5 mg/injection, 10 mg/injection, 15 mg/injection, 20 mg/injection, 25 mg/injection, 30 mg/injection, 35 mg/injection, 40 mg/injection, 45 mg/injection, 50 mg/injection, 55 mg/injection, 60 mg/injection, 65 mg/injection, 70 mg/injection, 75 mg/injection, 80 mg/injection, 85 mg/injection, 90 mg/injection, 95 mg/injection or 100 mg/injection. For example, a disclosed TAT-FXN fusion polypeptide may be administered by subcutaneous injection to a subject in an amount of about 2 mg/injection-about 150 mg/injection, about 2 mg/injection-about 100 mg/injection, about 10 mg/injection-about 150 mg/injection, about 20 mg/injection-about 150 mg/injection, 2.5 mg/injection-about 5 mg/injection, about 4 mg/injection-about 10 mg/injection, about 5 mg/injection-about 25 mg/injection, about 15 mg/injection-about 30 mg/injection, about 20 mg/injection-about 50 mg/injection, about 25 mg/injection-about 60 mg/injection, about 35 mg/injection-about 75 mg/injection, about 50 mg/injection-about 80 mg/injection, about 90 mg/injection-about 120 mg/injection, and/or about 100 mg/injection-about 150 mg/injection. A disclosed TAT-FXN fusion polypeptide may be present in the pharmaceutical composition at a concentration of about 2.5 mg/injection-about 10 mg/injection, about 5 mg/injection-about 50 mg/injection, about 20 mg/injection-about 75 mg/injection, about 25 mg/injection-about 100 mg/injection or about 50 mg/injection-about 150 mg/injection.

In some embodiments, a pharmaceutical composition provided by the present invention may comprise a TAT-FXN fusion polypeptide and a pharmaceutically acceptable carrier, wherein the fusion polypeptide may be present in the pharmaceutical composition at a concentration of greater than about 4 mg/mL; and wherein the fusion polypeptide may comprise or consist of a first peptide comprising a cell penetrant peptide (CPP); and a second peptide having an amino acid sequence with at least about 90% sequence identity, e.g., at least about 95%, at least about 99% or about 100% sequence identity, to the amino acid sequence of SEQ ID NO: 4. In some embodiments, a pharmaceutical composition provided by the present invention may comprise a TAT-FXN fusion polypeptide and a pharmaceutically acceptable carrier, wherein the fusion polypeptide may be present in the pharmaceutical composition at a concentration of greater than about 4 mg/mL; and wherein the fusion polypeptide may comprise or consist of a first peptide comprising a cell penetrant peptide (CPP); a second peptide having an amino acid sequence with at least 90% sequence identity, e.g., at least about 95%, at least about 99% or about 100% sequence identity, to the amino acid sequence of SEQ ID NO: 3; and a third peptide having an amino acid sequence with at least 90% sequence identity, e.g., at least about 95%, at least about 99% or about 100% sequence identity, to the amino acid sequence of SEQ ID NO: 5.

Cell penetrant peptides (CPPs) are short peptide sequences, typically between 5 and 30 amino acids long, that can facilitate cellular intake of various molecular cargo, such as proteins. A CPP useful in the context of the present disclosure may be any CPP known to a person skilled in the art. For example, a CPP comprised in the fusion polypeptides of the present disclosure may be any CPP listed in the Database of Cell-Penetrating Peptides CPPsite 2.0, the entire contents of which are hereby incorporated herein by reference. In some embodiments, a CPP useful in the context of the present disclosure may comprise an aromatic cationic peptide as described, e.g., in U.S. Pat. No. 10,576,124, the entire contents of which are hereby incorporated herein by reference. For example, an aromatic cationic peptide may be 2', 6' dimethyl-Tyr-D-Arg-Phe-Lys-NH$_2$. In some embodiments, a CPP useful in the context of the present invention may be selected TAT-cpp (e.g., SEQ ID NO: 2 or SEQ ID NO: 7), galanin, mastoparan, transportan, penetratin, polyarginine, or VP22.

A pharmaceutical composition provided by the present disclosure may comprise a TAT-FXN fusion polypeptide and a pharmaceutically acceptable carrier, wherein the fusion polypeptide may be present in the pharmaceutical composition at a concentration of greater than about 4 mg/mL; and wherein the fusion polypeptide may comprise or consist of a first peptide having an amino acid sequence with at least about 90% sequence identity, e.g., at least about 95%, at least about 99% or about 100% sequence identity, to the amino acid sequence of SEQ ID NO: 2 or SEQ ID NO: 7; and a second peptide having an amino acid sequence with at least about 90% sequence identity, e.g., at least about 95%, at least about 99% or about 100% sequence identity, to the amino acid sequence of SEQ ID NO: 4.

In some embodiments, a pharmaceutical composition provided by the present disclosure may comprise a TAT-FXN fusion polypeptide and a pharmaceutically acceptable carrier, wherein the fusion polypeptide may be present in the pharmaceutical composition at a concentration of greater than about 4 mg/mL and wherein the fusion polypeptide may comprise or consist of a first peptide having an amino acid sequence with at least 90% sequence identity, e.g., at least about 95%, at least about 99% or about 100% sequence identity, to the amino acid sequence of SEQ ID NO: 2 or SEQ ID NO: 7; a second peptide having an amino acid sequence with at least 90% sequence identity, e.g., at least about 95%, at least about 99% or about 100% sequence identity, to the amino acid sequence of SEQ ID NO: 3; and a third peptide having an amino acid sequence with at least 90% sequence identity, e.g., at least about 95%, at least about 99% or about 100% sequence identity, to the amino acid sequence of SEQ ID NO: 5.

In some embodiments, the fusion polypeptide may further comprise a linker of 1, 2 or 3 amino acids disposed between the first and second peptides, e.g., a 2-amino acid linker, such as Gly-Gly.

Dosing of a disclosed TAT-FXN fusion polypeptide may vary from subject to subject, based on an individual subject's sensitivity to a disclosed TAT-FXN fusion polypeptide, tolerance to the amount dosed over time, and the like. Generally, the amount of a disclosed TAT-FXN fusion polypeptide administered to a subject can range from about 5 mg $kg^{-1}$ to about 60 mg $kg^{-1}$ per day, based on the milligrams of the active composition in a given formulation per kilogram of the subject's body weight. The total dose may be administered at once, as a single dose, or may be split among two or more doses, administered multiple times per day, as necessary to affect a desired therapeutic effect. In some cases, three or more doses of a disclosed TAT-FXN fusion polypeptide may be administered to a given patient in any one 24 our period; fewer doses may be administered to patients who respond well to the therapy.

Generally, a subject will be administered a starting dose that is regarded as safe by a health care provider, and the dose will be titrated up or down, based on the individual subject's tolerance and tissue levels of FXN to achieve a desired therapeutic effect. For example, a recommended starting dose for a subject may be 30 mg $kg^{-1}$, administered subcutaneously 3 times per day. The health care provider will administer this dose and then monitor levels of a disclosed TAT-FXN fusion polypeptide by taking skin biopsies and measuring the amount of a disclosed TAT-FXN fusion polypeptide present therein. The amount present will be compared to a known baseline, for example that as seen in a healthy subject, and the dose of a disclosed TAT-FXN fusion polypeptide will be titrated incrementally or decrementally as needed to maintain skin levels at a target amount and/or to achieve a desired therapeutic benefit, up to a maximum dose of 60 mg $kg^{-1}$ daily. A dose can be titrated at 1-day, 1-week, or longer intervals.

In some embodiments, a TAT-FXN fusion polypeptide of the present disclosure may be administered to a subject at a dose of about 10-mg to about 150 mg, e.g., about 10 mg to about 30 mg, about 20 mg to about 75 mg, about 50 mg to about 100 mg, or about 100 mg to about 150 mg. For example, the TAT-FXN fusion polypeptide may be administered to a subject at a dose of about 25 mg, about 50 mg, about 75 mg, about 100 mg or about 150 mg. In some embodiments, the dose may be administered once per day. In some embodiments, a TAT-FXN fusion polypeptide of the present disclosure may be administered to a subject at a dose of about 5 mg $kg^{-1}$ to about 60 mg $kg^{-1}$ per day, e.g., about 10 mg $kg^{-1}$ to 50 mg $kg^{-1}$ per day, about 20 mg $kg^{-1}$ to 40 mg $kg^{-1}$ per day, about 30 mg $kg^{-1}$ to 40 mg $kg^{-1}$ per day, about 40 mg $kg^{-1}$ to 50 mg $kg^{-1}$ per day, about 50 mg $kg^{-1}$ to 60 mg $kg^{-1}$ per day, about 5 mg $kg^{-1}$ to 10 mg $kg^{-1}$ per day, about 10 mg $kg^{-1}$ to 15 mg $kg^{-1}$ per day, about 15 mg $kg^{-1}$ to 20 mg $kg^{-1}$ per day, about 20 mg $kg^{-1}$ to 25 mg $kg^{-1}$ per day, about 25 mg $kg^{-1}$ to 30 mg $kg^{-1}$ per day, about 30 mg $kg^{-1}$ to 35 mg $kg^{-1}$ per day, about 35 mg $kg^{-1}$ to 40 mg $kg^{-1}$ per day, about 40 mg $kg^{-1}$ to 45 mg $kg^{-1}$ per day, about 45 mg $kg^{-1}$ to 50 mg $kg^{-1}$ per day, about 50 mg $kg^{-1}$ to 55 mg $kg^{-1}$ per day, and about 55 mg $kg^{-1}$ to 60 mg $kg^{-1}$ per day. In some embodiments, a TAT-FXN fusion polypeptide of the present disclosure may be administered to a subject at a dose of about 0.05 mg $kg^{-1}$ to about 20 mg $kg^{-1}$ per day, e.g., about 0.05 mg $kg^{-1}$ to 0.5 mg $kg^{-1}$ per day, about 0.1 mg $kg^{-1}$ to 1 mg $kg^{-1}$ per day, about 0.5 mg $kg^{-1}$ to 5 mg $kg^{-1}$ per day, about 1 mg $kg^{-1}$ to 10 mg $kg^{-1}$ per day, about 2 mg $kg^{-1}$ to 15 mg $kg^{-1}$ per day, about 5 mg $kg^{-1}$ to 15 mg $kg^{-1}$ per day or about 10 mg $kg^{-1}$ to about 10 mg $kg^{-1}$ per day.

In addition to the skin biopsies referenced above, criteria for determining the effective dose for a given subject include monitoring the symptoms displayed and/or reported by the subject during treatment. Prior to commencing treatment with a disclosed TAT-FXN fusion polypeptide, subjects will undergo, or will have already undergone, an extensive medical evaluation. A typical medical evaluation for subjects diagnosed with Friedreich's Ataxia may include measuring one or more of the following: neurologic function, cardiac function, gross and fine motor skills, hearing, speech, vision, blood work for diabetes, and swallowing.

The results of evaluations performed before treatment may serve as baseline for evaluating the effectiveness of the administered treatment. This 'baseline' evaluation may be part of the process of designing and adjusting a proper dosing regimen for any given subject. The administered dose can be increased or decreased as necessary to affect a desirable therapeutic effect in a subject. Elements of the dosing evaluation may include feedback from the subject regarding changes in mobility, balance, sensation, mood, fatigue, stamina, strength, and any other physiological or psychological trait associated with a diagnosis of Friedreich's Ataxia.

The pharmaceutical compositions provided by the present disclosure may be formulated in consideration of any one or more of the following: ease of storage, transportation, stability and patient convenience. Formulations may include preloaded syringes, vial, bottle, and the like. In some embodiments, a disclosed TAT-FXN fusion polypeptide may be lyophilized and placed into a sterile vial for storage and/or transportation. To generate a pharmaceutical composition, the lyophilized peptide may be admixed with a sterile vehicle, sterile excipient to create a pharmaceutical composition suitable for subcutaneous administration.

A TAT-FXN fusion polypeptide or a pharmaceutical composition can be used in the manufacture (i.e., preparation) of a medicament for administration to a subject. The medicament is a therapeutic composition including a TAT-FXN fusion polypeptide. The pharmaceutical composition can be the same as the medicament.

EXAMPLES

Example 1

The primary objective of this study was to determine if a disclosed TAT-FXN fusion polypeptide can significantly extend the lifespan of the MCK-Cre FXN KO mouse (also known as MCK-Cre), a murine model of Friedreich's ataxia (FRDA), as compared with Vehicle-treated mice of the same genotype. Mice of this genotype have the FRDA gene ablated in heart and skeletal muscle, and thus, are deficient in frataxin (FXN) in these tissues. These mice exhibit the cardiac phenotype of FRDA including severe hypertrophic cardiomyopathy, which is responsible for the reduced survival compared to wild-type mice.

Methods and Procedures
FRDA Mouse Model

Mouse breeding was as follows: Mice conditional for ablation of exon 4 of the FRDA gene in heart and skeletal muscle were generated using transgenic mice containing the MCK-Cre transgene (Jax Labs B6.FVB(129S4)-Tg(Ckmmcre)5 Khn/J) crossed with mice homozygous for a conditional allele of Frda floxed at exon 4 (termed Frda$^{L3/L3}$) to generate the genotype MCK-Cre Frda$^{L3/Wt}$. These mice were then crossed back into the Frda$^{L3/L3}$ line to generate the final conditional genotype of MCK-Cre Frda$^{L3/L3}$ (termed MCK-Cre FXN KO). These mice develop a hypertrophic cardiomyopathy by 45 days of age that closely mimics the human heart in FRDA, which evolves into a dilated cardiomyopathy by ~65 days of age. The mice die from heart failure by ~85 days of age.

Test and Control Articles

Test article: the TAT-FXN fusion polypeptide (SEQ ID NO: 1, FIG. 5), a 224-amino acid, recombinant fusion protein consisting of the cell-penetrant peptide TAT fused through a di-peptide (Gly-Gly) linker to the amino-terminus of the complete human frataxin (hFXN) cDNA sequence (FujiFilm Diosynth batch #NBA0838-24). This was formulated for subcutaneous administration by FujiFilm Diosynth at a concentration of 10 mg/ml in 50 mM NaOAC, 1% propylene glycol (pH 5.0). This dosing solution was sterile filtered, stored at −80° C. in 1.8 mL aliquots and used for all dosing in this study. FujiFilm Diosynth determined that this formulation is stable at room temperature for at least 7 days. However, stability was not determined for conditions used in this study (i.e., sterile filtered and stored at −80° C.).

Control article: Vehicle, composed of 50 mM NaOAC, 1% Ppropylene glycol, pH 5.0, sterile filtered, and stored at −80° C. in 1.8 mL aliquots until use.

Experimental Protocol

MCK-Cre FXN KO mice entered the trial at 15±1 days of age. Eight males and 8 females were treated with 10 mg/kg of the TAT-FXN fusion polypeptide (SEQ ID NO: 1) via the subcutaneous route three times/week. Eight males and 7 females were treated with Vehicle via the subcutaneous route three times/week. Subjects were weighed prior to dosing and the dose volumes of test article or vehicle were adjusted for body weight (1 μl/g). Subjects were dosed up to 170 days of life per approved animal protocol; however, mice surviving beyond 170 days of life continued to receive treatment until they died or were removed from study by 200 days.

Mice were examined for clinical signs, including mortality, daily. Animals found dead and animals who survived to the end of treatment were necropsied and tissues were harvested and stored for further analysis.

Data were analysed using Student's t-test, or by Kaplan-Meier Survival curve with log rank analysis.

Results

MCK-Cre FXN KO mice treated with the TAT-FXN fusion polypeptide lived significantly longer than mice treated with Vehicle (FIG. 1, Tables 1 and 2). At the end of the study period (mice age 170 days), none of the 15 Vehicle-treated mice were alive while 8 of the 16 mice treated with the TAT-FXN fusion polypeptide were alive. In the group of mice treated with the TAT-FXN fusion polypeptide surviving longer than 170 days of life, 3 were male and 5 were female indicating there was no remarkable sex difference in survival. By Log Rank analysis (stringent), treatment with the TAT-FXN fusion polypeptide significantly increased (p=0.001) lifespan of MCK-Cre FXN KO mice compared to treatment with Vehicle. The median survival for mice treated with the TAT-FXN fusion polypeptide was 166 days and was 98 days for Vehicle-treated mice. The mean survival for Vehicle-treated mice was 107.5 days: 33% of Vehicle-treated mice survived beyond the mean age of 107.5 days, whereas 87.5% of mice treated with the TAT-FXN fusion polypeptide survived beyond this time.

Figure 2A:
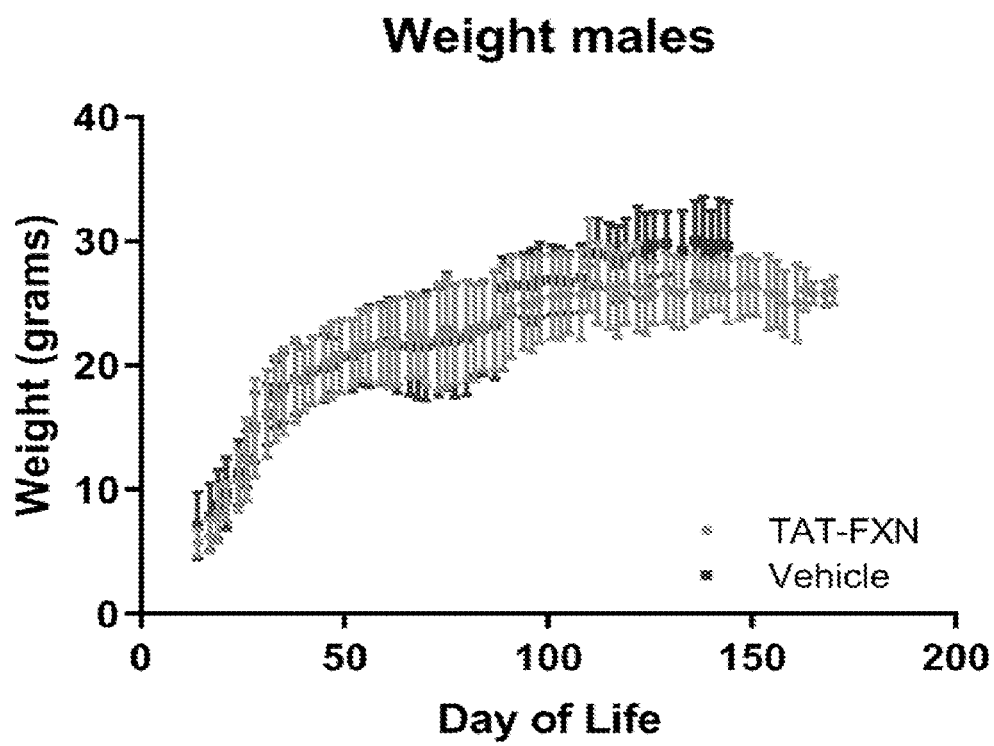
FIG. 2A illustrates weight gain in male MCK-Cre FXN KO mice treated with the TAT-FXN fusion polypeptide provided by the present disclosure (SEQ ID NO: 1) (10 mg/kg, SC, 3×per week) or Vehicle (1 µl/g, SC 3×per week) from day 15 to day 170 of life. DOL=days of life.
Figure 2B:
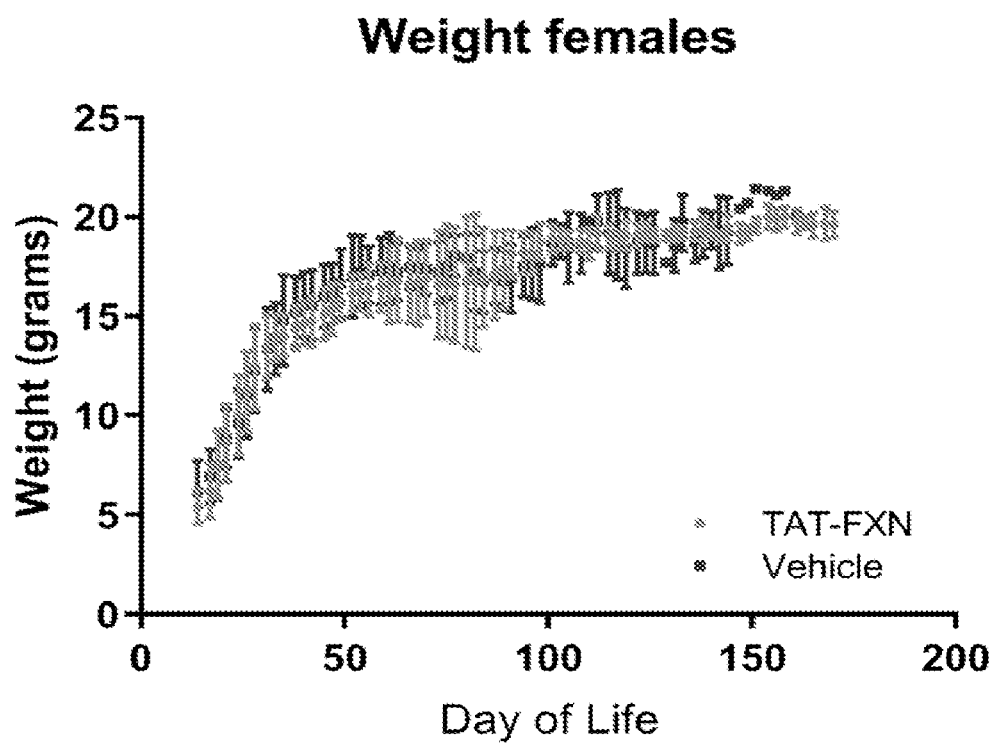
FIG. 2B illustrates weight gain in female MCK-Cre FXN KO mice treated with the TAT-FXN fusion polypeptide provided by the present disclosure (SEQ ID NO: 1) (10 mg/kg, SC, 3×per week) or Vehicle (1 µl/g, SC 3×per week) from day 15 to day 170 of life. DOL=days of life.

The body weight gains for both male and female animals during the study were recorded and plotted (FIGS. 2A and 2B). Body weights of males treated with the TAT-FXN fusion polypeptide were compared with body weights of males treated with Vehicle (FIG. 2A), and females were analyzed in the same manner (FIG. 2B). Results demonstrate that there were no remarkable differences between the group treated with the TAT-FXN fusion polypeptide and the Vehicle-treated group in the body weight gain over time in either sex.

Results of this study demonstrate that the TAT-FXN fusion polypeptide can improve survival in the MCK-Cre FXN KO mouse model of FRDA. This finding confirms and extends the published report that use of a transactivator of transcription (TAT) protein transduction domain to deliver human FXN protein to mitochondria improves survival in mouse FRDA models (Vyas et al., supra). In the previous study, the NSE-Cre transgene was used to drive tissue specific ablation of the FRDA gene in brain and neural tissues, and heart (see Puccio et al., Nat Genet. 2001; 27(2): 181-186) versus ablation of the FRDA gene in heart and skeletal muscle in the current MCK-Cre FXN KO mouse model. The two models differed in that survival in Vehicle-treated mice was shorter in the NSE-Cre FXN KO model (average lifespan of 27.5+2.3 days in the NSE-Cre FXN KO model versus median survival of 98 days in the MCK-Cre FXN KO model) and a decrease in body weight gain was evident in the NSE-Cre FXN KO model but not in the MCK-Cre FXN KO model. Although the dose levels used for FXN replacement were identical, the studies also differed in the route of administration. In the first study, the intraperitoneal route was used and in the current study, the route of administration was subcutaneous. In these studies, the Vyas et al. polypeptide and their disclosed TAT-FXN fusion polypeptide increased median survival by approximately 49% and 70%, respectively. Therefore, the cell-penetrant peptide, referred to herein as the TAT-FXN fusion polypeptide, is capable of delivering a replacement protein, FXN, to mitochondria in vivo in amounts sufficient to rescue a very severe (fatal) disease phenotype in a subject KO mouse model.

Treatment of the MCK-Cre FXN KO mouse with 10 mg/kg SC of the TAT-FXN fusion polypeptide (SEQ ID NO: 1) three times a week was well tolerated and extended lifespan when compared with the Vehicle-treated mice.

Pvalb-Cre FXN KO

Studies examining the TAT-FXN fusion polypeptide in a neurological model of FRDA were conducted. These experiments allow for the study of the neurologic components of FRDA in the mouse without the overlay of heart or muscle dysfunction. Conditional loss of the Frda gene is driven by the Parvalbumin-Cre (Pvalb-Cre) transgene (Jax Labs B6; 129P2-Pvalb$^{tm1(cre)Arbr}$/J) following the same breeding strategy as the MCK-Cre FXN-KO (above) causing ablation of the Frda gene only in brain, spinal cord, and dorsal root ganglia. Briefly, the Pvalb-Cre$^+$ mice are crossed into the Frda$^{L3/L3}$ line to generate the genotype Pvalb-Cre$^+$::Frda$^{L3/Wt}$. These mice are then crossed back into the Frda$^{L3/L3}$ line to generate the final genotype of Pvalb-Cre$^+$::Frda$^{L3/L3}$, also termed PVKO. These mice develop a significant neurologic phenotype at ~90 days of age consisting of ataxic gait, impaired motor skills, loss of proprioception, and eventually death due to the inability to feed or drink by ~130-140 days of age.

Figure 3:
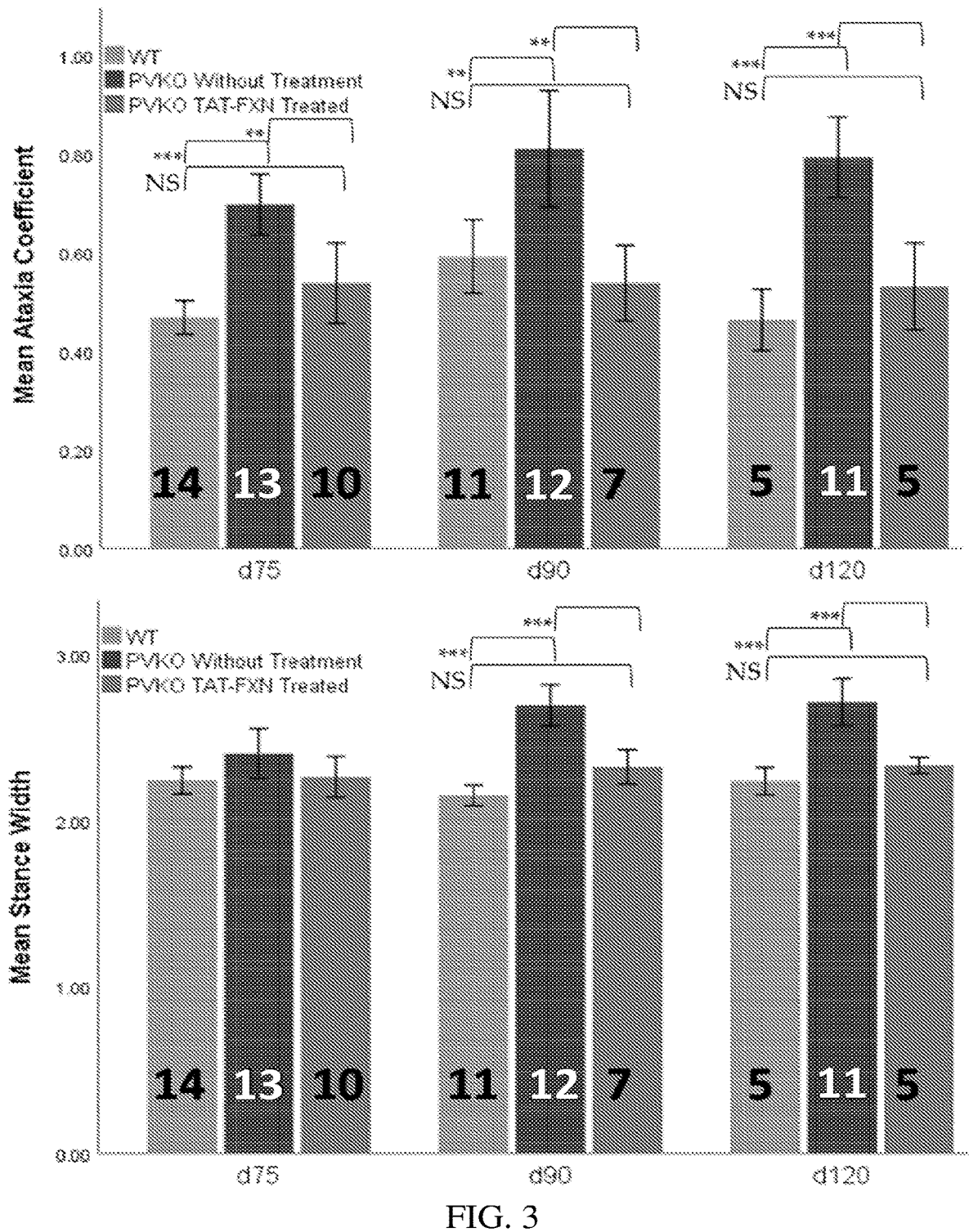
FIG. 3 illustrates mean Ataxia Coefficient and Mean Stance Width between wild-type (WT) mice, parvalbumin-deficient (PVKO) mice, and parvalbumin-deficient mice treated with the TAT-FXN fusion polypeptide provided by the present disclosure (SEQ ID NO: 1), which delivers the frataxin protein to the mitochondria (PVKO+TAT-FXN). These mice are a model for the progressive neurological ataxia of FRDA. Number of mice for each group shown within bars. Data is presented +/−SEM (p values: *<0.05, <0.01, *<0.0001). The TAT-FXN fusion polypeptide provided by the present disclosure contains no known glycosylation or other posttranslational modifications.

Three groups of mice were studied for 120 days. Wild Type mice (WT, n=14) and a group of untreated KO mice (n=13) were compared with a group of treated KO mice (n=10). The treated group received 10 mg kg$_{-1}$ intraperitoneal (IP) of the TAT-FXN fusion polypeptide (SEQ ID NO: 1) three times a week starting at 7 days of age, whereas the WT and untreated KO mice did not receive the TAT-FXN fusion polypeptide. The animal's ability to walk was assessed using a DigiGait (Mouse Specifics, Inc, Framingham, MA), which contains a transparent treadmill belt that digitally captures gait data while the mice walk at 20 cm/sec. Mice were walked at day of life 30, 45, 60, 75, 90, and 120. The data were then analyzed using proprietary software and 41 outcome measures are reported. Animals were lost at the 90 and 120-day timepoints due to DigiGait equipment breakdown and thus, later timepoints have smaller groups. No animals died during the study. Additionally, all animals were longitudinally followed from day 30 to day 120. Preliminary results showed that the WT animals differed over time from the untreated KO mice for approximately 14 of the 41 analyzed variables. Twenty-seven variables were not different between WT and untreated KO and were discarded as not informative. When the treated animals were compared to the untreated animals for those 14 parameters the treated animals did better than the untreated animals for multiple variables but were highly significant for Stance Width, Ataxia Coefficient, and Midline Distance (see FIG. 3). Of these 3 behavioural biomarkers, Stance Width and Ataxia Coefficient are directly translatable to human gait whereas Midline Distance is relevant to rodents. Treated PVKO mice lived significantly longer than untreated mice (FIG. 4) and the trial was terminated at 180 days per approved animal protocol. These data show statistically significant improvement in behavioural biomarkers of gait, and in lifespan, when PVKO mice are treated with the TAT-FXN fusion polypeptide.

Example 2

The primary objective of this study is to demonstrate that the TAT-FXN fusion polypeptide (SEQ ID NO: 1) can be purified in a single step process.

As noted above, purification of the Vyas et al. polypeptide depends upon a 6×His tag (SEQ ID NO: 11) at its aminoterminus. This markedly complicates purification, because additional proteins will be pulled down with the Vyas et al. polypeptide. This requires multiple additional purification steps and/or chromatography in order to separate the Vyas et al. polypeptide from these other peptides.

The TAT-FXN fusion polypeptide does not contain a His tag and thus does not rely on it for purification (see FIG. 5). Purification of the disclosed TAT-FXN fusion polypeptide will therefore be faster, easier and less expensive than purification of the Vyas et al. polypeptide.

Figure 6A:
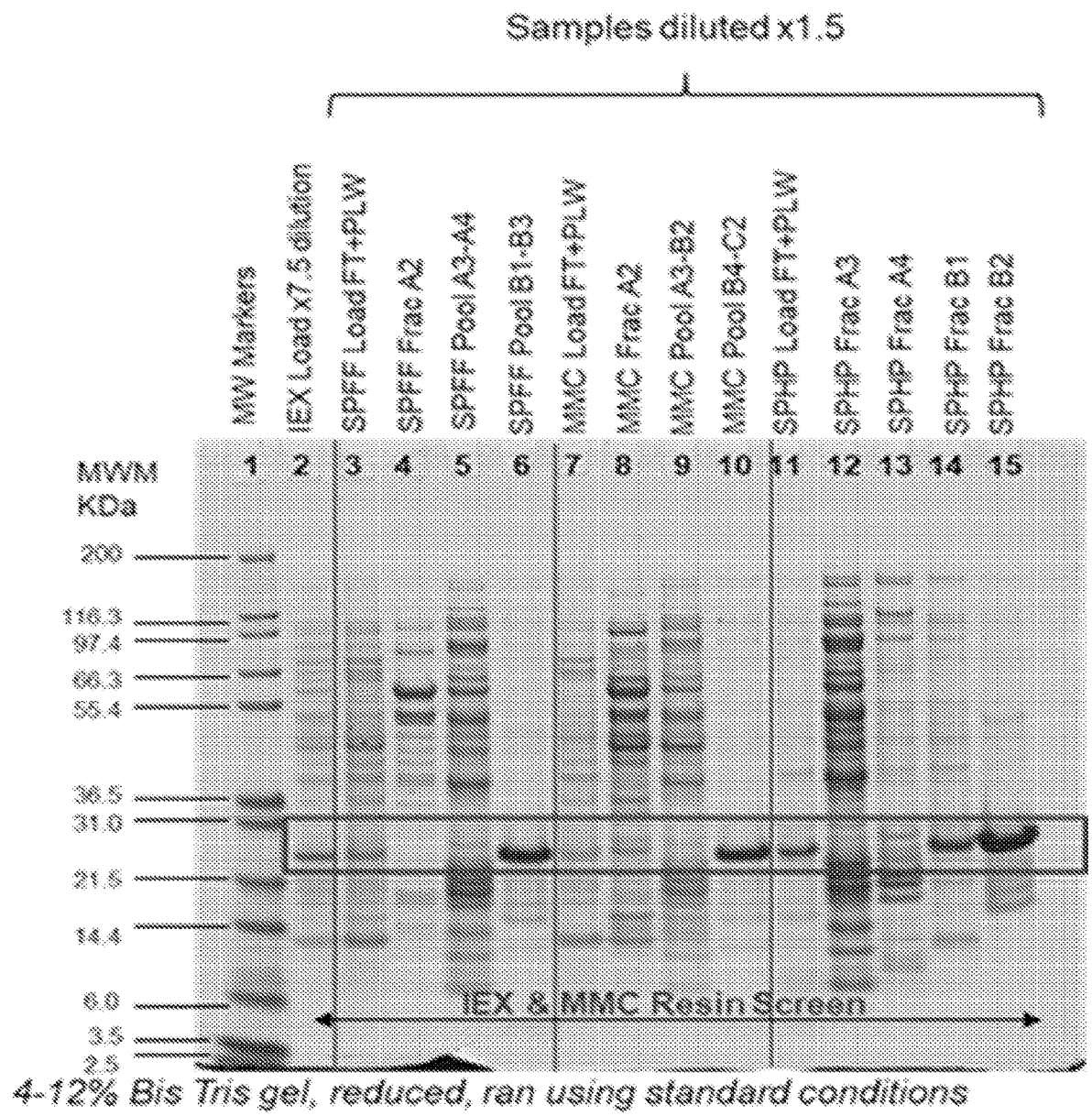
FIG. 6A illustrates the results of a purification optimization study utilizing a 4-12% bis-tris gel, reduced, run under standard conditions. Fourteen preparations of the TAT-FXN fusion polypeptide (SEQ ID NO: 1) were generated using four different chromatography purification techniques. The box shows the TAT-FXN fusion polypeptide. IEX=ion exchange chromatography resin; SPFF=Sepharose® fast flow resin; MMC=capto-MMC chromatography media; SPHP=Sepharose® high performance resin.

FIG. 6A depicts a purification optimization study performed utilizing a 4-12% bis-tris gel, reduced, ran under standard conditions. This study was designed to determine the best single-step chromatography matrix and conditions for the TAT-FXN fusion polypeptide. Fourteen preparations of the TAT-FXN fusion polypeptide were generated using four different chromatography purification techniques. The box shows the TAT-FXN fusion polypeptide isolated from: ion exchange chromatography resin (IEX, 1 sample), Sepharose® fast flow resin (SPFF, 4 samples), capto-MMC chromatography media (MMC, 4 samples), and sepharose high performance resin (SPHP, 5 samples).

Based on these data, it is clear that single-step purification with capto-MMC chromatography media is more than adequate for initial, single-step purification of the TAT-FXN fusion polypeptide. Endotoxin removal then follows, using a commercial STIC column, which purifies the TAT-FXN fusion polypeptide even further.

Figure 6B:
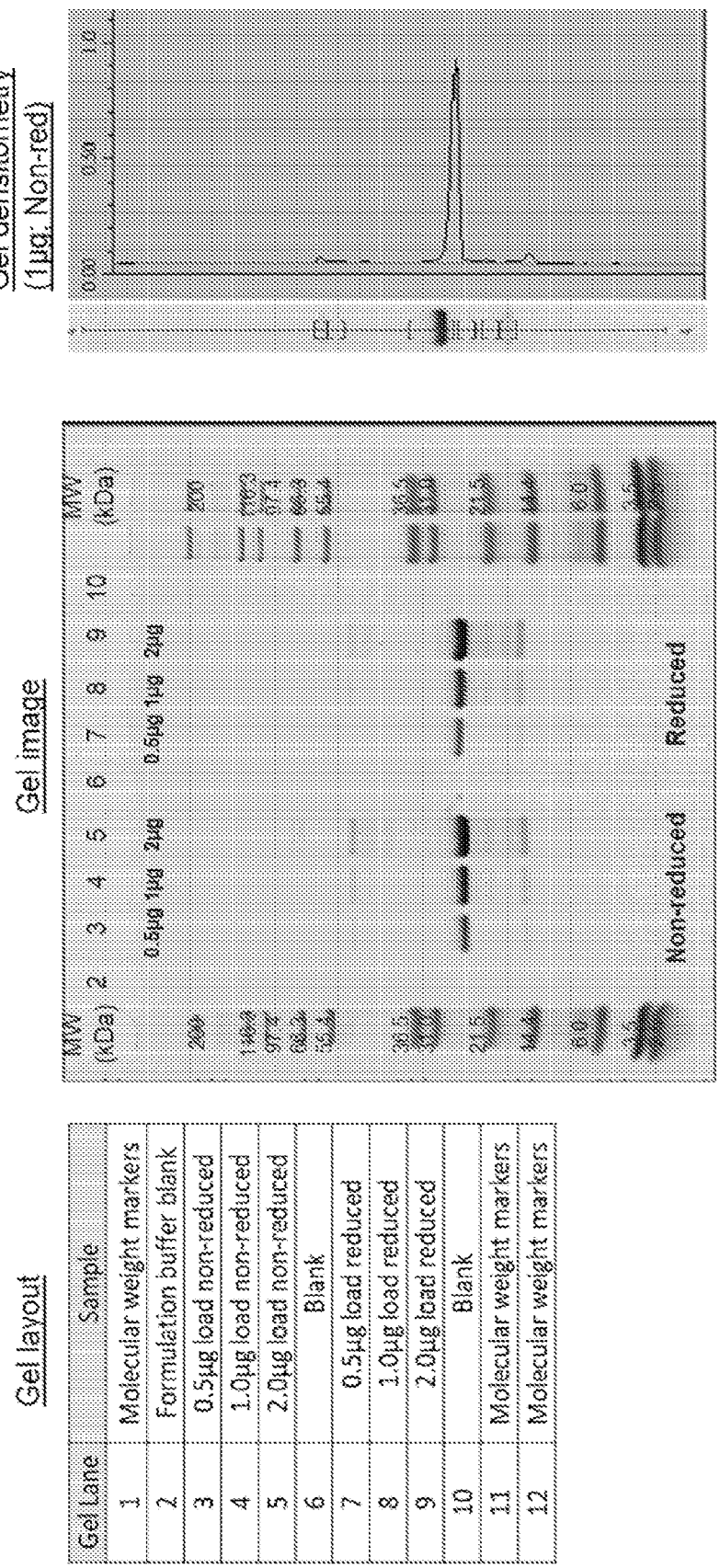
FIG. 6B depicts the results of a purity analysis of the TAT-FXN fusion polypeptide (SEQ ID NO: 1) isolated via capto-MMC chromatography media.

FIG. 6B depicts further analysis of the TAT-FXN fusion polypeptide, purified using capto-MMC media as shown in FIG. 6A. These conditions show excellent purity of the TAT-FXN fusion polypeptide at about 90%, using only single-step isolation followed by endotoxin removal.

Example 3

The objective of this study was to determine whether, and to what extent, the TAT-FXN fusion polypeptide would target the mouse brain, spinal cord and heart.

Figure 7A:
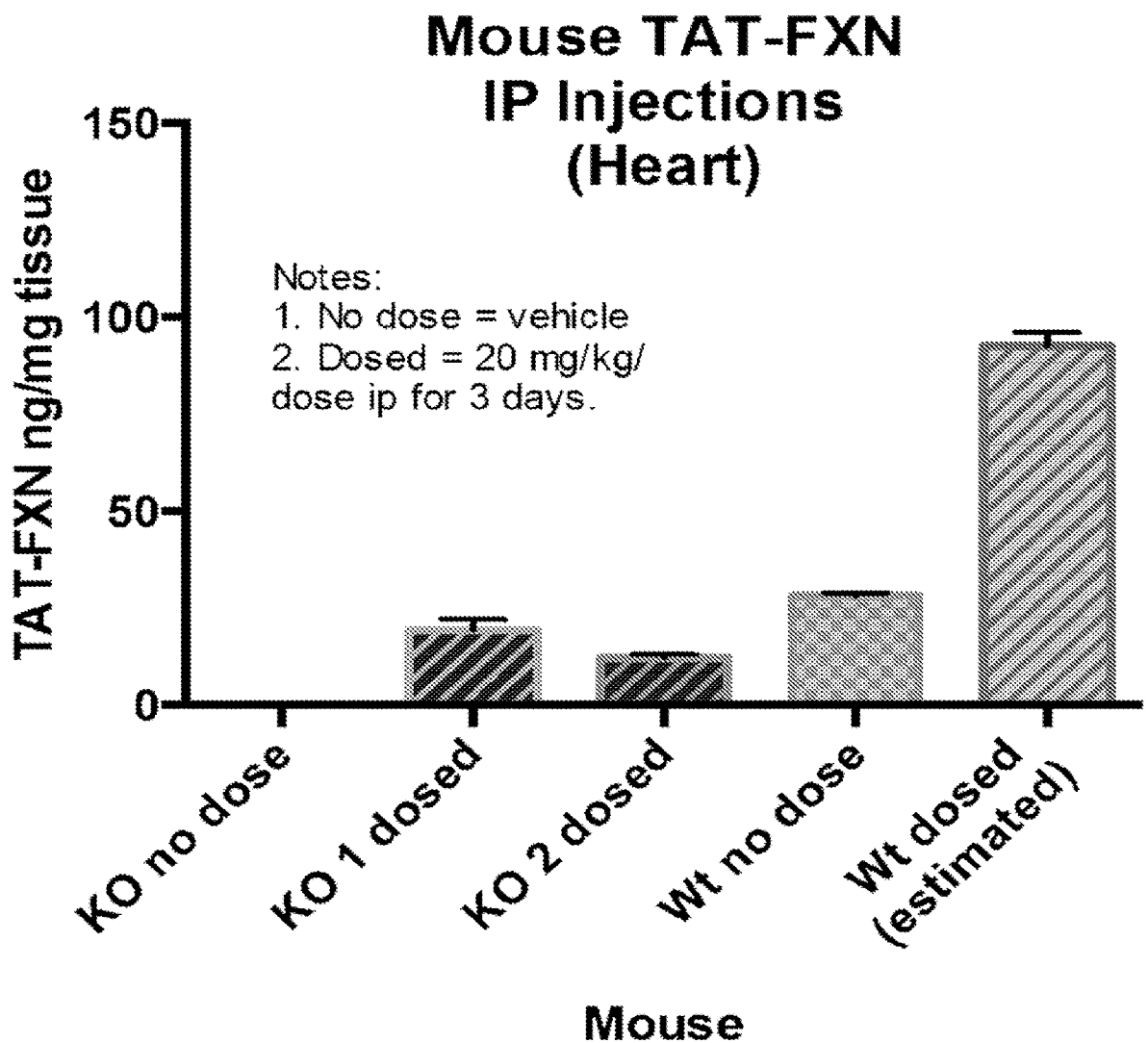
FIG. 7A illustrates tissue penetration of the TAT-FXN fusion polypeptide (SEQ ID NO: 1) into mouse heart, as described in Example 3.

Tissue penetration of the TAT-FXN fusion polypeptide into mouse heart is shown in FIG. 7A. Heart is a target tissue for treatment in FRDA. Here, three MCK-Cre FXN KO mice at 50 days of age were injected either with the TAT-FXN fusion polypeptide intraperitoneal (ip) at a dose of 20 mg/kg for 3 consecutive days, or an equivalent volume of vehicle (carrier fluid). For comparison, a wild type (Wt) mouse was also injected with vehicle for 3 days, and a second Wt mouse was injected with the TAT-FXN fusion polypeptide for 3 days ip at 20 mg/kg. At the end of this time, the hearts were removed, homogenized, and assayed by ELISA (Abcam, Cambridge, MA) for the presence of FXN. As expected, the MCK-Cre FXN KO no-dose mouse had no signal for FXN in its heart. This confirms that FXN expression in the heart of the KO mouse is truly knocked out. Both KO 1 and KO 2 dosed animals had about 15-20 ng/mg total protein of FXN in their hearts. The Wt mouse that was not dosed (Wt no dose) had a FXN signal equivalent to about 25 ng/mg total protein of native FXN. For the Wt mouse that was dosed with TAT-FXN, the signal was additive (native FXN+TAT-FXN) to generate total FXN mass of about 90 ng/mg total heart protein. These data demonstrate that the TAT-FXN peptide sequence penetrates quite well into the knockout heart at levels of about 50-75% of native FXN expression.

The conclusion to be drawn from these data is that single daily dosing via the intraperitoneal route achieves near normal levels of FXN when compared with wild type mouse. Injection into wild type mouse gives very high levels of FXN in the heart.

Figure 7B:
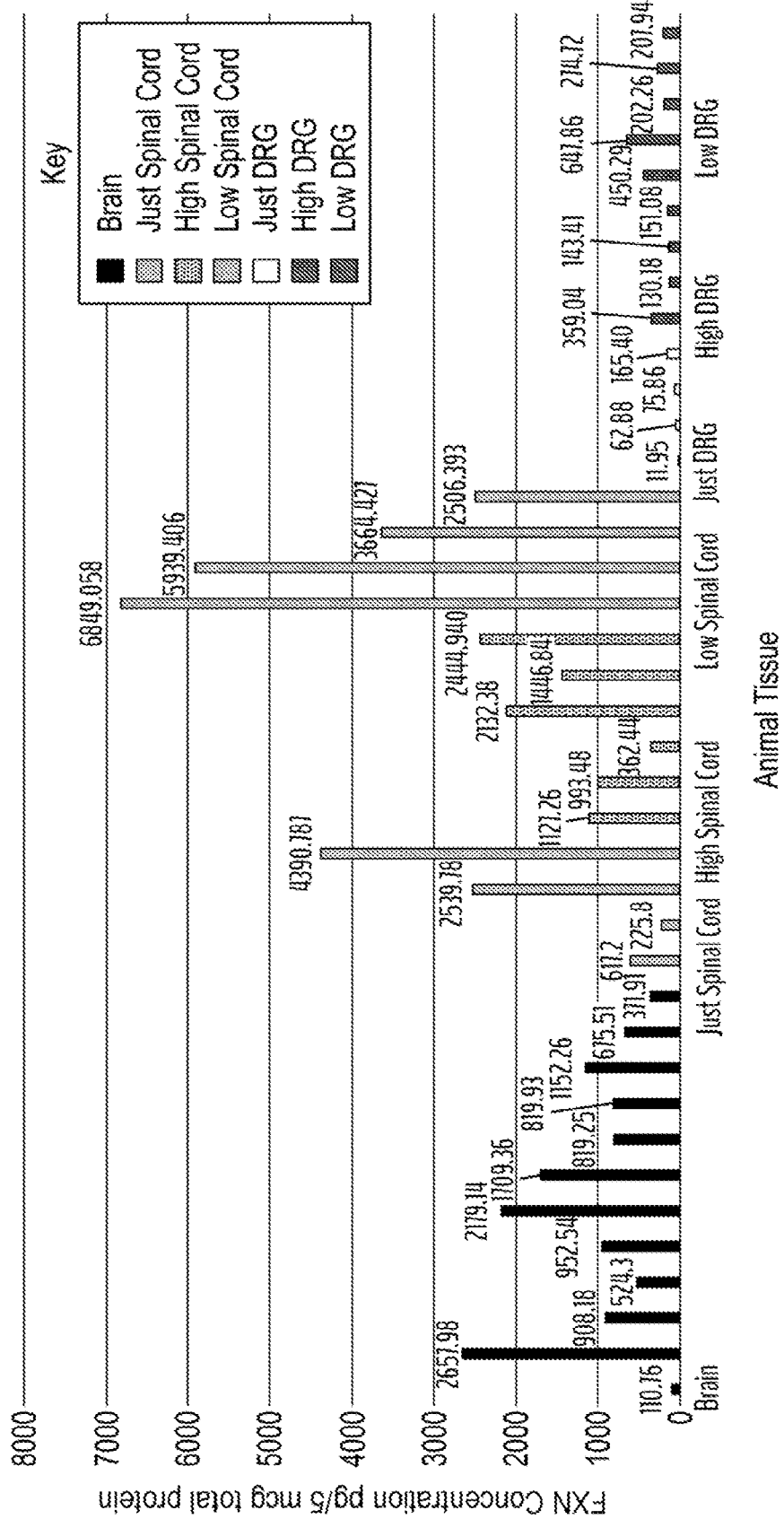
FIG. 7B depicts tissue levels of the TAT-FXN fusion polypeptide (SEQ ID NO: 1) in mouse brain, spine, and dorsal root ganglia (DRG), as described in Example 3.

Tissue penetration of the TAT-FXN fusion polypeptide (SEQ ID NO: 1) into mouse brain, spinal cord, and dorsal root ganglia (DRG) is shown in FIG. 7B. These are target tissues for treatment in FRDA. Here, multiple PVKO mice were injected 3 times per week subcutaneously with the TAT-FXN fusion polypeptide at 10 mg/kg beginning at 1 week of age. Mice were sacrificed at 120 days of age and brain (blue) spinal cord (green, orange, and yellow), and dorsal root ganglia (DRG) (grey, pink, and purple) were harvested. The tissues were homogenized and then 5 mcg of each tissue from each animal was assayed by ELISA (Abcam ab176112, Abcam, Cambridge MA) for the presence of human FXN. This particular ELISA kit is specific for human FXN. For a control, multiple PVKO mice that were dosed with an equivalent volume of vehicle (no TAT-FXN) were also assayed for the presence of human FXN (data in FIG. 7C). As expected, the PVKO mice that received vehicle only had no signal for human FXN in their brain, spinal cord, or DRG. In contrast, all of the PVKO mice had significant human FXN protein mass (pg/5 mcg total protein) in brain, spinal cord, and DRG. The levels vary depending on the interval between the last dose and sacrifice. Spinal cord clearly had the greatest amount of the TAT-FXN fusion polypeptide, with brain slightly less. DRG had the least amount of the TAT-FXN fusion polypeptide, consistent with its small size and minimal mitochondria. These data demonstrate that the TAT-FXN fusion polypeptide crosses the blood-brain barrier to penetrate and accumulate in brain, spinal cord, and DRG in amounts adequate to improve neurologic function. These data also demonstrate that the TAT-FXN fusion polypeptide accumulates in tissues according to the number of mitochondria within the cell. The targeting mechanism of the TAT-FXN fusion polypeptide is engineered to be proteolytically processed by the mitochondrial matrix processing peptidase (specific to the mitochondria) thus trapping the FXN in the matrix of the mitochondria and releasing the TAT-cell penetrant peptide from the mitochondria. Thus, brain and spinal cord, which have significantly greater amounts of mitochondria than DRG, will accumulate more of the TAT-FXN fusion polypeptide than DRG. In a similar manner, heart, which has a very high number of mitochondria per cardiomyocyte, accumulates significantly greater amounts of the TAT-FXN fusion polypeptide (FIG. 7A) than brain and spinal cord (FIG. 7B).

Example 4

The objective of this study was to determine whether, and to what extent, the TAT-FXN fusion polypeptide (SEQ ID NO: 1) would target the rat brain and heart in vivo.

Figure 8A:
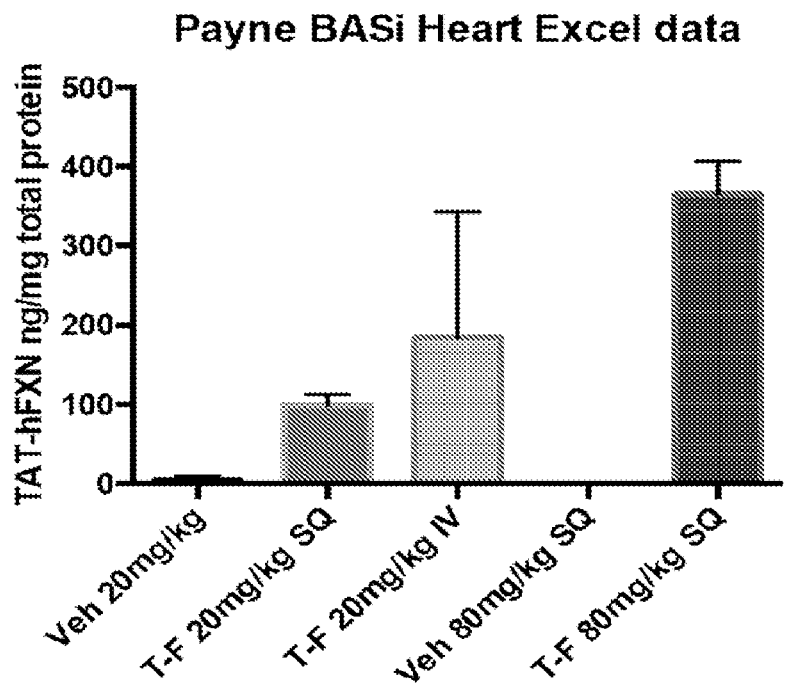
FIG. 8A depicts heart levels of the TAT-FXN fusion polypeptide (SEQ ID NO: 1) after subcutaneous injection or intravenous injection into the rat, as described in Example 4.

FIG. 8A shows heart levels of the TAT-FXN fusion polypeptide after subcutaneous injection or intravenous injection. Five groups of three rats each were injected once per day for 3 days. Tissues were harvested 4 hours after the last injection and snap frozen for later analysis of human FXN by ELISA (Abcam ab176112, Abcam, Cambridge MA). The first experimental group of rats were injected with either 20 mg/kg of vehicle only (no TAT-FXN), 20 mg/kg of the TAT-FXN fusion polypeptide subcutaneously (SQ), or 20 mg/kg of the TAT-FXN fusion polypeptide intravenously (IV). The second experimental group of rats were injected with either vehicle (at a volume equivalent to the amount of TAT-FXN administered to the test group) only (no TAT-FXN), or 80 mg/kg of the TAT-FXN fusion polypeptide subcutaneously (SQ). As expected, the rats injected with vehicle only, no TAT-FXN, showed no tissue levels of the TAT-FXN fusion polypeptide post-injection. In contrast, rats injected either subcutaneously or intravenously with the TAT-FXN fusion polypeptide demonstrated significant tissue levels of human FXN. These data show that single subcutaneous or intravenous daily dosing of the TAT-FXN fusion polypeptide in rat generates significant tissue levels of drug.

Figure 8B:
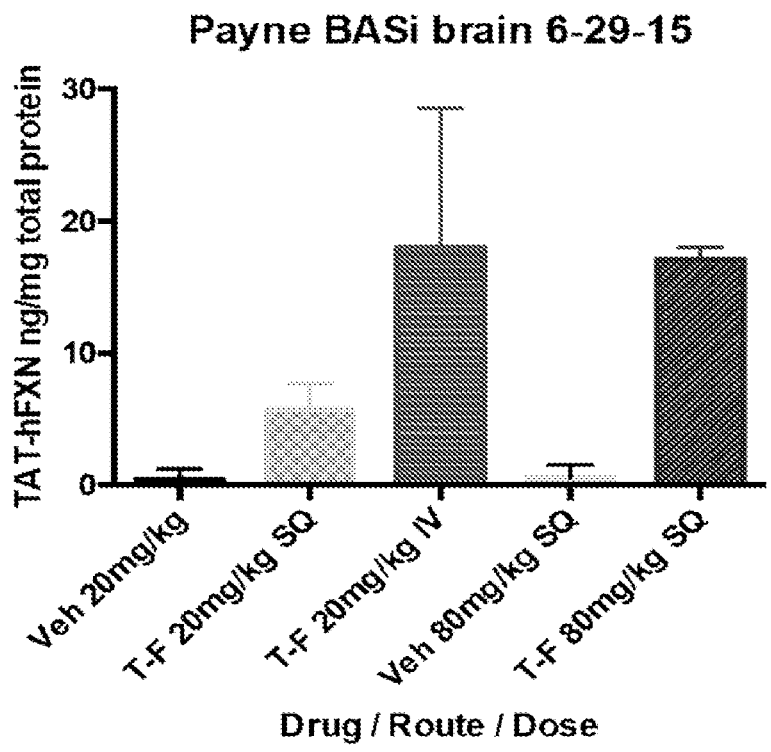
FIG. 8B depicts brain levels of the TAT-FXN fusion polypeptide (SEQ ID NO: 1) after subcutaneous injection or intravenous injection into the rat, as described in Example 4.

FIG. 8B shows brain levels of the TAT-FXN fusion polypeptide after subcutaneous injection or intravenous injection. Four groups of three rats each were injected once per day for 3 days; the 20 mg/kg SQ injected group only contained 2 rats. Tissues were harvested 4 hours after the last injection and snap frozen. The first experimental group of rats were injected with either 20 mg/kg of vehicle only (no TAT-FXN), 20 mg/kg of the TAT-FXN fusion polypeptide subcutaneously (SQ), or 20 mg/kg of the disclosed TAT-FXN fusion polypeptide intravenously (IV). The second experimental group of rats were injected with either 80 mg/kg of vehicle only (no TAT-FXN) or 80 mg/kg of the TAT-FXN fusion polypeptide subcutaneously (SQ). As expected, the rats injected with vehicle only, no TAT-FXN, showed little-to-no tissue levels of the TAT-FXN fusion polypeptide post-injection. In contrast, those rats injected either subcutaneously or intravenously with the TAT-FXN fusion polypeptide demonstrated significant tissue levels.

These data also show that single subcutaneous or intravenous daily dosing of the TAT-FXN fusion polypeptide in rat generates significant tissue levels of drug.

Figure 9A:
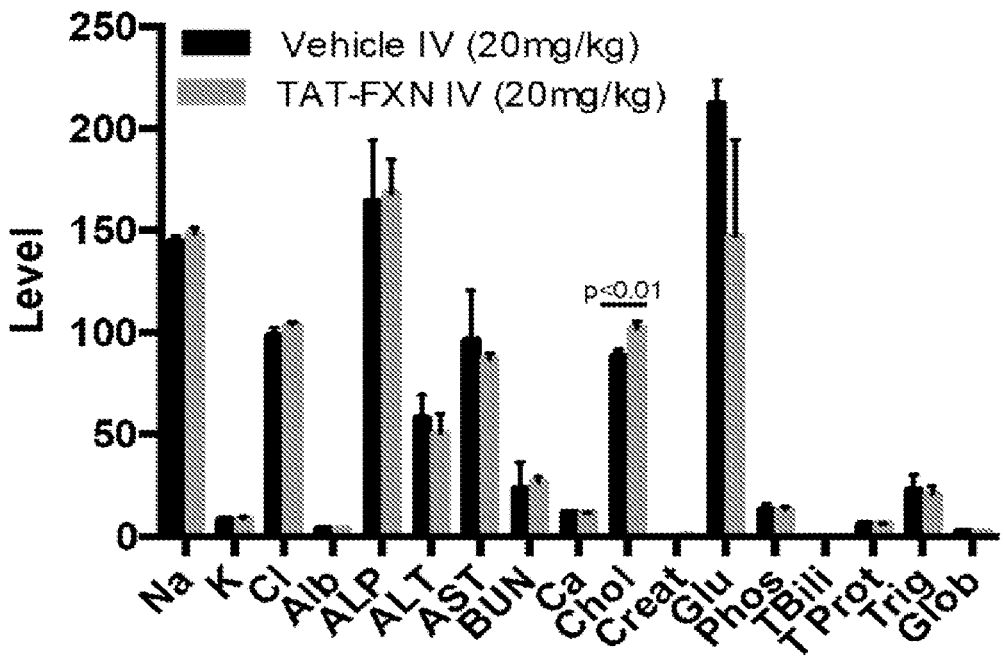
FIG. 9A depicts blood chemistry after intravenous injection of the TAT-FXN fusion polypeptide (SEQ ID NO: 1), as described in Example 4.
Figure 9B:
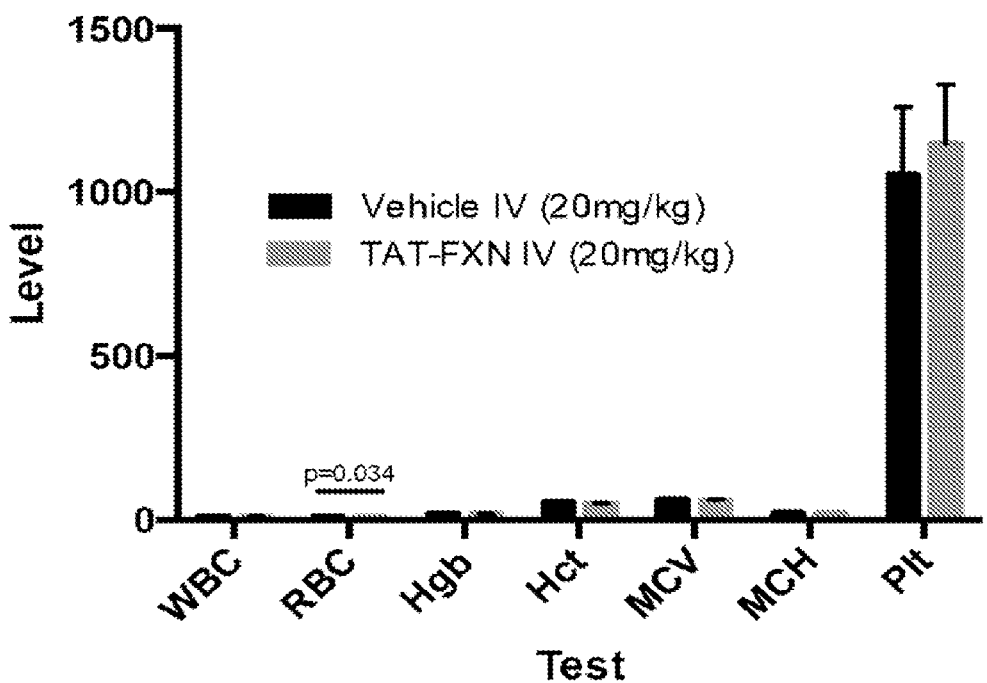
FIG. 9B illustrates rat haematology data after intravenous injection of the TAT-FXN fusion polypeptide (SEQ ID NO: 1), as described in Example 4.

Additionally, intravenous injection of the TAT-FXN fusion polypeptide is well tolerated with little impact on rat blood chemistry (FIG. 9A) or haematology (FIG. 9B). Rats were injected intravenously with either vehicle only (no TAT-FXN) or 20 mg/kg of the TAT-FXN fusion polypeptide (SEQ ID NO: 1). Each group of rats (n=3/group) was injected once per day for 3 days. Blood was collected 4 hours after the last injection.

The data show that there was a significant, but small, difference in cholesterol levels (FIG. 9A) and a significant, but small, difference in red blood cell levels (FIG. 9B). All other values were not significant. These data clearly show that the TAT-FXN fusion polypeptide is well tolerated in rats.

Example 5

This example provides the results of a toxicokinetic study after chronic injection of the TAT-FXN fusion polypeptide into rats. The TAT-FXN fusion polypeptide was subcutaneously injected into 4 groups of rats (n=4/group) twice per week, for a total of 28 days. The animals from each group were then sacrificed and necropsied. The amount of the TAT-FXN fusion polypeptide administered to each group, and the tissues analysed per group, are shown in Table 2:

TABLE 2

| Group | Test Article | Route | Frequency | Study Day | Tissues |
| --- | --- | --- | --- | --- | --- |
| 1 | Vehicle (80 mg/kg vol) | SC | 2 × per week | 28 | Brain, heart, liver, lung |
| 2 | TAT-FXN (5 mg/kg) | SC | 2 × per week | 28 | Brain, heart, liver, lung |
| 3 | TAT-FXN (20 mg/kg) | SC | 2 × per week | 28 | Brain, heart, liver, lung |
| 4 | TAT-FXN (80 mg/kg) | SC | 2 × per week | 28 | Brain, heart, liver, lung |

Figure 10:
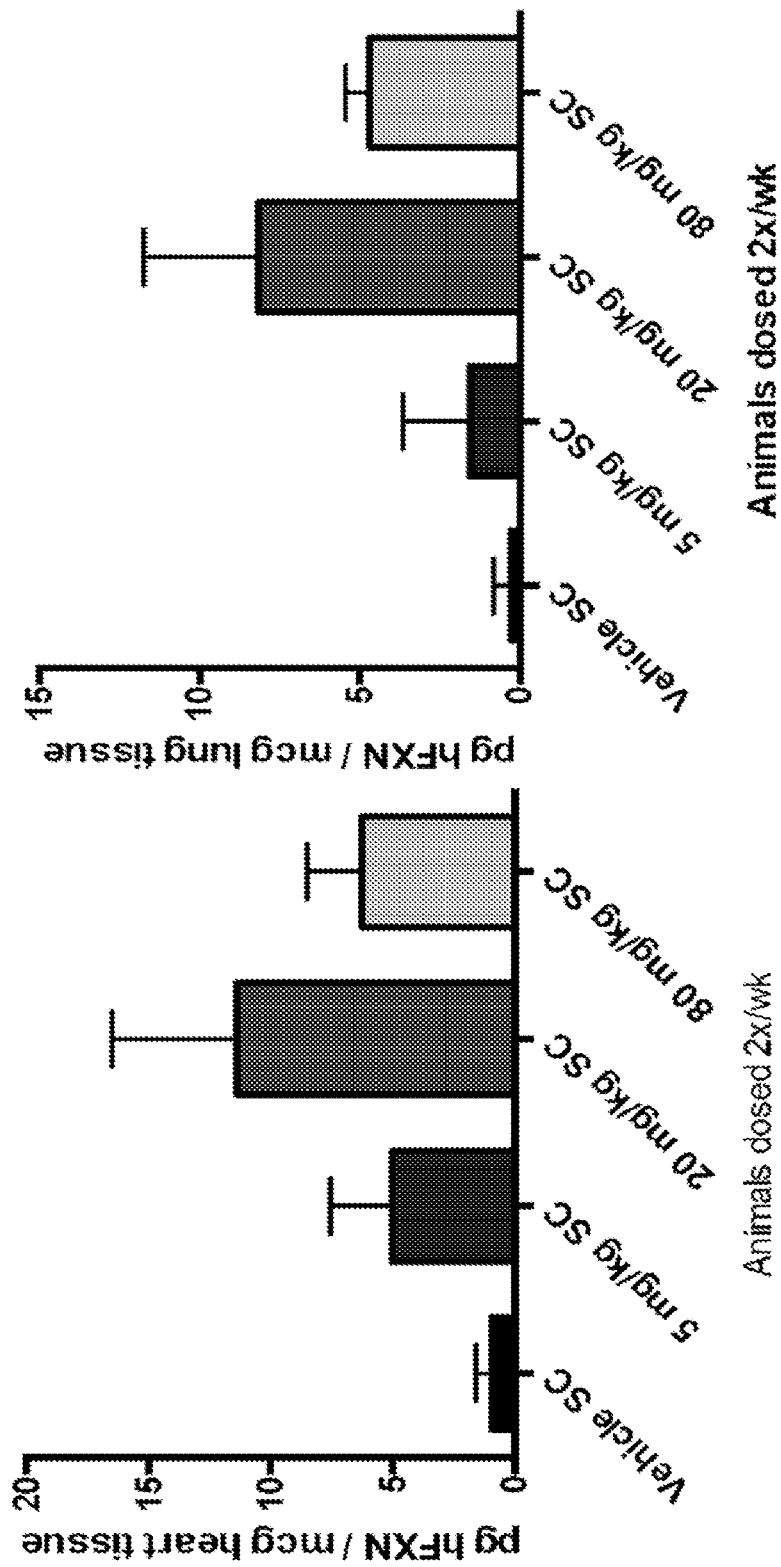
FIG. 10 depicts tissue levels of the TAT-FXN fusion polypeptide (SEQ ID NO: 1) after chronic injection in rats, as described in Example 5.

Tissue levels of the TAT-FXN fusion polypeptide are shown in FIG. 10.

No organ findings were noted. Focal swelling/irritation was seen at the injection sites at higher drug doses, though this related to the high vehicle volume, not the TAT-FXN fusion polypeptide. Weight gain in all the animals was appropriate.

The data presented in FIG. 10 show dose response for heart and lung tissues over time with injections twice per week. The drop in tissue levels seen at 80 mg/kg reflect leak of drug from injection site, or precipitation of drug at injection site.

These data show that the TAT-FXN fusion polypeptide was not toxic to rats when administered twice per week over a 28-day period.

Example 6

The goal of the experiments described in Example 6 was to compare the activity and solubility of the TAT-FXN fusion polypeptide (SEQ ID NO: 1) and the Vyas et al. polypeptide. The activity assay involves monitoring production of reactive oxygen species (ROS) by the peptides by monitoring oxidation of hydroquinone (HQ). To this end, an assay mixture was prepared containing 5 μM Fe(III) sulfate, 5 μM hydroquinone (HQ) as the reducing agent and 0.25 μM 2',7'-dichlorofluorescein (H₂DCF) as the ROS detector compound. Each assay mixture was added to a well on a 96-well plate, and Tris-HCl buffer at pH 8.0 was added to normalize the volume. Various amounts of Vyas et al. polypeptide or the disclosed TAT-FXN fusion polypeptide were added to each assay mixture to final concentrations of 0-10 μM in order to initiate the reaction. The 96-well plate was incubated for 1 hour. To determine activity of the Vyas et al. polypeptide or the disclosed TAT-FXN fusion polypeptide, fluorescence of each assay mixture was measured using excitation at 485/20 and emission at 528/20. To determine peptide aggregation/precipitation in each assay mixture, optical density at 630 nm was measured.

Figure 11A:
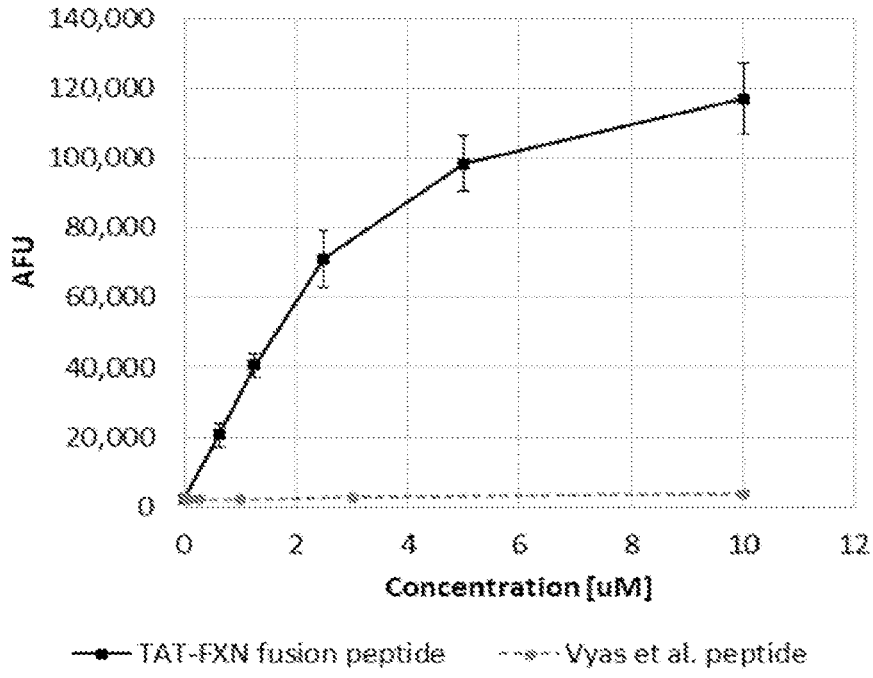
FIG. 11A is a graph showing the amount of activity of Vyas et al. polypeptide and the disclosed TAT-FXN fusion polypeptide (SEQ ID NO: 1) as a function of peptide concentration, as measured by fluorescence and as described in Example 6.

The results are presented in FIG. 11. Specifically, FIG. 11A is a graph showing the amount of activity of Vyas et al. polypeptide or the disclosed TAT-FXN fusion polypeptide as a function of peptide concentration, as measured by fluorescence. The results shown in FIG. 11A indicate that the activity of the disclosed TAT-FXN fusion polypeptide increases as a function of increasing peptide concentration. In contrast, the Vyas et al. polypeptide displays no activity at all peptide concentrations tested.

Figure 11B:
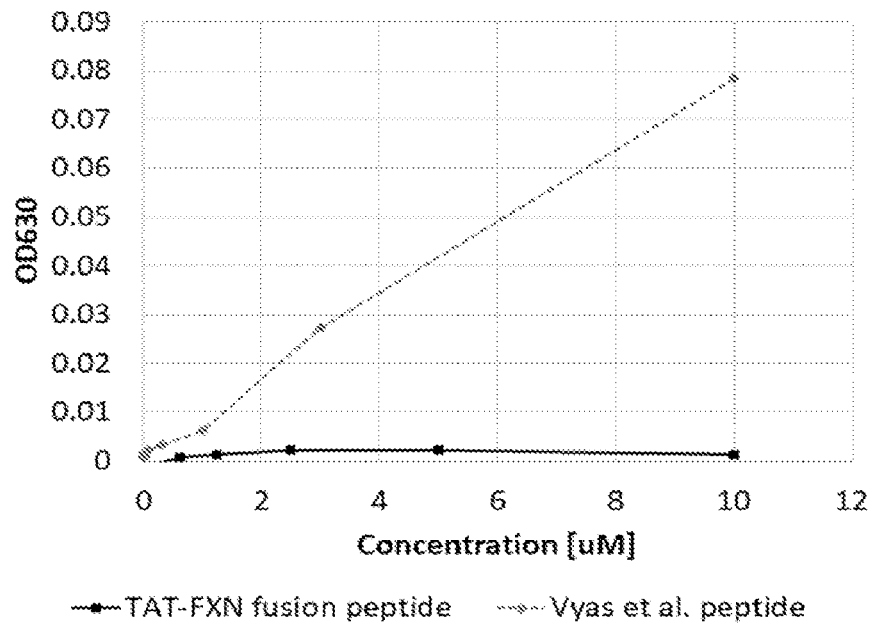
FIG. 11B is a graph showing the amount of aggregation/precipitation of the Vyas et al. polypeptide or the disclosed TAT-FXN fusion polypeptide (SEQ ID NO: 1) as a function of peptide concentration, as measured by $OD_{630}$, as described in Example 6.

FIG. 11B is a graph showing the amount of aggregation/precipitation of the Vyas et al. polypeptide or the disclosed TAT-FXN fusion polypeptide as a function of peptide concentration, as measured by $OD_{630}$. The results shown in FIG. 11B indicate that $OD_{630}$ of the Vyas et al. polypeptide increases with increasing polypeptide concentration, demonstrating increasing aggregation/precipitation of the Vyas et al. polypeptide. In contrast, no increase in the $OD_{630}$ as a function of peptide concentration is observed for the disclosed TAT-FXN fusion polypeptide, indicating no aggregation/precipitation.

The results shown in FIG. 11 demonstrate that the Vyas et al. polypeptide is not soluble at the tested assay conditions and aggregates/precipitates out of solution at the peptide concentrations tested. In contrast, the disclosed TAT-FXN fusion polypeptide is soluble and active at the assay conditions tested.

Example 7

The goal of the experiments described in Example 7 was to determine the stability of the TAT-FXN fusion polypeptide (SEQ ID NO: 1) and the Vyas et al. polypeptide in human plasma. To this end, the recombinant TAT-FXN fusion polypeptide and the Vyas et al. polypeptide were expressed in E. coli cells in the presence of 1 mM Isopropyl β-D-1-thiogalactopyranoside (IPTG) in order to induce recombinant protein expression under control of the Lac operator. The bacterial cells were then collected by centrifugation, and both polypeptides were purified in parallel using methods appropriate to each polypeptide to obtain high purity polypeptide preparation. After purification, each polypeptide was formulated in 15% human plasma (hP, Biorec-lamationIVT) diluted in PBS. Subsequently, 500 ng of each polypeptide was incubated in 50 mL of 15% hP in PBS for 0.5, 1, 2 and 4 hours at 37° C. in the absence or presence of a protease inhibitor cocktail (Sigma P/N P8340). As a control, 500 ng of each polypeptide was incubated in 50 mL of 100% PBS. Aliquots from each reaction were analyzed by Western Blotting using a mouse monoclonal antibody specific for human FXN (Abcam ab110328) and an infrared-dye-labelled goat anti mouse IgG (Li-Cor Biotech P/N 925-32210) as the secondary antibody. The immunoblots were scanned and analyzed using an Odyssey CLx infrared scanner (Li-Cor Biotech).

Figure 12A:
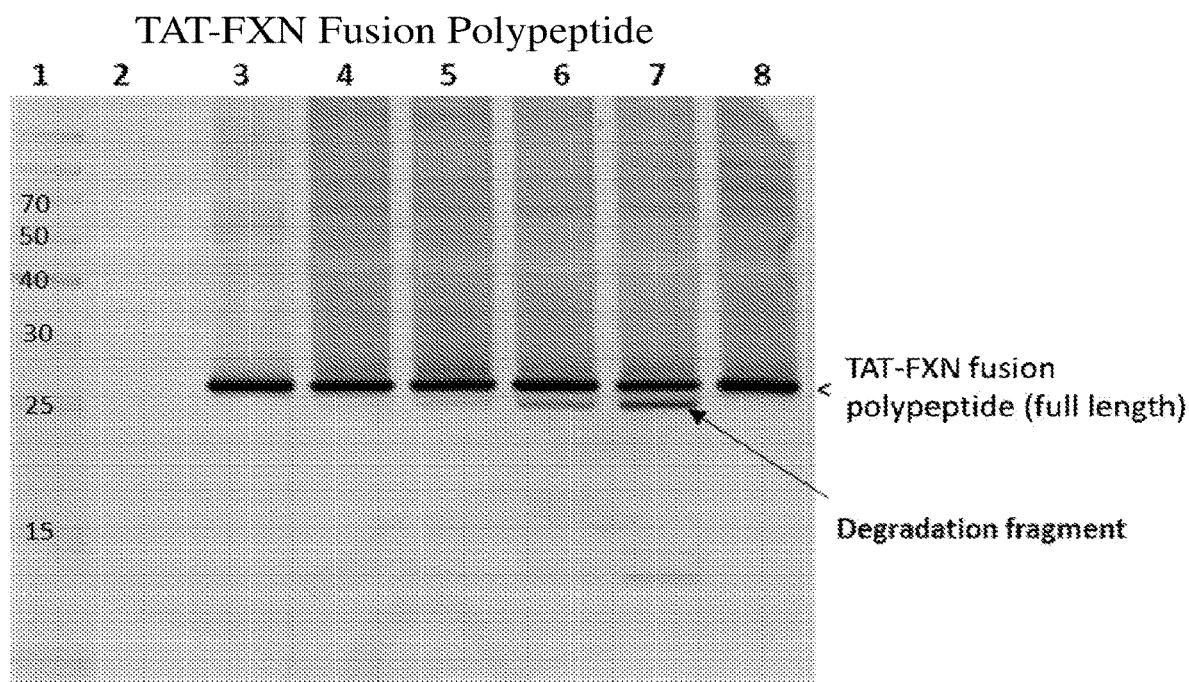
FIG. 12A is an image of the Western Blot of the TAT-FXN fusion polypeptide (SEQ ID NO: 1) incubated for different times in 15% human plasma.

FIG. 12A is an image of the Western Blot of the TAT-FXN fusion polypeptide incubated for different times in 15% human plasma. FIG. 13A shows a band corresponding to the full-length TAT-FXN fusion polypeptide and a degradation product of a lower MW that accumulates over time. FIG. 12B is an image of the Western Blot of the Vyas et al. polypeptide incubated for different times in 15% human plasma. FIG. 12B shows a band corresponding to the full-length Vyas et al. polypeptide and a degradation product of a lower MW that accumulates over time Percent degradation of each polypeptide as a function of time was determined using image analysis of the Western Blots. Specifically, the percent degradation for each polypeptide was calculated by dividing the intensity of the signal corresponding to the lower MW degradation product by the intensity of the signal of the higher MW band corresponding to the full-length polypeptide when incubated in PBS only.

Figure 12C:
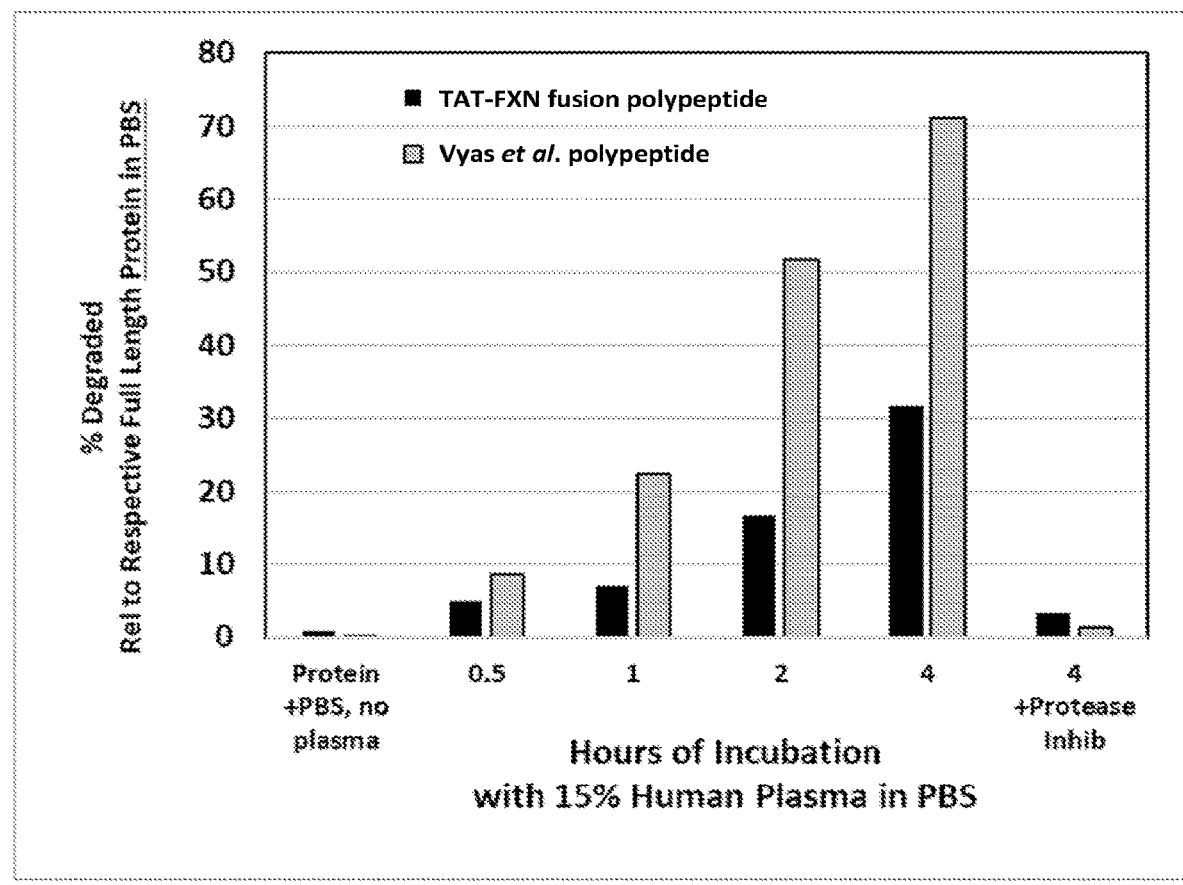
FIG. 12C is a bar graph indicating % degradation of the TAT-FXN fusion polypeptide and the Vyas et al. polypeptide after incubation in 15% human plasma diluted in PBS for different amounts of time.

FIG. 12C is a bar graph showing % degradation of the TAT-FXN fusion polypeptide and the Vyas et al. polypeptide after incubation in 15% human plasma diluted in PBS for different amounts of time. The results presented in FIG. 12C indicate that the Vyas et al. polypeptide degrades in human plasma significantly more rapidly than the TAT-FXN fusion polypeptide, at all of the time points tested. Thus, the TAT-FXN fusion polypeptide is significantly more stable in human plasma than the Vyas et al. polypeptide.

Example 8

The goal of the experiments described in Example 8 was to compare the ability of the TAT-FXN fusion polypeptide (SEQ ID NO: 1) and the Vyas et al. polypeptide to enter cells. To this end, Schwann cells, which are myelinating cells of the peripheral nervous system, were transduced with the TAT-FXN fusion polypeptide and the Vyas et al. polypeptide, the amount of each polypeptide entering the cells was quantified, and the quantified amounts for the TAT-FXN fusion polypeptide and the Vyas et al. polypeptide were compared to each other.

Schwann cells were plated in a tissue culture 96-well plate at a seeding density of about 8000 cells per well, and incubated overnight at 37° C. The following day, the cells in each well were washed with 150 μL of PBS and incubated at 37° C. for 3 hours with 70 μL of 0 μM (control) or 12.5 μM of TAT-FXN fusion polypeptide or of the Vyas et al. polypeptide in transduction media (DMEM, 1% heat inactivated FBS and 20 mM glycerol). Subsequently, an equal volume of complete media [DMEM, 10% FBS, 1% antibiotic:antimycotic (Gemini Bio, 400-101)] was added, and the cells were incubated overnight at 37° C. The same treatment was repeated the next day, after which the cells in each well were washed with 150 μL PBS and trypsinized using 50 μL TrypLE Express (Gibco®, 12604021) per well at 37° C. for 5 minutes.

The cells were resuspended in 50 μL of complete medium and transferred onto a fibronectin coated glass bottom plate (Corning®, 4584) containing 40 μL of pre-warmed complete media. The cells were allowed to settle overnight at 37° C. The following morning, the cells were washed with PBS, after which 50 μL of freshly prepared 4% paraformaldehyde solution was added to each well, and the cells were incubated at room temperature for 10 minutes. Subsequently, the cells in each well were washed twice with 150 μL of PBS, 50 μL of blocking buffer (0.3% Triton-X 100, 5% normal goat serum in PBS) was added, and the cells were incubated at room temperature for 1 hour. Subsequently, the blocking buffer was aspirated, 50 μl of primary antibody diluted in blocking buffer [anti-frataxin antibody, Abcam® ab110328 (1:300)] was added to each well, and the cells were incubated overnight at 4° C.

The cells in each well were then washed twice with 120 μL of PBS, 50 μL of the secondary antibody [anti-mouse IgG AlexaFluor594, Abcam® ab150116 (1:1000)] diluted in blocking buffer was added, and the cells were incubated at room temperature for one hour. The cells in each well were then washed three times with 150 μL of PBS, after which 50 μL of 300 nM Hoechst 33342 stain was added, and the cells were incubated for 3 minutes at room temperature. Subsequently, the cells in each well were washed twice with PBS and imaged using Lionheart FX imager. The amount of frataxin per cell was quantified using the average of 16 fields obtained from imaging 5 different wells of the 96-well plate at 20× magnification. Data is reported as the ratio of the total area of the AlexaFluor594Red signal (corresponding to the total amount of frataxin) to the total area of the Hoechst 33342 signal (corresponding to the amount of nuclear DNA). Examples of the capture images at 20× magnification following each treatment are shown in FIG. 13A, panels A-D. Examples of capture images at higher resolution (60×oil immersion) following each treatment are shown in FIG. 13A, panels E-F.

Specifically, FIG. 13A, panel A shows Schwann cells in one well of a 96-well plate treated for two days with 0 μM TAT-FXN fusion polypeptide and stained with the nuclear stain Hoechst 33342 and the anti-frataxin stain Texas Red.

FIG. 13A, panel B shows Schwann cells in one well of a 96-well plate treated for two days with 0 μM Vyas et al. polypeptide and stained with the nuclear stain Hoechst 33342 and the anti-frataxin stain Texas Red.

FIG. 13A, panel C shows Schwann cells in one well of a 96-well plate treated for two days with 12.5 μM TAT-FXN fusion polypeptide and stained with the nuclear stain Hoechst 33342 and the anti-frataxin stain Texas Red.

FIG. 13A, panel D shows Schwann cells in one well of a 96-well plate treated for two days with 12.5 μM Vyas et al. polypeptide and stained with the nuclear stain Hoechst 33342 and the anti-frataxin stain Texas Red.

FIG. 13A, panel E shows Schwann cells in one well of a 96-well plate treated for two days with 12.5 μM TAT-FXN fusion polypeptide, stained with the nuclear stain Hoechst 33342 and the anti-frataxin stain Texas Red and imaged using 60× oil objective.

FIG. 13A, panel F shows Schwann cells in one well of a 96-well plate treated for two days with 12.5 μM Vyas et al. polypeptide, stained with the nuclear stain Hoechst 33342 and the anti-frataxin stain Texas Red and imaged using 60× oil objective.

Figure 13B:
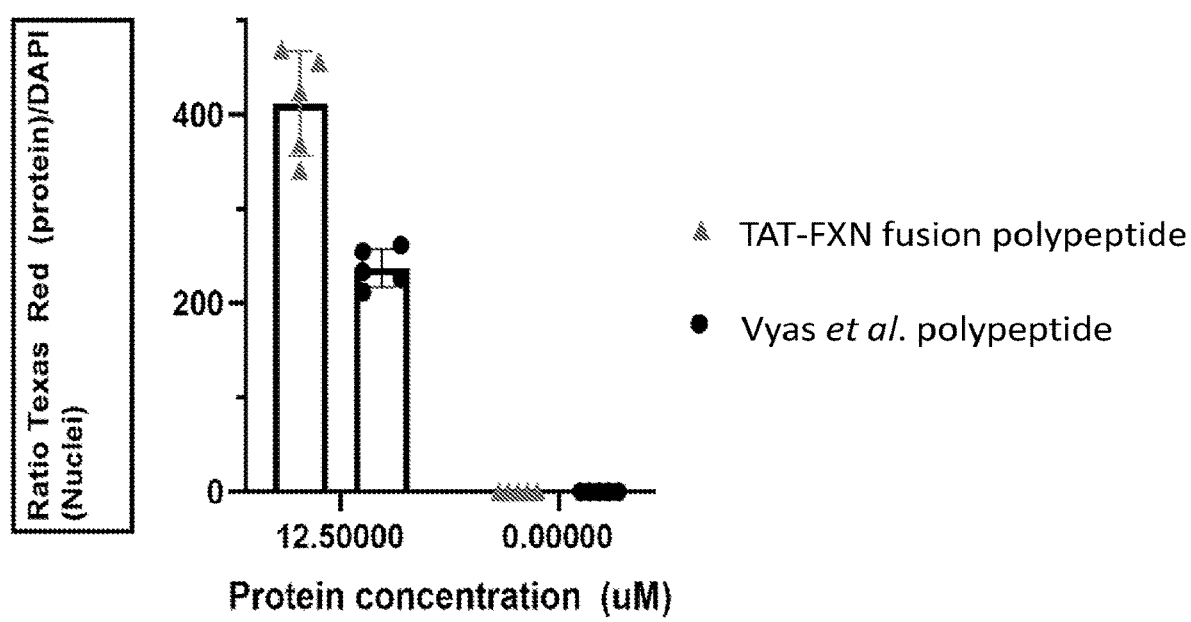
FIG. 13B is a bar graph indicating the ratio of the amount of Texas Red stain corresponding to frataxin to the amount of Hoechst 33342 nuclear stain in Schwann cells treated with 0 µM or 12.5 µM TAT-FXN fusion polypeptide (SEQ ID NO: 1) or the Vyas et al. polypeptide.

FIG. 13B is a bar graph showing the ratio of the amount of Texas Red stain to the amount of Hoechst 33342 nuclear stain in Schwann cells treated with 0 μM or 12.5 μM TAT-FXN fusion polypeptide or the Vyas et al. polypeptide.

Figure 14A:
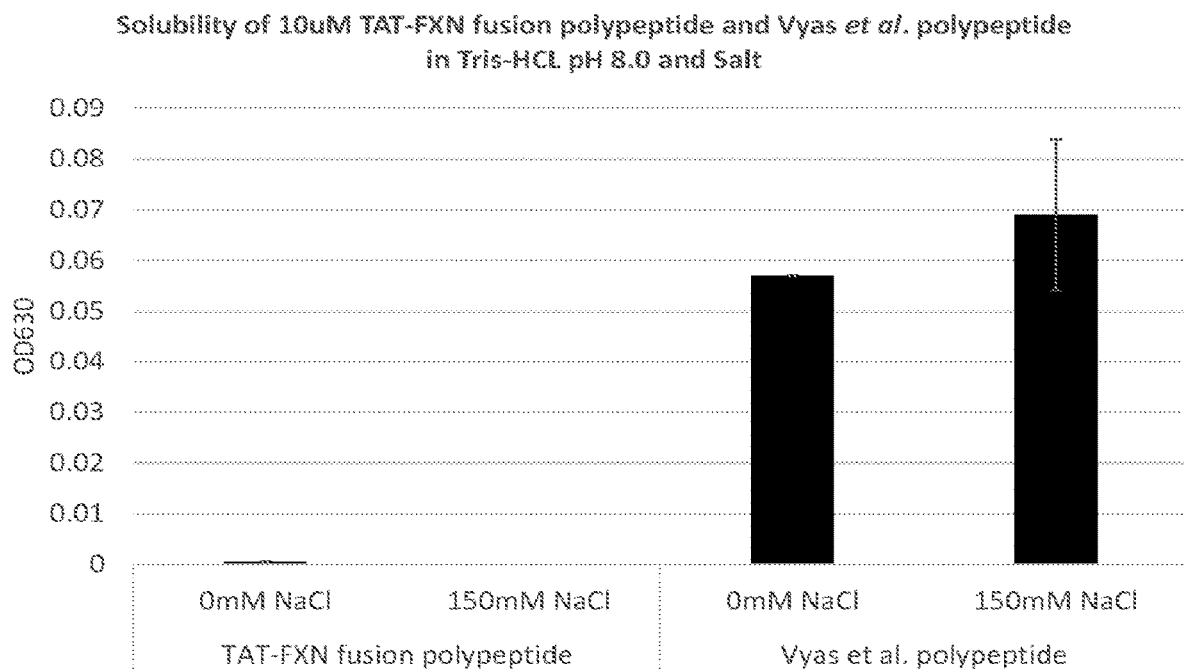
FIG. 14A is a bar graph representing the amount of the aggregation/precipitation of the TAT-FXN fusion polypeptide (SEQ ID NO: 1) and the Vyas et al. polypeptide as measured by $OD_{630}$ at the polypeptide concentration of 10 µM in the presence of 0 mM or 150 mM NaCl.
Figure 14B:
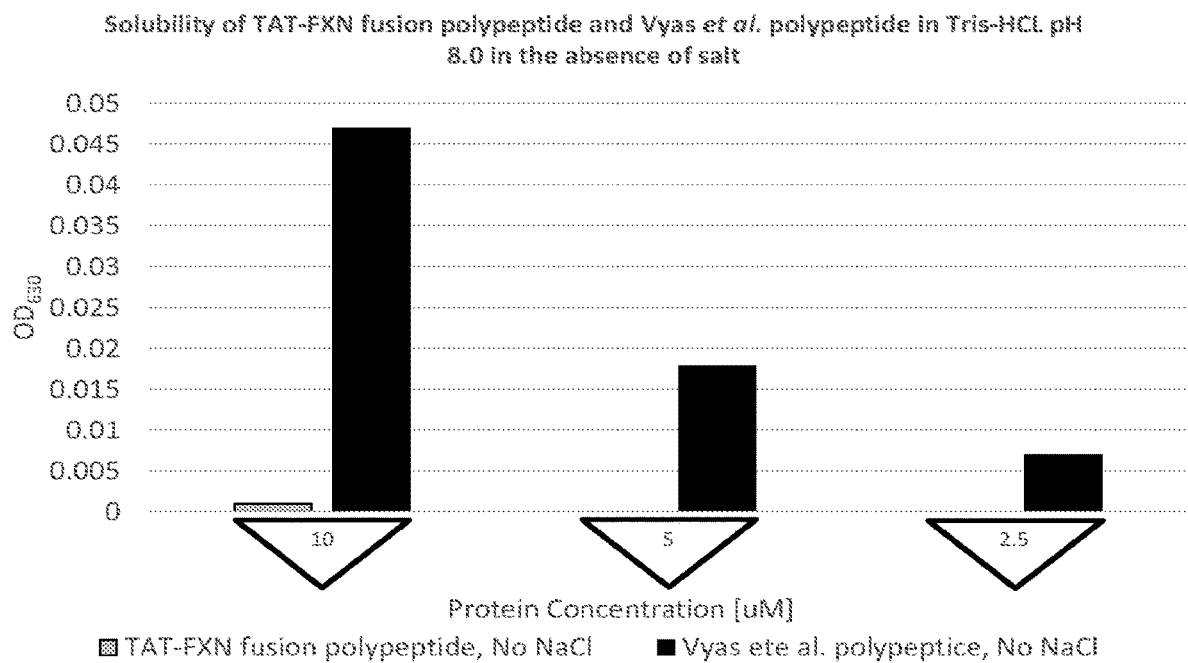
FIG. 14B is a bar graph representing the amount of the aggregation/precipitation of the TAT-FXN fusion polypeptide (SEQ ID NO: 1) and the Vyas et al. polypeptide as measured by $OD_{630}$ at polypeptide concentrations of 2.5 µM, 5 µM and 10 µM in the absence of NaCl.

The results presented in FIGS. 14A and 14B indicate that the amount of the TAT-FXN fusion polypeptide that entered Schwann cells following transduction is significantly higher than the amount of the Vyas et al. polypeptide that entered cells. Based on these results, it is predicted that the TAT-FXN fusion protein will enter cells more efficiently in vivo than the Vyas et al. polypeptide, and will therefore provide greater therapeutic efficacy.

Example 9

The goal of the experiments described in Example 9 was to compare the solubility and activity of the TAT-FXN fusion polypeptide (SEQ ID NO: 1) and the Vyas et al. polypeptide. To compare solubilities of the TAT-FXN fusion polypeptide and the Vyas et al. polypeptide, $OD_{630}$ was used as a measure of aggregation/precipitation of a polypeptide. To this end, the TAT-FXN fusion polypeptide and the Vyas et al. polypeptide were expressed as described in Example 7. Serial dilutions of each polypeptide in 50 mM Tris-HCL pH 8.0 and various concentrations of NaCl were prepared and $OD_{630}$ was measured for each dilution FIG. 14A is a bar graph showing the amount of the aggregation/precipitation of the TAT-FXN fusion polypeptide and the Vyas et al. polypeptide as measured by $OD_{630}$ at the polypeptide concentration of 10 μM in the presence of 0 mM or 150 mM NaCl. The results presented in FIG. 14A indicate that significant amounts of aggregation/precipitation of the Vyas et al. polypeptide are observed both at 0 mM NaCl and 150 mM NaCl, while no significant amounts of aggregation/precipitation are detectable for the TAT-FXN polypeptide.

FIG. 14B is a bar graph showing the amount of the aggregation/precipitation of the TAT-FXN fusion polypeptide and the Vyas et al. polypeptide as measured by $OD_{630}$ at polypeptide concentrations of 2.5 μM, 5 μM and 10 μM in the absence of NaCl. The results presented in FIG. 14B indicate that significant amounts of aggregation/precipitation of the Vyas et al. polypeptide are observed in the absence of salt at all polypeptide concentrations studied. The results presented in FIG. 14B further indicate that no detectable aggregation/precipitation is observed for the TAT-FXN fusion polypeptide at polypeptide concentrations of 2.5 μM and 5 μM, and a barely detectable amount of aggregation/precipitation is observed at a polypeptide concentration of 10 μM, in the absence of salt.

Figure 14C:
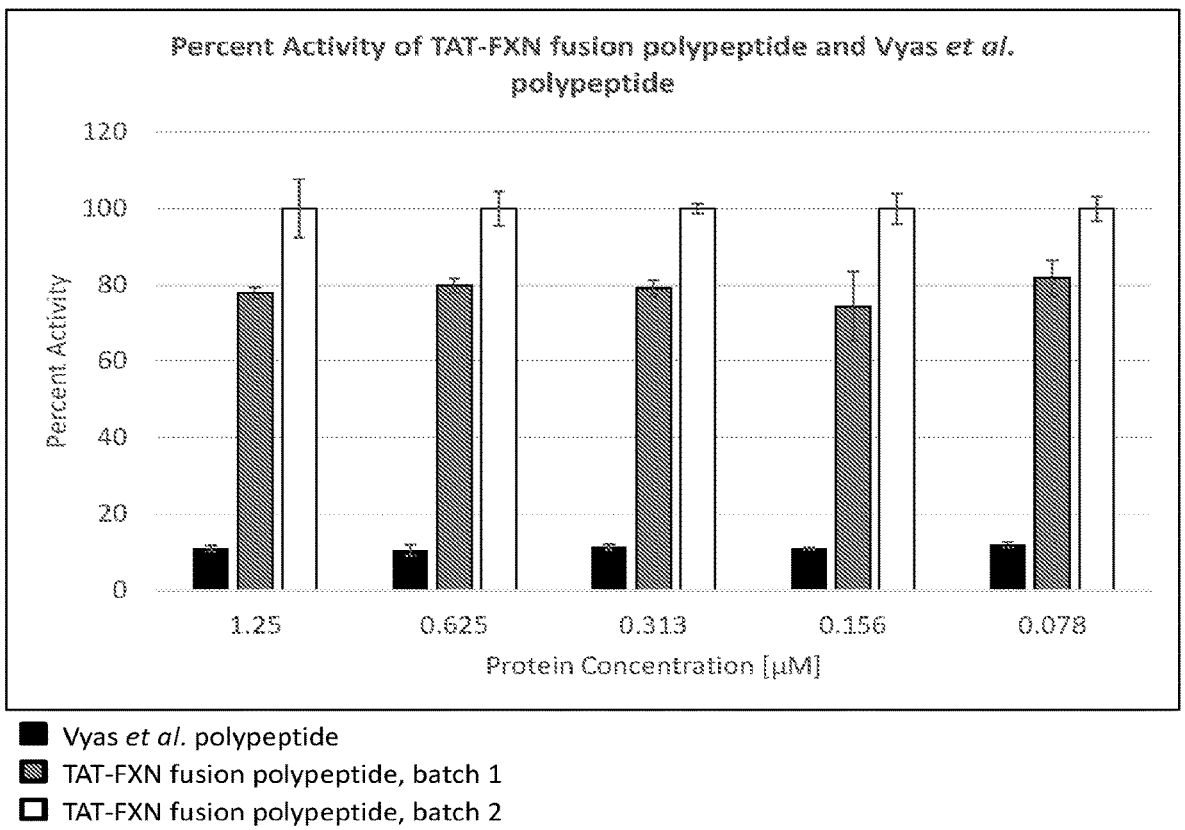
FIG. 14C is a bar graph indicating the percent activity of two different batches (batch 1 and batch 2) of the TAT-FXN fusion polypeptide (SEQ ID NO: 1) and of the Vyas et al. polypeptide, normalized to the specific activity of the batch 2 of the TAT-FXN fusion polypeptide, at polypeptide concentrations of 0.078 µM, 0.156 µM, 0.313 µM, 0.625 µM and 1.25 µM.

The activity of two different batches of the TAT-FXN fusion polypeptide (batch 1 and batch 2) and the Vyas et al. polypeptide was determined using the activity assay described in Example 6. FIG. 14C is a bar graph showing the percent activity of the batch 1 and batch 2 of the TAT-FXN fusion polypeptide and the Vyas et al. polypeptide, normalized to the specific activity of the batch 2 of the TAT-FXN fusion polypeptide, at polypeptide concentrations of 0.078 μM, 0.156 μM, 0.313 μM, 0.625 μM and 1.25 μM. The results presented in FIG. 14C indicate that, for all polypeptide concentrations studied, batch 1 of the TAT-FXN fusion polypeptide demonstrates activity that is about 80% of the activity of batch 2 of the TAT-FXN fusion polypeptide, while the Vyas et al. polypeptide demonstrates activity that is below 15% of batch 2 of the TAT-FXN fusion polypeptide.

The results shown in FIGS. 14A, 14B and 14C, taken together, demonstrate that the Vyas et al. polypeptide displays poor solubility and activity at the tested assay conditions. In contrast, the TAT-FXN fusion polypeptide is soluble and active at the assay conditions tested.

The novel technology has been illustrated and described in detail in the figures and foregoing description, the same is to be considered as illustrative and not restrictive in character, it being understood that only examples of compositions, methods of using and methods of making the compositions have been shown and described and that all changes and modifications that come within the spirit of the novel technology are desired to be protected.

As well, while the novel technology was illustrated using specific examples, theoretical arguments, accounts, and illustrations, these illustrations and the accompanying discussion should by no means be interpreted as limiting the technology.

SEQUENCE LISTING

```
Sequence total quantity: 11
SEQ ID NO: 1                 moltype = AA   length = 224
FEATURE                      Location/Qualifiers
REGION                       1..224
                             note = Description of Artificial Sequence: Synthetic
                              polypeptide
source                       1..224
                             mol_type = protein
                             organism = synthetic construct
SEQUENCE: 1
MYGRKKRRQR RRGGMWTLGR RAVAGLLASP SPAQAQTLTR VPRPAELAPL CGRRGLRTDI    60
DATCTPRRAS SNQRGLNQIW NVKKQSVYLM NLRKSGTLGH PGSLDETTYE RLAEETLDSL   120
AEFFEDLADK PYTFEDYDVS FGSGVLTVKL GGDLGTYVIN KQTPNKQIWL SSPSSGPKRY   180
DWTGKNWVYS HDGVSLHELL AAELTKALKT KLDLSSLAYS GKDA                   224

SEQ ID NO: 2                 moltype = AA   length = 12
FEATURE                      Location/Qualifiers
REGION                       1..12
                             note = Description of Artificial Sequence: Synthetic peptide
source                       1..12
                             mol_type = protein
                             organism = synthetic construct
SEQUENCE: 2
MYGRKKRRQR RR                                                       12

SEQ ID NO: 3                 moltype = AA   length = 80
FEATURE                      Location/Qualifiers
source                       1..80
                             mol_type = protein
                             organism = Homo sapiens
SEQUENCE: 3
MWTLGRRAVA GLLASPSPAQ AQTLTRVPRP AELAPLCGRR GLRTDIDATC TPRRASSNQR    60
GLNQIWNVKK QSVYLMNLRK                                               80

SEQ ID NO: 4                 moltype = AA   length = 210
FEATURE                      Location/Qualifiers
source                       1..210
                             mol_type = protein
                             organism = Homo sapiens
SEQUENCE: 4
MWTLGRRAVA GLLASPSPAQ AQTLTRVPRP AELAPLCGRR GLRTDIDATC TPRRASSNQR    60
GLNQIWNVKK QSVYLMNLRK SGTLGHPGSL DETTYERLAE ETLDSLAEFF EDLADKPYTF   120
EDYDVSFGSG VLTVKLGGDL GTYVINKQTP NKQIWLSSPS SGPKRYDWTG KNWVYSHDGV   180
SLHELLAAEL TKALKTKLDL SSLAYSGKDA                                   210

SEQ ID NO: 5                 moltype = AA   length = 130
FEATURE                      Location/Qualifiers
source                       1..130
                             mol_type = protein
                             organism = Homo sapiens
SEQUENCE: 5
SGTLGHPGSL DETTYERLAE ETLDSLAEFF EDLADKPYTF EDYDVSFGSG VLTVKLGGDL    60
GTYVINKQTP NKQIWLSSPS SGPKRYDWTG KNWVYSHDGV SLHELLAAEL TKALKTKLDL   120
SSLAYSGKDA                                                         130

SEQ ID NO: 6                 moltype = DNA   length = 684
FEATURE                      Location/Qualifiers
misc_feature                 1..684
                             note = Description of Artificial Sequence: Synthetic
                              polynucleotide
source                       1..684
                             mol_type = other DNA
                             organism = synthetic construct
SEQUENCE: 6
catatgtatg gtagaaagaa acgtcgtcaa cgtcgtcgtg gtggtatgtg gaccttgggc    60
cgtcgcgcgg ttgcgggcct gctggcgagc ccaagcccgg cacaggcgca gaccctgacg   120
cgcgttccgc gtccggcgga attggccccg ttgtgcggtc gccgtggtct cgcacggat   180
atcgacgcta cctgtacgcc gcgtcgcgcg agcagcaatc agcgtggcct gaatcaaatt   240
tggaacgtca agaaacaatc tgtttacctg atgaatctgc gcaagagcgg tacgttgggt   300
cacccgggca gcctggacga gactacctat gagcgcctgg ctgaggaaac gctggacagc   360
ctggccgaat ttttcgaaga tctcgcagat aagccgtaca cgtttgagga ttatgacgtg   420
agcttcggca gcggcgtctt aaccgtgaaa ctggtggtg acctgggcac ctacgtgatc   480
aataagcaaa ccccgaacaa acagatttgg ctgagctcgc cgagctctgg ccctaagcgt   540
tacgattgga ccggtaagaa ctgggtgtat tcccacgacg gtgtcagcct gcatgaactg   600
ctgcggcag agctgaccaa agcgctgaaa actaaactgg atctgagctc cctggcctac   660
agcggtaaag acgcataact cgag                                         684

SEQ ID NO: 7                 moltype = AA   length = 11
```

```
FEATURE                 Location/Qualifiers
source                  1..11
                        mol_type = protein
                        organism = Human immunodeficiency virus
SEQUENCE: 7
YGRKKRRQRR R                                                              11

SEQ ID NO: 8            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 8
GGGGGGGG                                                                  8

SEQ ID NO: 9            moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 9
GGGGS                                                                     5

SEQ ID NO: 10           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 10
GSAGSAAGSG EF                                                             12

SEQ ID NO: 11           moltype = AA  length = 6
FEATURE                 Location/Qualifiers
REGION                  1..6
                        note = Description of Artificial Sequence: Synthetic 6xHis
                         tag
source                  1..6
                        mol_type = protein
                        organism = synthetic construct
SEQUENCE: 11
HHHHHH                                                                    6
```

What is claimed is:

1. A method of treating Friedreich's Ataxia (FRDA), said method comprising administering to a subject in need thereof a fusion polypeptide consisting of:
   a first peptide having an amino acid sequence of SEQ ID NO: 2;
   a second peptide having an amino acid sequence of SEQ ID NO: 4; and
   a 2-amino acid linker disposed between the first and second peptides.

2. The method of claim 1, wherein the 2-amino acid linker is Gly-Gly.

3. The method of claim 1, wherein the sequence of the fusion polypeptide, beginning at the N-terminus is: the first peptide, followed by the linker, followed by the second peptide.

4. A method of treating Friedreich's Ataxia (FRDA), said method comprising administering to a subject in need thereof a fusion polypeptide consisting of the amino acid sequence of SEQ ID NO: 1.

5. The method of any one of claims 1-4, wherein treating FRDA comprises treating an FRDA-associated disease.

6. The method of claim 5, wherein said FRDA-associated disease is selected from the group consisting of FRDA-associated pneumonia, FRDA-associated hypertrophic cardiomyopathy and FRDA-associated diabetes.

7. The method of claim 5, wherein said FRDA-associated disease is selected from the group consisting of loss of proprioception, loss of reflexes, loss of ability to walk, loss of ability to hold gaze with eyes, impaired swallowing, progressive loss of hearing, progressive loss of vision, progressive loss of speech, elevated triglycerides, low HDL cholesterol, elevated LDL cholesterol, scoliosis and combinations thereof.

8. The method of any one of claims 1-4, wherein the fusion polypeptide is administered subcutaneously.

9. The method of any one of claims 1-4, wherein the subject is a human.

10. A method of treating Friedreich's Ataxia (FRDA), said method comprising administering to a subject in need thereof a fusion polypeptide comprising:
    a first peptide having an amino acid sequence of SEQ ID NO: 2; and
    a second peptide having an amino acid sequence of SEQ ID NO: 4;
    wherein the first peptide is fused through a 2-amino acid linker to the second peptide.

11. The method of claim 10, wherein the 2-amino acid linker is Gly-Gly.

12. The method of claim 10, wherein the sequence of the fusion polypeptide, beginning at the N-terminus is: the first peptide, followed by the linker, followed by the second peptide.

13. A method of treating Friedreich's Ataxia (FRDA), said method comprising administering to a subject in need thereof a fusion polypeptide comprising the amino acid sequence of SEQ ID NO: 1.

14. The method of any one of claims 10-13, wherein treating FRDA comprises treating an FRDA-associated disease.

15. The method of claim 14, wherein said FRDA-associated disease is selected from the group consisting of FRDA-associated pneumonia, FRDA-associated hypertrophic cardiomyopathy and FRDA-associated diabetes.

16. The method of claim 14, wherein said FRDA-associated disease is selected from the group consisting of loss of proprioception, loss of reflexes, loss of ability to walk, loss of ability to hold gaze with eyes, impaired swallowing, progressive loss of hearing, progressive loss of vision, progressive loss of speech, elevated triglycerides, low HDL cholesterol, elevated LDL cholesterol, scoliosis and combinations thereof.

17. The method of any one of claims 10-13, wherein the fusion polypeptide is administered subcutaneously.

18. The method of any one of claims 10-13, wherein the subject is a human.

* * * * *